(12) United States Patent
Kovach et al.

(10) Patent No.: US 12,343,342 B2
(45) Date of Patent: *__Jul. 1, 2025__

(54) METHODS FOR TREATING SOFT TISSUE SARCOMA

(71) Applicant: Lixte Biotechnology, Inc., Pasadena, CA (US)

(72) Inventors: John S. Kovach, Pasadena, CA (US); Mickey L. Wells, Iowa City, IA (US)

(73) Assignee: Lixte Biotechnology, Inc., Pasadena, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 18/336,279

(22) Filed: Jun. 16, 2023

(65) Prior Publication Data

US 2024/0041864 A1    Feb. 8, 2024

Related U.S. Application Data

(60) Continuation of application No. 16/705,699, filed on Dec. 6, 2019, now Pat. No. 11,931,354, which is a division of application No. 14/783,360, filed as application No. PCT/US2014/033317 on Apr. 8, 2014, now Pat. No. 10,532,050.

(60) Provisional application No. 61/810,053, filed on Apr. 9, 2013.

(51) Int. Cl.
| | | |
|---|---|---|
| *A61K 31/496* | (2006.01) |
| *A61K 9/00* | (2006.01) |
| *A61K 31/197* | (2006.01) |
| *A61K 31/34* | (2006.01) |
| *A61K 31/4525* | (2006.01) |

(52) U.S. Cl.
CPC .......... *A61K 31/496* (2013.01); *A61K 9/0019* (2013.01); *A61K 31/197* (2013.01); *A61K 31/34* (2013.01); *A61K 31/4525* (2013.01)

(58) Field of Classification Search
CPC .. A61K 31/496; A61K 31/4525; A61K 31/34; A61K 31/197; A61K 31/195; A61K 2300/00; A61P 35/00
See application file for complete search history.

(56) References Cited

U.S. PATENT DOCUMENTS

| | | | |
|---|---|---|---|
| 2,957,906 A | 10/1960 | Erickson et al. |
| 3,227,473 A | 1/1966 | Halbern |
| 3,954,913 A | 5/1976 | Uebele et al. |
| 3,980,674 A | 9/1976 | Kubela et al. |
| 4,143,054 A | 3/1979 | Sprague |

(Continued)

FOREIGN PATENT DOCUMENTS

| | | |
|---|---|---|
| CN | 1586500 A | 3/2005 |
| CN | 103788108 A | 5/2014 |

(Continued)

OTHER PUBLICATIONS

Aarts, M. et al. (2012). Forced mitotic entry of S-phase cells as a therapeutic strategy induced by inhibition of WEE1. Cancer Discovery, 2(6), 524-539. https://doi.org/10.1158/2159-8290.CD-11-0320.

(Continued)

*Primary Examiner* — Sarah Pihonak
*Assistant Examiner* — Padmaja S Rao
(74) *Attorney, Agent, or Firm* — Banner & Witcoff, Ltd.

(57) ABSTRACT

The invention relates to a pharmaceutical composition comprising a protein phosphatase 2A (PP2A) inhibitor and monosodium glutamate.

5 Claims, 1 Drawing Sheet

(56) References Cited

U.S. PATENT DOCUMENTS

| | | |
|---|---|---|
| 4,218,478 A | 8/1980 | Omura et al. |
| 4,298,752 A | 11/1981 | Dauben et al. |
| 4,463,015 A | 7/1984 | Haslanger et al. |
| 4,518,696 A | 5/1985 | Gehrman et al. |
| 4,524,151 A | 6/1985 | Das et al. |
| 4,614,825 A | 9/1986 | Snitman et al. |
| 4,654,355 A | 3/1987 | Nakane et al. |
| 4,690,918 A | 9/1987 | Beppu et al. |
| 4,760,067 A | 7/1988 | Firestone |
| 4,816,579 A | 3/1989 | Thottathil |
| 4,851,423 A | 7/1989 | Girijavallabhan et al. |
| 4,851,553 A | 7/1989 | Thottathil |
| 5,206,386 A | 4/1993 | Narayanan et al. |
| 5,266,710 A | 11/1993 | Patel et al. |
| 5,326,898 A | 7/1994 | Chandraratna |
| 5,565,435 A | 10/1996 | Yoneyama et al. |
| 5,580,856 A | 12/1996 | Prestrelski et al. |
| 5,580,858 A | 12/1996 | Ippolito et al. |
| 5,763,647 A | 6/1998 | Ohtani et al. |
| 5,770,382 A | 6/1998 | Hwang et al. |
| 5,925,651 A | 7/1999 | Hutchinson |
| 5,968,965 A | 10/1999 | Dinsmore et al. |
| 6,222,055 B1 | 4/2001 | Wolter et al. |
| 6,262,116 B1 | 7/2001 | Pandolfi et al. |
| 6,632,823 B1 | 10/2003 | Vernier et al. |
| 6,696,483 B2 | 2/2004 | Singh |
| 6,706,762 B1 | 3/2004 | Evans et al. |
| 6,777,217 B1 | 8/2004 | Schreiber et al. |
| 6,905,669 B2 | 6/2005 | DiMartino |
| 6,949,624 B1 | 9/2005 | Liu et al. |
| 7,067,551 B2 | 6/2006 | Remiszewski et al. |
| 7,154,002 B1 | 12/2006 | Bressi et al. |
| 7,154,022 B2 | 12/2006 | Howe et al. |
| 7,834,019 B2 | 11/2010 | Sagara et al. |
| 7,893,096 B2 | 2/2011 | Valiante, Jr. |
| 7,943,743 B2 | 5/2011 | Korman et al. |
| 7,998,957 B2 | 8/2011 | Kovach et al. |
| 8,008,449 B2 | 8/2011 | Korman et al. |
| 8,058,268 B2 | 11/2011 | Kovach |
| 8,143,445 B2 | 3/2012 | Kovach et al. |
| 8,227,473 B2 | 7/2012 | Kovach et al. |
| 8,329,719 B2 | 12/2012 | Kovach |
| 8,354,509 B2 | 1/2013 | Carven et al. |
| 8,413,445 B2 | 4/2013 | Poyyapakkam |
| 8,426,444 B2 | 4/2013 | Kovach et al. |
| 8,455,668 B2 | 6/2013 | Fu et al. |
| 8,455,688 B2 | 6/2013 | Kovach et al. |
| 8,541,458 B2 | 9/2013 | Kovach et al. |
| 8,609,089 B2 | 12/2013 | Langermann et al. |
| 8,685,436 B2 | 4/2014 | Ley et al. |
| 8,697,845 B2 | 4/2014 | Ward et al. |
| 8,822,461 B2 | 9/2014 | Kovach et al. |
| 8,840,924 B2 | 9/2014 | Tengler et al. |
| 9,079,917 B2 | 7/2015 | Kovach et al. |
| 9,526,915 B2 | 12/2016 | Kovach |
| 9,833,450 B2 | 12/2017 | Kovach et al. |
| 9,988,394 B2 | 6/2018 | Kovach et al. |
| 9,994,584 B2 | 6/2018 | Piotrowski et al. |
| 10,023,587 B2 | 7/2018 | Kovach et al. |
| 10,071,092 B2 | 9/2018 | Jayaraman et al. |
| 10,071,094 B2 | 9/2018 | List et al. |
| 10,149,847 B2 | 12/2018 | Kovach |
| 10,364,252 B2 | 7/2019 | Kovach et al. |
| 10,399,993 B2 | 9/2019 | Kovach et al. |
| 10,413,541 B2 | 9/2019 | Kovach et al. |
| 10,434,100 B2 | 10/2019 | List et al. |
| 10,532,050 B2 | 1/2020 | Kovach et al. |
| 10,618,908 B2 | 4/2020 | Kovach et al. |
| 10,668,062 B2 | 6/2020 | Kovach |
| 11,236,102 B2 | 2/2022 | Kovach et al. |
| 2002/0115826 A1 | 8/2002 | Delorme et al. |
| 2002/0147345 A1 | 10/2002 | El Tayer et al. |
| 2002/0177692 A1 | 11/2002 | Bartel |
| 2003/0162186 A1 | 8/2003 | Bejanin et al. |
| 2003/0171329 A1 | 9/2003 | Jones et al. |
| 2004/0010045 A1 | 1/2004 | Yi |
| 2004/0053996 A1 | 3/2004 | Gesing et al. |
| 2004/0087531 A1 | 5/2004 | Telerman et al. |
| 2004/0087657 A1 | 5/2004 | Richon et al. |
| 2004/0106141 A1 | 6/2004 | Mischel et al. |
| 2004/0116366 A1 | 6/2004 | Monia et al. |
| 2004/0122101 A1 | 6/2004 | Miller et al. |
| 2004/0161475 A1 | 8/2004 | Ellison et al. |
| 2004/0197888 A1 | 10/2004 | Armour et al. |
| 2004/0209934 A1 | 10/2004 | McCluskey et al. |
| 2004/0253637 A1 | 12/2004 | Buechler et al. |
| 2005/0014839 A1 | 1/2005 | Kozikowski et al. |
| 2005/0020831 A1 | 1/2005 | Inman et al. |
| 2005/0054626 A1 | 3/2005 | Carter et al. |
| 2005/0119229 A1 | 6/2005 | Ammermann et al. |
| 2005/0136090 A1 | 6/2005 | Falotico et al. |
| 2005/0171202 A1 | 8/2005 | Graupner |
| 2005/0203082 A1 | 9/2005 | Hsu et al. |
| 2005/0215526 A1 | 9/2005 | Hulme et al. |
| 2005/0220831 A1 | 10/2005 | Jorsal |
| 2005/0222013 A1 | 10/2005 | Jung et al. |
| 2005/0272644 A1 | 12/2005 | Chung |
| 2005/0277583 A1 | 12/2005 | Yoshida et al. |
| 2005/0282893 A1 | 12/2005 | Au et al. |
| 2006/0030616 A1 | 2/2006 | McCluskey et al. |
| 2006/0117994 A1 | 6/2006 | Ryu et al. |
| 2006/0134682 A1 | 6/2006 | Roberts et al. |
| 2006/0167103 A1 | 7/2006 | Bacopoulos et al. |
| 2006/0235231 A1 | 10/2006 | Joel et al. |
| 2006/0264415 A1 | 11/2006 | Leit de Moradei et al. |
| 2007/0004771 A1 | 1/2007 | Lee et al. |
| 2007/0010669 A1 | 1/2007 | Breslow et al. |
| 2007/0049476 A1 | 3/2007 | Belcastro et al. |
| 2007/0049576 A1 | 3/2007 | Barlow et al. |
| 2007/0110669 A1 | 5/2007 | Driehuys et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2007/0280918 A1 | 12/2007 | Schwartz et al. |
| 2008/0097561 A1 | 4/2008 | Melsky et al. |
| 2008/0132503 A1 | 6/2008 | Moradei et al. |
| 2008/0214569 A1 | 9/2008 | Zhuang et al. |
| 2008/0267947 A1 | 10/2008 | Cirrito et al. |
| 2009/0012066 A1 | 1/2009 | Izumo et al. |
| 2009/0018142 A9 | 1/2009 | Zhuang et al. |
| 2009/0035292 A1 | 2/2009 | Kovach et al. |
| 2009/0036309 A1 | 2/2009 | Kovach et al. |
| 2009/0143445 A1 | 6/2009 | Kovach et al. |
| 2010/0016235 A1 | 1/2010 | Kroemer et al. |
| 2010/0028330 A1 | 2/2010 | Collins et al. |
| 2010/0029484 A1 | 2/2010 | Kovach et al. |
| 2010/0029640 A1 | 2/2010 | Kovach |
| 2010/0029683 A1 | 2/2010 | Kovach et al. |
| 2010/0137294 A1 | 6/2010 | Gasser et al. |
| 2011/0287537 A1 | 11/2011 | Kovach |
| 2012/0039906 A1 | 2/2012 | Olive |
| 2012/0114649 A1 | 5/2012 | Langermann et al. |
| 2012/0135522 A1 | 5/2012 | Kovach |
| 2012/0178783 A1 | 7/2012 | Kovach et al. |
| 2012/0264764 A1 | 10/2012 | Kovach et al. |
| 2012/0270736 A1 | 10/2012 | Kovach et al. |
| 2012/0316081 A1 | 12/2012 | List et al. |
| 2013/0280210 A1 | 10/2013 | Kovach |
| 2013/0302402 A1 | 11/2013 | Kovach et al. |
| 2014/0235649 A1 | 8/2014 | Kovach et al. |
| 2015/0045373 A1 | 2/2015 | Kovach et al. |
| 2015/0141661 A1 | 5/2015 | He et al. |
| 2015/0141669 A1 | 5/2015 | Hashihayata et al. |
| 2015/0148353 A1 | 5/2015 | Kovach |
| 2015/0174123 A1 | 6/2015 | Kovach |
| 2015/0210769 A1 | 7/2015 | Freeman et al. |
| 2015/0224083 A1 | 8/2015 | Cirrito et al. |
| 2016/0008336 A1 | 1/2016 | Kovach |
| 2016/0051544 A1 | 2/2016 | Kovach et al. |
| 2016/0074390 A1 | 3/2016 | Kovach |
| 2016/0264593 A1 | 9/2016 | Kovach et al. |

(56) References Cited

U.S. PATENT DOCUMENTS

| | | |
|---|---|---|
| 2016/0303115 A1 | 10/2016 | Kovach et al. |
| 2016/0333024 A1 | 11/2016 | Kovach et al. |
| 2017/0136008 A1 | 5/2017 | Kovach et al. |
| 2017/0209434 A1 | 7/2017 | List et al. |
| 2017/0240558 A1 | 8/2017 | Kovach et al. |
| 2017/0259081 A1 | 9/2017 | Kovach |
| 2017/0305925 A1 | 10/2017 | Piotrowski et al. |
| 2017/0340628 A1 | 11/2017 | List et al. |
| 2017/0369503 A1 | 12/2017 | Kovach et al. |
| 2018/0244690 A1 | 8/2018 | Kovach et al. |
| 2018/0256565 A1 | 9/2018 | Kovach et al. |
| 2018/0370983 A1 | 12/2018 | Kovach et al. |
| 2019/0046525 A1 | 2/2019 | List et al. |
| 2019/0111053 A1 | 4/2019 | List et al. |
| 2019/0167671 A1 | 6/2019 | Kovach |
| 2019/0359627 A1 | 11/2019 | Kovach et al. |
| 2020/0069680 A1 | 3/2020 | Kovach et al. |
| 2020/0179375 A1 | 6/2020 | Kovach et al. |
| 2020/0325151 A1 | 10/2020 | Kovach et al. |
| 2021/0275521 A1 | 9/2021 | Kovach |
| 2021/0379106 A1 | 12/2021 | Kovach et al. |
| 2022/0235066 A1 | 7/2022 | Kovach et al. |
| 2022/0323433 A2 | 10/2022 | List et al. |
| 2023/0065158 A1 | 3/2023 | Kovach et al. |
| 2023/0310418 A1 | 10/2023 | Kovach et al. |

FOREIGN PATENT DOCUMENTS

| | | |
|---|---|---|
| DE | 19600707 A1 | 7/1997 |
| EP | 1443967 A1 | 8/2004 |
| EP | 1443967 B1 | 1/2007 |
| FR | 2872704 A1 | 1/2006 |
| JP | 5069091 | 6/1975 |
| JP | S5069091 A | 6/1975 |
| JP | S5132733 A | 3/1976 |
| JP | 5188631 | 8/1976 |
| JP | S5188631 A | 8/1976 |
| JP | S5198755 A | 8/1976 |
| JP | H02256650 A | 10/1990 |
| JP | 2001329061 A | 11/2001 |
| JP | 2004531500 A | 10/2004 |
| JP | 2005507852 A | 3/2005 |
| JP | 2006507271 A | 3/2006 |
| JP | 2006519609 A | 8/2006 |
| JP | 2007511528 A | 5/2007 |
| JP | 2007514665 A | 6/2007 |
| RU | 2015980 C1 | 7/1994 |
| RU | 201598 U1 | 12/2020 |
| SU | 1553533 A1 | 3/1990 |
| WO | WO-9118891 A1 | 12/1991 |
| WO | WO-9604792 A1 | 2/1996 |
| WO | WO-0004023 A1 | 1/2000 |
| WO | WO-0162242 A1 | 8/2001 |
| WO | WO-0209680 A2 | 2/2002 |
| WO | WO-0228387 A1 | 4/2002 |
| WO | WO-0242310 A2 | 5/2002 |
| WO | WO-02066045 A2 | 8/2002 |
| WO | WO-02076989 A1 | 10/2002 |
| WO | WO-03045898 A1 | 6/2003 |
| WO | WO-03092616 A2 | 11/2003 |
| WO | WO-03092719 A2 | 11/2003 |
| WO | WO-2004035064 A1 | 4/2004 |
| WO | WO-2004080416 A2 | 9/2004 |
| WO | WO-2004087153 A2 | 10/2004 |
| WO | WO-2005018673 A1 | 3/2005 |
| WO | WO-2005049084 A2 | 6/2005 |
| WO | WO-2005054257 A1 | 6/2005 |
| WO | WO-2005058280 A2 | 6/2005 |
| WO | WO-2005074941 A1 | 8/2005 |
| WO | WO-2006016062 A1 | 2/2006 |
| WO | WO-2006023603 A2 | 3/2006 |
| WO | WO-2006052842 A2 | 5/2006 |
| WO | WO-2006121168 A1 | 11/2006 |
| WO | WO-2006129105 A1 | 12/2006 |
| WO | WO-2007005874 A2 | 1/2007 |
| WO | WO-2007014029 A2 | 2/2007 |
| WO | WO-2007021682 A1 | 2/2007 |
| WO | WO-2007092414 A2 | 8/2007 |
| WO | WO-2007118137 A1 | 10/2007 |
| WO | WO-2008028965 A2 | 3/2008 |
| WO | WO-2008030617 A2 | 3/2008 |
| WO | WO-2008058342 A1 | 5/2008 |
| WO | WO-2008097561 A1 | 8/2008 |
| WO | WO-2009020565 A1 | 2/2009 |
| WO | WO-2009045440 A1 | 4/2009 |
| WO | WO-2009101611 A1 | 8/2009 |
| WO | WO-2009114335 A2 | 9/2009 |
| WO | WO-2010014141 A1 | 2/2010 |
| WO | WO-2010014220 A1 | 2/2010 |
| WO | WO-2010014254 A1 | 2/2010 |
| WO | WO-2010027827 A2 | 3/2010 |
| WO | WO-2010077634 A1 | 7/2010 |
| WO | WO-2010147612 A1 | 12/2010 |
| WO | WO-2011066342 A2 | 6/2011 |
| WO | WO-2011132171 A1 | 10/2011 |
| WO | WO-2011143147 A1 | 11/2011 |
| WO | WO-2012162535 A1 | 11/2012 |
| WO | WO-2013056211 A2 | 4/2013 |
| WO | WO-2013180271 A1 | 12/2013 |
| WO | WO-2014005080 A1 | 1/2014 |
| WO | WO-2014005084 A1 | 1/2014 |
| WO | WO-2014089279 A1 | 6/2014 |
| WO | WO-2014137741 A1 | 9/2014 |
| WO | WO-2014149494 A1 | 9/2014 |
| WO | WO-2014168941 A1 | 10/2014 |
| WO | WO-2015073802 A1 | 5/2015 |
| WO | WO-2015196073 A1 | 12/2015 |
| WO | WO-2016014778 A1 | 1/2016 |
| WO | WO-2016014783 A1 | 1/2016 |
| WO | WO-2016040877 A1 | 3/2016 |
| WO | WO-2016061193 A1 | 4/2016 |
| WO | WO-2016134257 A1 | 8/2016 |
| WO | WO-2016168716 A1 | 10/2016 |
| WO | WO-2016186963 A1 | 11/2016 |
| WO | WO-2017049166 A1 | 3/2017 |
| WO | WO-2017132445 A1 | 8/2017 |
| WO | WO-2018107004 A1 | 6/2018 |
| WO | WO-2019113155 A1 | 6/2019 |
| WO | WO-2019241536 A1 | 12/2019 |
| WO | WO-2022159150 A1 | 7/2022 |
| WO | WO-2023133371 A2 | 7/2023 |

OTHER PUBLICATIONS

Abbas, A. A., "Synthesis of mixed-donor azaoxathia macrocyclic tetraamides, acyclic polyether di/and tetraamides and their C-pivot lariat derivatives," Journal of Heterocyclic Chemistry, vol. 44, Issue 3, May/Jun. 2007, pp. 651-661.

Abdel-Rahman, W. M. et al., "Spectral karyotyping suggests additional subsets of colorectal cancers characterized by pattern of chromosome rearrangement," Proc Natl Acad Sci USA, Feb. 2001;98(5):2538-43. doi: 10.1073/pnas.041603298. Epub Feb. 20, 2001.

Abel et al., "Epigenetic targets of HDAC inhibition in neurodegenerative and psychiatric disorders," Current Opinion in Pharmacology, vol. 8, No. 1, Feb. 2008 (pp. 57-64).

Abraham, D. et al., Raf-1-associated protein phosphatase 2A as a positive regulator of kinase activation. J Biol Chem 275(29):22300-22304 (Jul. 2000).

Acharya et al., "Rational development of histone deacetylase inhibitors as anticancer agents: a review," Molecular Pharmacology, vol. 68, No. 4, Oct. 2005 (pp. 917-932).

Adams, J. M. et al., The Bcl-2 protein family: arbiters of cell survival. Science 281:1322-1326 (Aug. 1998).

Adams, J. M. et al., Transgenic models of lymphoid neoplasia and development of a pan-hematopoietic vector. Oncogene 18:5268-5277 (1999).

Adcock, I.M. "HDAC inhibitors as anti-inflammatory agents", Br J Pharmacol. (2007), 150(7): 829-831.

Agata Y., et al., "Expression of the PD-1 antigen on the surface of stimulated mouse T and B lymphocytes," International Immunology, May 1996, vol. 8 (5), pp. 765-772.

(56) References Cited

OTHER PUBLICATIONS

Agoston. A. T. et al., "Retinoblastoma Pathway Dysregulation Causes DNA Methyltransferase 1 Overexpression in Cancer via MAD2-Mediated Inhibition of the Anaphase-Promoting Complex," The American Journal of Pathology, vol. 170, No. 5, pp. 1585-1593 (May 2007).

Ajay, A. K. et al., Cdk5 phosphorylates non-genotoxically overexpressed p53 following inhibition of PP2A to induce cell cycle arrest/apoptosis and inhibits tumor progression. Mol Cancer 9:204 (2010), 15 pages.

Albert, "Changing the trajectory of cognitive decline," New England Journal of Medicine, vol. 357, No. 5, Aug. 2007 (pp. 502-503).

Ambrogio, C. et al., In vivo oncogenic conflict triggered by co-existing KRAS and EGFR activating mutations in lung adenocarcinoma. Oncogene. Apr. 2017, 36(16):2309-2318.

Anderson, A.C. (2003) "The Process of Structure-Based Drug Design" Chem Biol, 10(9):787-797.

Andrabi et al., "Protein phosphatase 2A regulates life and death decisions via Akt in a context-dependent manner," Proceedings of the National Academy of Sciences U.S.A., vol. 104, No. 48, Nov. 2007 (pp. 19011-19016).

Andreatta, M. et al. (2021), "UCell: Robust and scalable single-cell gene signature scoring," Comput Struct Biotechnol J., vol. 19, pp. 3796-3798. 10.1016/j.csbj.2021.06.043.

Apostolidis, S. A. et al., "Protein Phosphatase 2A is Requisite for the Function of Regulatory T Cells," Nature Immunology, May 2016, vol. 17, No. 5, pp. 556-564.

Arakawa, T. et al., "The Mechanism of Action of Na Glutamate, Lysine HCI, and Piperazine-N,N' -bis(2-Ethanesulfonie Acid) in the Stabilization of Tubulin and Microtubule Formation*," The Journal of Biological Chemistry, Apr. 25, 1984, vol. 239, No. 8, pp. 4979-4986.

Arnold, C. P. et al., MicroRNA programs in normal and aberrant stem and progenitor cells. Genome Res. 21:798-810 (2011).

Arnold, H. K. et al., "A tumor suppressor role for PP2A-B56(alpha) through negative regulation of c-Myc and other key oncoproteins," Cancer Metastasis Review, vol. 27, No. 2, Jun. 2008, pp. 147-158.

Asquith, C. R. M. et al. (Mar. 2020). "PKMYT1: a forgotten member of the WEE1 family. Nature reviews." Nat. Rev. Drug Discov. 19(3):157. https://doi.org/10.1038/d41573-019-00202-9, 1 page.

Avila, J. et al. (Jan. 2006), "Tau Phosphorylation, Aggregation, and Cell Toxicity," Journal of Biomedicine and Biotechnology, vol. 2006, 5 pages.

Ayaydin et al., "Inhibition of serine/threonine-specific protein phosphatases causes premature activation of cdc2MsF kinase at G2/M transition and early mitotic microtubule organisation in alfalfa," The Plant Journal, vol. 23, No. 1, Jul. 2000 (pp. 85-96).

Bai , X. et al., "Inhibition of protein phosphatase 2A sensitizes pancreatic cancer to chemotherapy by increasing drug perfusion via HIF-1alpha-VEGF mediated angiogenesis," Cancer Letters 355(2):281-287 (2014).

Bai, X-L et al., "Inhibition of Protein Phosphatase 2A Enhances Cytotoxicity and Accessibility of Chemotherapeutic Drugs to Hepatocellular Carcinomas," Molecular Cancer Therapeutics, vol. 13, No. 8, pp. 2062-2072 (May 2014).

Baki, L. et al., "PS1 activates PI3K thus inhibiting GSK-3 activity and tau overphosphorylation: effects of FAD mutations," The EMBO Journal, vol. 23, No. 13, Jul. 2004, pp. 2586-2596.

Baki, L. et al., "Wild-Type But Not FAD Mutant Presenilin-1 Prevents Neuronal Degeneration by Promoting Phosphatidylinositol 3-Kinase Neuroprotective Signaling," The Journal of Neuroscience, vol. 28, No. 2, pp. 483-490 (Jan. 2008).

Balar, A. V. et al., "Atezolizumab as first-line treatment in cisplatin-ineligible patients with locally advanced and metastatic urothelial carcinoma: a single-arm, multicentre, phase 2 trial," Lancet, 2017;389(10064):67-76.

Bankhead, P. et al., QuPath: Open source software for digital pathology image analysis. Sci Rep 7, 16878 (2017), 7 pages.

Baroja M.L., et al., "Inhibition of CTLA-4 Function by the Regulatory Subunit of Serine/Threonine Phosphatase 2A," The Journal of Immunology, May 2002, vol. 168 (10), pp. 5070-5078.

Baskin, et al., "Inhibitors of protein kinases and phosphatases alter root morphology and disorganize cortical microtubules," Plant Physiology, vol. 113, No. 2, Feb. 1997, pp. 493-502.

Bastein, J. et al., "Nuclear Retinoid Receptors and the Transcription of Retinoid-target Genes," Gene, 2004, vol. 328, pp. 1-16.

Becht, E. et al. (Jan. 2019), "Dimensionality reduction for visualizing single-cell data using UMAP," Nature Biotechnology, vol. 37, No. 1, pp. 38-47.

Beck, H. et al. (2012). Cyclin-Dependent Kinase Suppression by WEE1 Kinase Protects the Genome through Control of Replication Initiation and Nucleotide Consumption. Molecular and Cellular Biology, 32(20), 4226-4236. https://doi.org/10.1128/mcb.00412-12.

Beglopoulos et al., "Regulation of CRE-dependent transcription by presenilins: prospects for therapy of Alzheimer's disease," Trends in Pharmacological Sciences, vol. 27, No. 1, Jan. 2006 (pp. 33-40).

Bengtsson, A. et al. (2020). The actual 5-year survivors of pancreatic ductal adenocarcinoma based on real-world data. Scientific Reports, 10(1):16425. https://doi.org/10.1038/s41598-020-73525-y, 9 pages.

Benito, A. et al., Apoptosis of human myeloid leukemia cells induced by an inhibitor of protein phosphatases (okadaic acid) is prevented by Bcl-2 and Bcl-X(L). Leukemia 11:940-944 (1997).

Berge, S. M., et al., "Pharmaceutical salts", Journal of Pharmaceutical Sciences (1977); 66(1): 1-19.

Bermudez, O. et al. (May 2010), "The dual-specificity MAP kinase phosphatases: critical roles in development and cancer," Am J Physiol Cell Physiol., vol. 299, pp. C189-C202.

Bernards, R., "Unconventional approaches to the treatment of cancer," PowerPoint Slides presented at the Dana-Farber Cancer Institute, AACR Annual Meeting (Apr. 2022), 16 pages.

Berry, L. D. et al., Chapter 10: Regulation of Cdc2 activity by phosphorylation at T14/Y15. Progress in Cell Cycle Research, Plenum Press, New York, 2:99-105 (1996).

Berthold et al., "Myeloablative megatherapy with autologous stem-cell rescue versus oral maintenance chemotherapy as consolidation treatment in patients with high-risk neuroblastoma: a randomised controlled trial," The Lancet Biology, vol. 6, No. 9, Sep. 2005 (pp. 649-658).

Bertini I., et al., "Structural Basis of Serine/Threonine Phosphatase Inhibition by the Archetypal Small Molecules Cantharidin and Norcantharidin," Journal of Medicinal Chemistry, Aug. 2009, vol. 52 (15), pp. 4838-4843.

Bian Y., et al., "Synthetic Genetic Array Screen Identifies PP2A as a Therapeutic Target in Mad2-Overexpressing Tumors," Proceedings of the National Academy of Sciences of the United States of America, Jan. 28, 2014, vol. 111 (4), pp. 1628-1633.

Blaheta et al., "Valproate and valproate-analogues: potent tools to fight against cancer," Current Medicinal Chemistry, vol. 9, No. 15, Aug. 2002 (pp. 1417-1433).

Blaskovich et al., "Recent discovery and development of protein tyrosince phosphatase inhibitors," Expert Opinion on Therapeutic Patents, vol. 12, No. 6, Jun. 2002 (pp. 871-905).

Bochner, B. R. et al., "Assay of the multiple energy-producing pathways of mammalian cells," PLoS One, vol. 6, Issue 3, e18147 (Mar. 2011), 8 pages.

Bodor, C. et al., "Elevated expression of Cu, Zn—SOD and Mn—SOD mRNA in inflamed dental pulp tissue," International Endodontic Journal, vol. 40, No. 2, pp. 128-132 (Feb. 2007).

Bollen, M. et al. (2010). The extended PP1 toolkit: Designed to create specificity. Trends in Biochemical Sciences, vol. 35, Issue 8, pp. 450-458. https://doi.org/10.1016/j.tibs.2010.03.002.

Bommer et al., "The translationally controlled tumor protein TCTP," International Journal of Biochemistry and Cell Biology, vol. 36, No. 3, Mar. 2004 (pp. 379-385).

Bonness, K. et al., Cantharidin-induced mitotic arrest is associated with the formation of aberrant mitotic spindles and lagging chromosomes resulting, in part, from the suppression of PP2Aalpha. Mol. Cancer Ther. 5(11):2727-2736 (2006).

(56) References Cited

OTHER PUBLICATIONS

Bononi, A. et al., Review Article: Protein kinases and phosphatases in the control of cell fate. Enzyme Res., vol. 2011, Article ID 329098 (2011), 26 pages.
Boschert, V. et al., "The Influence of Met Receptor Level on HGF-Induced Glycolytic Reprogramming in Head and Neck Squamous Cell Carcinoma," Int J Mol Sci 21:471 (2020), 17 pages.
Boudreau, R. T.M. et al., Apoptosis induced by protein phosphatase 2A (PP2A) inhibition in T leukemia cells is negatively regulated by PP2A-associated p38 mitogen-activated protein kinase. Cell Signal 19:139-151 (2007).
Bouscary, D. et al., Fas/Apo-1 (CD95) expression and apoptosis in patients with myelodysplastic syndromes. Leukemia 11:839-845 (1997).
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Brazil et al., "Advances in protein kinase B signalling AKTion on multiple fronts," Trends in Biochemical Sciences, vol. 29, No. 5, May 2004 (pp. 233-242).
Brunet J-F., et al., "A New Member of the Immunoglobulin Superfamily-CTLA-4," Nature, Jul. 16, 1987, vol. 328 (6127), pp. 267-270.
Bukhari, A. B. et al. (Mar. 2019), "Inhibiting Wee1 and ATR kinases produces tumor-selective synthetic lethality and suppresses metastasis," Journal of Clinical Investigation, vol. 129, No. 3, pp. 1329-1344.
Bundgaard H., "Novel Chemical Approaches in Prodrug Design", Drugs of the Future, Es, Prous Science, 1991, vol. 16, No. 5, p. 443-458.
Bunn, P. A. Jr. et al., "A phase I study of carboplatin and paclitaxel in non-small cell lung cancer: a University of Colorado Cancer Center study," Semin Oncol., 1995;22(4 Suppl 9):2-6.
Bunn, P. A. Jr., Review of therapeutic trials of carboplatin in lung cancer. Semin Oncol. 1989;16(2 Suppl 5):27-33.
Burgess, A. et al., Loss of human Greatwall results in G2 arrest and multiple mitotic defects due to deregulation of the cyclin B-Cdc2/PP2A balance. Proc Acad Sci USA 107(28):12564-12569 (Jul. 2010).
Burke, "Inhibition of mitogen-activated protein kinase and stimulation of Akt kinase signaling pathways: Two approaches with therapeutic potential in the treatment of neurodegenerative disease," Pharmacology & Therapeutics, vol. 114, No. 3, Jun. 2007 (pp. 261-277).
Cañadas, I. et al., Targeting epithelial-to-mesenchymal transition with Met inhibitors reverts chemoresistance in small cell lung cancer. Clin Cancer Res 20, 938-950 (2014).
Camphausen et al., "Influence of in vivo growth on human glioma cell line gene expression: convergent profiles under orthotopic conditions," Proceedings of the National Academy of Sciences U.S.A., vol. 102, No. 23, Jun. 2005 (pp. 8287-8292).
Caplus AN 1962:73368, Yur'ev, Y K. et al., "Furan Series. XVII. Synthesis of amino alcohols of the 3, 6-endoxocyclohexane series," Zhurnal Obshchei Khimii, (1961), 31, 2898-902, 2 pages.
Carreno B.M., et al., "CTLA-4 (CD152) can Inhibit T Cell Activation by Two Different Mechanisms Depending on its Level of Cell Surface Expression," The Journal of Immunology, Aug. 2000, vol. 165 (3), pp. 1352-1356.
Carter, L. L., et al., "PD-1: Pd-L inhibitory pathway affects both CD4+ and CD8+ T cells and is overcome by IL-2", European Journal of Immunology (2002); 32(3): 634-643.
Castedo et al., "Cell death by mitotic catastrophe: a molecular definition," Oncogene, vol. 23, No. 16, Apr. 2004 (pp. 2825-2837).
Cazzola, M. et al., "The genetic basis of myelodysplasia and its clinical relevance," Blood, vol. 122, No. 25, pp. 4021-4034 (Dec. 2013).
Champiat, S. et al., "Incorporating Immune-Checkpoint Inhibitors into Systemic Therapy of NSCLC," Journal of Thoracic Oncology, vol. 9, No. 2, pp. 144-153 (Feb. 2014).

Chan, L. N. et al. (Jul. 2020), "Signalling input from divergent pathways subverts B cell transformation," Nature, vol. 583, 31 pages. https://doi.org/10.1038/s41586-020-2513-4.
Chang et al., "All-trans-retinoic acid induces cell growth arrest in a human medullablastoma cell line," Journal of Neuro-Oncology, vol. 84, No. 3, Sep. 2007 (pp. 263-267).
Chang, K-E et al., "The protein phosphatase 2A inhibitor LB100 sensitizes ovarian carcinoma cells to cisplatin-mediated cytotoxicity," Mol. Cancer Ther. 14(1):90-100 (Jan. 2015).
Chapman N.M., et al., "mTOR Signaling, Tregs and Immune Modulation," Immunotherapy, 2014, vol. 6 (12), pp. 1295-1311.
Chen D.S., et al., "Oncology Meets Immunology: The Cancer-Immunity Cycle," Immunity, vol. 39 (1), Jul. 25, 2013, pp. 1-10.
Chen et al., "Mcl-1 Down-regulation Potentiates ABT-737 Lethality by Cooperatively Inducing Bak Activation and Bax Translocation," Cancer Research, vol. 67, No. 2, Jan. 2007 (pp. 782-791).
Chen, J. et al., Leukemogenesis: more than mutant genes. Nature Reviews Cancer, 10(1):23-36 (Jan. 2010).
Chen, J. T. et al., HGF increases cisplatin resistance via down-regulation of AIF in lung cancer cells. Am J Respir Cell Mol Biol 38, 559-565 (2008).
Chen, S. H. et al., "A knockout mouse approach reveals that TCTP functions as an essential factor for cell proliferation and survival in a tissue- or cell type-specific manner," Molecular Biology of the Cell, vol. 18, No. 7, Jul. 2007, pp. 2525-2532.
Chen, W. et al., "Identification of specific PP2A complexes involved in human cell transformation," Cancer Cell, vol. 5, No. 2 , pp. 127-136 (Feb. 2004).
Chen, X. et al., The microtubule depolymerizing agent CYT997 effectively kills acute myeloid leukemia cells via activation of caspases and inhibition of PI3K/Akt/mTOR pathway proteins. Exp Ther Med 6:299-304 (2013).
Chen, Y-N et al., Effector mechanisms of norcantharidin-induced mitotic arrest and apoptosis in human hepatoma cells. Int J Cancer 100:158-165 (2002).
Cheson, B. D. et al., "Clinical application and proposal for modification of the International Working Group (IWG) response criteria in myelodysplasia," Blood, vol. 108, No. 2, pp. 419-425 (Jul. 2006).
Cho et al., "Crystal structure of a protein phosphatase 2A heterotrimeric holoenzyme," Nature, vol. 445, No. 7123, Jan. 2007 (pp. 53-57).
Choi, J-W et al., "High expression of spindle assembly checkpoint proteins CDC20 and MAD2 is associated with poor prognosis in urothelial bladder cancer," Virchows Archiv., vol. 463, No. 5, Nov. 2013, pp. 681-687.
Chou et al., "Quantitative analysis of dose-effect relationships: the combined effects of multiple drugs or enzyme inhibitors", Advances in Enzyme Regulation, vol. 22, p. 27-55 (1984).
Chu, P-M et al., Review: Deregulated microRNAs identified in isolated glioblastoma stem cells: an overview. Cell Transplantation, 22:741-753 (2013).
Chuang E., et al., "The CD28 and CTLA-4 Receptors Associate with the Serine/Threonine Phosphatase PP2A," Immunity, Sep. 2000, vol. 13, pp. 313-322.
Chung, V. et al., "Safety, Tolerability, and Preliminary Activity of LB-100, an Inhibitor of Protein Phosphatase 2A, in patients with Relapsed Solid Tumors: An Open-Label, Dose Escalation, First-in-Human, Phase I Trial," Clin Cancer Res, vol. 23, No. 13, pp. 3277-3284 (Jul. 2017).
Chung, V. M. et al., "A phase 1 study of a novel inhibitor of protein phosphatase 2A alone and with docetaxel," Meeting Abstract, 2014 ASCO Annual Meeting, Abstract TPS2636 (2014), 2 pages.
Ciccone, M. et al. (Feb. 2015). From the biology of PP2A to the PADs for therapy of hematologic malignancies. Frontiers in Oncology, vol. 5, Article 21, https://doi.org/10.3389/fonc.2015.00021, 10 pages.
Cogle, C. et al., Incidence of the myelodysplastic syndromes using a novel claims-based algorithm: high number of uncaptured cases by cancer registries. Blood 117(26):7121-7125 (2011).
Cohen, M. V. et al., "Is it time to translate ischemic preconditioning's mechanism of cardioprotection into clinical practice?" Journal of Cardiovascular Pharmacology and Therapeutics, vol. 16, No. 3-4, Sep.-Dec. 2011, pp. 273-280.

(56) References Cited

OTHER PUBLICATIONS

Cohen, P., "The Structure and Regulation of Protein Phosphatases," Annual Review of Biochemistry, 1989, vol. 58, pp. 453-508.
Coleman, T. R. et al., Cdc2 regulatory factors. Curr. Opin. Cell Biol., 6:877-882 (1994).
Coles, G. L. et al., "Unbiased Proteomic Profiling Uncovers a Targetable GNAS/PKA/PP2A Axis in Small Cell Lung Cancer Stem Cells," Cancer Cell, 38:129-143 (Jul. 2020), pp. 129-143.
Colic, M. et al. (Aug. 2019), "Identifying chemogenetic interactions from CRISPR screens with drugZ," Genome Medicine, vol. 11, No. 52, 12 pages.
Crafts, "Herbicides," Annual Review of Plant Physiology, vol. 4, Jun. 1953 (pp. 253-282).
Craig, "MCL1 provides a window on the role of the BCL2 family in cell proliferation, differentiation and tumorigenesis," Leukemia, vol. 16, No. 4, Apr. 2002 (pp. 444-454).
David et al., "Histone deacetylase associated with mSin3A mediates repression by the acute promyelocytic leukemia-associated PLZF protein," Oncogene, vol. 16, No. 19, May 1998 (pp. 2549-2556).
Davis, R. E. et al., Bcl-2 expression by myeloid precursors in myelodysplastic syndromes: relation to disease progression. Leuk Res 22:767-777 (1998).
De Coana, Y. P. et al., "Checkpoint Blockade for Cancer Therapy: Revitalizing a Suppressed Immune System," Trends in Molecular Medicine, Aug. 2015, vol. 21, No. 8, pp. 482-491.
De Luca, A. et al., "The RAS/RAF/MEK/ERK and the PI3K/AKT signalling pathways: role in cancer pathogenesis and implications for therapeutic approaches," Expert Opin Ther Targets 16(Suppl 2), S17-S27 (2012).
De Witt Hamer, P. C. et al. (2011). WEE1 kinase targeting combined with DNA-damaging cancer therapy catalyzes mitotic catastrophe. Clinical Cancer Research, vol. 17, Issue 13, pp. 4200-4207. https://doi.org/10.1158/1078-0432.CCR-10-2537.
Delgoffe, G. M. et al., "The Mammalian Target of Rapamycin (mTOR) Regulates T Helper Cell Differentiation through the Selective Activation of mTORC1 and mTORC2 Signaling," Nature Immunology, Apr. 2011, vol. 12, No. 4, pp. 295-303.
Delgoffe G.M., "PP2A's Restraint of mTOR is Critical for T(reg) Cell Activity," Nature Immunology, May 2016, vol. 17 (5), pp. 478-479.
Di Fagagna, F., "Living on a break: cellular senescence as a DNA-damage response," Nature Reviews Cancer, vol. 8, No. 7, Jul. 2008, pp. 512-522.
Dias, M. H. et al. (2019). Fibroblast Growth Factor 2 lethally sensitizes cancer cells to stress-targeted therapeutic inhibitors. Molecular Oncology, 13(2), 290-306. https://doi.org/10.1002/1878-0261.12402.
Dias, M. H. et al., "Paradoxical activation of oncogenic signaling as a cancer treatment strategy," Feb. 2023, bioRxiv preprint doi: https://doi.org/10.1101/2023.02.06.527335, 79 pages.
Dias, M. H. et al., "Playing cancer at its own game: activating mitogenic signaling as a paradoxical intervention," Mol Oncol. Aug. 2021;15(8):1975-1985.
DiFeo, T. J., "Drug Product Development: A Technical Review of Chemistry, Manufacturing, and Controls Information for the Support of Pharmaceutical Compound Licensing Activities," Drug Development and Industrial Pharmacy, Aug. 2003, vol. 29, No. 9, pp. 939-958.
Dreesen et al., "Signaling pathways in cancer and embryonic stem cells," Stem Cell Review, vol. 3, No. 1, Jan. 2007 (pp. 7-17).
Drewinko et al., "Combination chemotherapy in vitro with adriamycin. Observations of additive, antagonistic, and synergistic effects when used in two-drug combinations on cultured human lymphoma cells," Cancer Biochemistry Biophysics, vol. 1, No. 4, May 1976 (pp. 187-195).
Duda, H. et al. (Dec. 2016), "A Mechanism for Controlled Breakage of Under-replicated Chromosomes during Mitosis," Developmental Cell, vol. 39, pp. 740-755. http://dx.doi.org/10.1016/j.devcel.2016.11.017.
Duong, F. H. et al., Hepatitis C virus inhibits interferon signaling through up-regulation of protein phosphatase 2A. Gastroenterology 126, 263-277 (2004).
Duong, F. H. et al., Protein phosphatase 2A promotes hepatocellular carcinogenesis in the diethylnitrosamine mouse model through inhibition of p53. Carcinogenesis 35, 114-122 (2014).
Durusu, I. Z. et al., "Anti-Cancer Effect of Clofazimine as a Single Agent and in Combination with Cisplatin on U266 Multiple Myeloma Cell Line," Leukemia Research, Apr. 2017, vol. 55, pp. 33-40.
Ebert, B. L. et al., "Identification of RPS14 as a 5q-syndrome gene by RNA interference screen," Nature, vol. 451, No. 7176, pp. 335-339 (Jan. 2008).
Ebert P.J.R., et al., "MAP Kinase Inhibition Promotes T Cell and Anti-tumor Activity in Combination with PD-L1 Checkpoint Blockade," Immunity, Mar. 15, 2016, vol. 44, pp. 609-621.
Eckardt, J. R. et al., "Open-label, multicenter, randomized, phase III study comparing oral topotecan/cisplatin versus etoposide/cisplatin as treatment for chemotherapy-naive patients with extensive-disease small-cell lung cancer," J Clin Oncol. 2006;24(13):2044-2051.
Ecker, V. et al. (Jun. 2021), "Targeted PI3K/AKT-hyperactivation induces cell death in chronic lymphocytic leukemia," Nature Communications, vol. 12, No. 3526, 17 pages. https://doi.org/10.1038/s41467-021-23752-2.
Efferth, T. et al., "Activity of Drugs from Traditional Chinese Medicine Toward Sensitive and MDR1- or MRP1-Overexpressing Multidrug-Resistant Human CCRF-CEM Leukemia Cells," Blood Cells Molecules and Diseases, Mar.-Apr. 2002, vol. 28, No. 2, pp. 160-168.
Efferth, T. et al., "Molecular Modes of Action of Cantharidin in Tumor Cells," Biochemical Pharmacology, Mar. 2005, vol. 69, No. 5, pp. 811-818.
Eichhorn, P. J.A. et al., Review: Protein phosphatase 2A regulatory subunits and cancer. Biochim Biophys Acta 1795:1-15 (2009).
Eil, R. et al., "Ionic Immune Suppression within the Tumour Microenvironment Limits T Cell Effector Function," Nature, Sep. 2016, vol. 537, No. 7621, pp. 1-42.
Elbaek, C. R. et al. (2022). WEE1 kinase protects the stability of stalled DNA replication forks by limiting CDK2 activity. Cell Reports, 38(3). https://doi.org/10.1016/j.celrep.2021.110261, 14 pages.
Engel, T. et al., "Full Reversal of Alzheimer's Disease-Like Phenotype in a Mouse Model with Conditional Overexpression of Glycogen Synthase Kinase-3," The Journal of Neuroscience, vol. 26, No. 19 (May 2006), pp. 5083-5090.
Erdodi, F. et al. (Nov. 1995), "Endothall thianhydride inhibits protein phosphatases-1 and -2A in vivo," American Journal of Physiology, vol. 269, No. 5 Pt 1, pp. C1176-C1184.
Essers et al., "Synthesis of the first fluorinated cantharidin analogues," Tetrahedron Letters, vol. 42, No. 32, Aug. 2001 (pp. 5429-5433).
Extended European Search Report for European Application No. 14783185.3, mailed Nov. 21, 2016, 7 pages.
Fabel et al., "Long-term stabilization in patients with malignant glioma after treatment with liposomal doxorubicin," Cancer, vol. 92, No. 7, Oct. 2001 (pp. 1936-1942).
Falconer I.R., et al., "Preliminary Evidence for In Vivo Tumour Initiation by Oral Administration of Extracts of the Blue-Green Alga Cylindrospermopsis Raciborskii Containing the Toxin Cylindrospermopsin," Short Communication, Environmental Toxicology, 2001, vol. 16 (2), pp. 192-195.
Fang, Y. et al. (Jun. 2019), "Sequential Therapy with PARP and WEE1 Inhibitors Minimizes Toxicity while Maintaining Efficacy," Cancer Cell, vol. 35, pp. 851-867. https://doi.org/10.1016/j.ccell.2019.05.001.
Fang, Z. et al. (Nov. 2022), "GSEApy: a comprehensive package for performing gene set enrichment analysis in Python," Bioinformatics, vol. 39, No. 1, 3 pages. https://doi.org/10.1093/bioinformatics/btac757.
Fanghanel, E. et al. (Oct. 1994), "Cycloaddition Reactions of [1,]Dithiolo[1,2]dithiole Derivatives with Dimethyl Acetylenedicarboxylate: Formation of New Bi-, Tri- and Tetracyclic Thiopyran Derivatives," Synthesis, vol. 10, pp. 1067-1071.

(56) References Cited

OTHER PUBLICATIONS

Faoro, L. et al., EphA2 mutation in lung squamous cell carcinoma promotes increased cell survival, cell invasion, focal adhesions, and mammalian target of rapamycin activation. J Biol Chem 285, 18575-18585 (2010).

Federal Register Online via the Government Publishing Office, Federal Register, vol. 66, No. 4, Jan. 2001, 19 pages.

Fehrenbacher, L. et al., "Atezolizumab versus docetaxel for patients with previously treated non-small-cell lung cancer (Poplar): a multicentre, open-label, phase 2 randomised controlled trial," Lancet, Apr. 2016;387(10030): 1837-1846.

Ferron, P-J et al., Comparative analysis of the cytotoxic effects of okadaic acid-group toxins on human intestinal cell lines. Mar. Drugs 12:4616-4634 (2014).

Finger, E. C. et al., "Hypoxia, inflammation, and the tumor microenvironment in metastatic disease," Cancer Metastasis Rev., vol. 29, pp. 285-293 (2010).

Finnin, M. S. et al., "Structures of a histone deacetylase homologue bound to the TSA and SAHA inhibitors," Nature (Sep. 1999), vol. 401, pp. 188-193.

Fischer et al., "Recovery of learning and memory is associated with chromatin remodelling," Nature, vol. 447, No. 7141, May 2007 (pp. 178-182).

Flicker et al., "Tyrosine kinase signaling pathways control the expression of retinoic acid receptor-alpha in SK-BR-3 breast cancer cells," Cancer Letters, vol. 115, No. 1, May 1997 (pp. 63-72).

Forester, C. M. et al., "Control of mitotic exit by PP2A regulation of Cdc25C and Cdk1," Proceedings of the National Academy of Sciences U.S.A., vol. 104, No. 50, Dec. 2007, pp. 19867-19872.

Francia, G. et al., Identification by differential display of a protein phosphatase-2A regulatory subunit preferentially expressed in malignant melanoma cells. Int J Cancer 82:709-713 (1999).

Frasor, J. et al., "Estrogen down-regulation of the Corepressor N-CoR: Mechanism and implications for estrogen derepression of N-CoR-Regulated Genes," Proceedings of the National Academy of Sciences of the United States of America, vol. 102, No. 37, (Sep. 2005), pp. 13153-13157.

Freeman, G. J., et al., "Engagement of the PD-1 immunoinhibitory receptor by a novel B7 family member leads to negative regulation of lymphocyte activation", The Journal of Experimental Medicine (2000); 192(7): 1027-1034.

Fung, M. K.-L. et al., "MAD2 expression and its significance in mitotic checkpoint control in testicular germ cell tumour," Biochimica et Biophysica Acta, vol. 1773, No. 6, Jun. 2007, pp. 821-832.

Furumai, R. et al., "Potent histone deacetylase inhibitors built from trichostatin A and cyclic tetrapeptide antibiotics including trapoxin", Proc Natl Acad Sci U S A. (2001), 98(1): 87-92.

Gachet et al., "The growth-related, translationally controlled protein P23 has properties of a tubulin binding protein and associates transiently with microtubules during the cell cycle," Journal of Cell Science, vol. 112, pt. 8, Apr. 1999 (pp. 1257-1271).

Gallo, D. et al. (2022). CCNE1 amplification is synthetic lethal with PKMYT1 kinase inhibition. Nature, vol. 604, No. 7907, pp. 749-756. https://doi.org/10.1038/s41586-022-04638-9.

Gandino, L. et al., Phosphorylation of serine 985 negatively regulates the hepatocyte growth factor receptor kinase. J Biol Chem 269, 1815-1820 (1994).

Garcia-Echeverria et al., "Drug discovery approaches targeting the PI3K/Akt pathway in cancer," Oncogene, vol. 27, No. 41, Sep. 2008 (pp. 5511-5526).

Gatzemeier, U. et al., "Phase II and III studies with carboplatin in small cell lung cancer," Semin Oncol., Feb. 1992, vol. 19, No. 1, Suppl. 2, pp. 28-36.

Ge, X. Q. et al. (2007). Dormant origins licensed by excess Mcm2-7 are required for human cells to survive replicative stress. Genes and Development, vol. 21, No. 24, pp. 3331-3341. https://doi.org/10.1101/gad.457807.

Gehringer M.M., "Microcystin-LR and Okadaic Acid-Induced Cellular Effects: A Dualistic Response," The Federation of European Biochemical Societies Letters, Jan. 16, 2004, vol. 557, pp. 1-8.

Gendron, S. et al., Integrin alpha2beta1 inhibits Fas-mediated apoptosis in T lymphocytes by protein phosphatase 2A-dependent activation of the MAPK/ERK pathway. J Biol Chem 278(49):48633-48643 (Dec. 2003).

Germain, P-L et al. (Sep. 2021), "Doublet identification in single-cell sequencing data using scDblFinder [version 1; peer review: 1 approved, 1 approved with reservations]," F1000Research, vol. 10, No. 979, 23 pages. https://doi.org/10.12688/f1000research.73600.1.

Giagounidis, A. et al., "Clinical, morphological, cytogenetic, and prognostic features of patients with myelodysplastic syndromes and del(5q) including band q31," Leukemia, vol. 18, No. 1, pp. 113-119 (Jan. 2004).

Giannini, R. et al., "Expression Analysis of a Subset of Coregulators and Three Nuclear Receptors in Human Colorectal Carcinoma," Anticancer Research, vol. 25, No. 6B, Nov. 2005, pp. 4287-4292.

Godlewski, J. et al., microRNA-451: A conditional switch controlling glioma cell proliferation and migration. Cell Cycle, 9(14):2814-2820 (Jul. 2010).

Godlewski, J. et al., microRNA-451 regulates LKB1/AMPK signaling and allows adaptation to metabolic stress in glioma cells. Mol Cell 37:620-632 (Mar. 2010).

Godlewski, J. et al., MicroRNAs and glioblastoma; the stem cell connection. Cell Death and Differentiation, 17:221-228 (2010).

Gong, C.-X. al., "Post-translational modifications of tau protein in Alzheimer's disease," J. Neural Transmission, vol. 112, (2005), pp. 813-838.

Gordon, I. K. et al., "Protein Phosphatase 2A Inhibition with LB100 Enhances Radiation-Induced Mitotic Catastrophe and Tumor Growth Delay in Glioblastoma," Molecular Cancer Therapeutics, Jul. 2015, vol. 14, No. 7, pp. 1540-1547.

Gorecki, L. et al. (Feb. 2021), Clinical candidates targeting the ATR-CHK1-WEE1 axis in cancer, Cancers, vol. 13, Issue 4, pp. 1-22. Published online Feb. 14, 2021. doi: 10.3390/cancers13040795.

Gottlicher et al., "Valproic acid defines a novel class of HDAC inhibitors inducing differentiation of transformed cells," EMBO Journal, vol. 20, No. 24, Dec. 2001 (pp. 6969-6978).

Graziano, M. J. et al., "Comparison of the acute toxicity of endothal and cantharidic acid on mouse liver in vivo," Toxicology Letters, vol. 37, No. 2, Jul. 1987, pp. 143-148.

Greenberg, P. et al., "International scoring system for evaluating prognosis in myelodysplastic syndromes," Blood, vol. 89, No. 6, pp. 2079-2088 (Mar. 1997) with Erratum.

Greenberg, P. L. et al., "Myelodysplastic syndromes: clinical practice guidelines in oncology," J. Natl. Compr. Canc. Netw., vol. 11, No. 7, pp. 838-874 (Jul. 2013).

Greenberg, P. L. et al., "Revised International Prognostic Scoring System for Myelodysplastic Syndromes," Blood, vol. 120, No. 12, pp. 2454-2465 (Sep. 2012).

Grimes, C. A. et al., "The multifaceted roles of glycogen synthase kinase 3(beta) in cellular signaling," Progress in Neurobiology, vol. 65, Issue 4, Nov. 2001, pp. 391-426.

Groenendijk, F. H. et al. (2014). Drug resistance to targeted therapies: déjà vu all over again. Molecular Oncology, 8(6):1067-1083. https://doi.org/10.1016/j.molonc.2014.05.004.

Grosso J.F., et al., "CTLA-4 Blockade in Tumor Models: An Overview of Preclinical and Translational Research," Cancer Immunity, Jan. 22, 2013, vol. 13 (5), pp. 1-14.

Gumireddy et al., "All-trans-retinoic acid-induced apoptosis in human medulloblastoma: activation of caspase-3/poly (ADP-ribose) polymerase 1 pathway," Clinical Cancer Research, vol. 9, No. 11, Sep. 2003 (pp. 4052-4059).

Gwinn, D. et al., "The Phosphatase PP2A Links Glutamine to the Tumor Suppressor p53," Molecular Cell, vol. 50, No. 2, Apr. 2013, pp. 157-158.

Haase, D. et al., "New insights into the prognostic impact of the karyotype in MDS and correlation with subtypes: evidence from a core dataset of 2124 patients," Blood, vol. 110, No. 13, pp. 4385-4395 (Dec. 2007).

Hanahan, D. et al. (Jan. 2000). The Hallmarks of Cancer. Review. Cell, 100(1):57-70. https://doi.org/10.1007/s00262-010-0968-0.

(56) References Cited

OTHER PUBLICATIONS

Hardy-Werbin, M. et al., "MET Inhibitors in Small Cell Lung Cancer: From the Bench to the Bedside," Cancers, 11:1404 (2019), 14 pages.
Hart, M.E., et al., "Modified norcantharidins: synthesis, protein phosphatases 1 and 2A inhibition, and anticancer activity," Bioorganic & Medicinal Chemistry Letters, vol. 14, No. 8, pp. 1969-1973 (Apr. 2004).
Hashigasako, A. et al., Bidirectional regulation of Ser-985 phosphorylation of c-met via protein kinase C and protein phosphatase 2A involves c-Met activation and cellular responsiveness to hepatocyte growth factor. J Biol Chem 279, 26445-26452 (2004).
Havrilesky L.J., et al., "Relationship Between Expression of Coactivators and Corepressors of Hormone Receptors and Resistance of Ovarian Cancers to Growth Regulation by Steroid Hormones," Journal of the Society of the Gynecologic Investigation, Mar./Apr. 2001, vol. 8 (2), pp. 104-113.
Hawkins C.E., et al., "Molecular Genetic Approaches and Potential New Therapeutic Strategies for Pediatric Diffuse Intrinsic Pontine Glioma," Journal of Clinical Oncology, Oct. 2011, vol. 29 (30), pp. 3956-3957.
Haxhinasto S., et al., "The AKT-mTOR Axis Regulates de Novo Differentiation of CD4+Foxp3+ cells," Journal of Experimental Medicine, Mar. 17, 2008, vol. 205 (3), pp. 565-574.
He, L. et al., MicroRNAs: small RNAs with a big role in gene regulation. Nat. Rev. Genet., 5:522-531 (Jul. 2004).
Hein, A. L. et al., "PR55α Subunit of Protein Phosphatase 2A Supports the Tumorigenic and Metastatic Potential of Pancreatic Cancer Cells by Sustaining Hyperactive Oncogenic Signaling," Cancer Research, Apr. 2016, vol. 76, No. 8, pp. 2243-2253.
Hermanson, O. et al., "N-CoR Controls Differentiation of Neural Stem Cells into Astrocytes," Nature, Oct. 31, 2002, vol. 419, pp. 934-939.
Hildmann et al., "Histone-deacetylases—an important class of cellular regulators with a variety of functions," Applied Microbiology and Biotechnology, vol. 75, No. 3, Jun. 2007 (pp. 487-497).
Hill, T. A. et al., "Heterocyclic Substituted Cantharidin and Norcantharidin Analogues—Synthesis, Protein Phosphatase (1 and 2A) Inhibition, and Anti-cancer Activity," Bioorganic & Medicinal Chemistry Letters, 2007, vol. 17, No. 12, pp. 3392-3397.
Hirose et al., "Akt activation suppresses Chk2-mediated methylating agent-induced G2 arrest and protects from temozolomide-induced mitotic catastrophe and cellular senescence," Cancer Research, vol. 65, No. 11, Jun. 2005 (pp. 4861-4869).
Hisaoka, M. et al., "Aberrant MAD2 expression in soft-tissue sarcoma," Pathology International, vol. 58, No. 6, Jun. 2008, pp. 329-333.
Ho, W. S. et al., "Abstract LB-193: Protein phosphatase 2A inhibition, with a novel small molecule inhibitor, LB-100, achieves durable immune-mediated antitumor activity when combined with PD1 blockade in a preclinical model," Poster Presentations, Cancer Res (Jul. 2017) 77 (13_Supplement): LB-193, 2 pages.
Ho, W. S. et al., "Pharmacologic Inhibition of Protein Phosphatase-2A Achieves Durable Immune-Mediated Antitumor Activity When Combined With PD-1 Blockade," Nature Communications, 2018, vol. 9, Article No. 2126, pp. 1-15.
Ho, W. S. et al., "PP2A Inhibition with LB100 Enhances Cisplatin Cytotoxicity and Overcomes Cisplatin Resistance in Medulloblastoma Cells," Oncotarget, Mar. 2016, vol. 7, No. 11, pp. 12447-12463.
Hodi, F. S. et al. "Improved survival with ipilimumab in patients with metastatic melanoma." New England Journal of Medicine 363.8 (2010): 711-723.
Hofstetter, C. P. et al., "Protein Phosphatase 2A Mediates Dormancy of Glioblastoma Multiforme-Derived Tumor Stem-like Cells During Hypoxia," Public Library of Science ONE, Jan. 2012, vol. 7, No. 1, pp. 1-11.
Holford, N. H.G. et al., Understanding the dose-effect relationship: clinical application of pharmacokinetic-pharmacodynamic models. Clin. Pharmacokinet, 6(6):429-453 (Nov.-Dec. 1981).
Holmgaard, R. B. et al., "Indoleamine 2,3-dioxygenase is a critical resistance mechanism in antitumor T cell immunotherapy targeting CTLA-4," Journal of Experimental Medicine, vol. 210, No. 7, (2013), pp. 1389-1402.
Hong, C., et al., "Norcantharidin-induced post-G2/M Apoptosis is Dependent on Wild-Type p53 Gene," Biochem. Biophys. Res. Comm., vol. 276, No. 1, pp. 278-285 (Sep. 2000).
Hong, C. S. et al. (2015). LB100, a small molecule inhibitor of PP2A with potent chemo- and radio-sensitizing potential. Cancer Biology and Therapy vol. 16, Issue 6, pp. 821-833. https://doi.org/10.1080/15384047.2015.1040961.
Honkanen, R. E., "Cantharidin, Another Natural Toxin That Inhibits the Activity of Serine/threonine Protein Phosphatases Types 1 and 2A," The Federation of European Biochemical Societies (FEBS) Letters, vol. 330, No. 3, Sep. 1993, pp. 283-286.
Honkanen, R. E. et al., "Regulators of Serine/Threonine Protein Phosphatases at the Dawn of a Clinical Era?" Curr. Med. Chem, vol. 9, No. 22, (2002), pp. 2055-2075.
Horn, L. et al., First-Line Atezolizumab plus Chemotherapy in Extensive-Stage Small-Cell Lung Cancer. N Engl J Med. 2018;379(23):2220-2229.
Hoshikawa et al., "Trichostatin A induces morphological changes and gelsolin expression by inhibiting histone deacetylase in human carcinoma cell lines," Experimental Cell Research, vol. 214, No. 1, Sep. 1994 (pp. 189-197).
Hu, C. et al., "PP2A inhibition from LB100 therapy enhances daunorubicin cytotoxicity in secondary acute myeloid leukemia via miR-181b-1 upregulation," Scientific Reports, 7(1):2894 (Jun. 2017), 14 pages.
Huan, S. K-H et al., Cantharidin-induced cytotoxicity and cyclooxygenase 2 expression in human bladder carcinoma cell line. Toxicology 223:136-143 (2006).
Huang, B. et al., Metabolic control of Ca2+/calmodulin-dependent protein kinase II (CaMKII)-mediated caspase-2 suppression by the B55beta/protein phosphatase 2A (PP2A). J Biol Chem 289(52):35882-35890 (Dec. 2014).
Huang, D. C. S. et al., BH3-Only proteins-essential initiators of apoptotic cell death. Cell, 103:839-842 (Dec. 2000).
Huang, "Targeting histone deacetylases for the treatment of cancer and inflammatory diseases," Journal of Cell Physiology, vol. 209, No. 3, Dec. 2006 (pp. 611-616).
Huang, W-W et al., Cantharidin induces G2/M phase arrest and apoptosis in human colorectal cancer colo 205 cells through inhibition of CDKI activity and caspase- dependent signaling pathways. Int J Oncol 38:1067-1073 (2011).
Hughes et al., "Ciliary neurotrophic factor induces type-2 astrocyte differentiation in culture," Nature, vol. 335, No. 6185, Sep. 1988 (pp. 70-73).
Ianzini et al., "Delayed DNA damage associated with mitotic catastrophe following X-irradiation of HeLa S3 cells," Mutagenesis, vol. 13, No. 4, Jul. 1998 (pp. 337-344).
Ibarra, A. et al. (2008). Excess MCM proteins protect human cells from replicative stress by licensing backup origins of replication. Proceedings of the National Academy of Sciences of the United States of America, 105(26):8956-8961. https://doi.org/10.1073/pnas.0803978105.
International Preliminary Report on Patentability for International Application No. PCT/US2008/001549, mailed Aug. 11, 2009, 6 pages.
International Preliminary Report on Patentability for International Application No. PCT/US2009/004108, dated Feb. 1, 2011, 6 pages.
International Preliminary Report on Patentability for International Application No. PCT/US2014/033317, mailed Oct. 22, 2015, 14 pages.
International Preliminary Report on Patentability for International Application No. PCT/US2015/041709, mailed Feb. 2, 2017, 7 pages.
International Preliminary Report on Patentability for International Application No. PCT/US2015/041714, mailed Feb. 2, 2017, 8 pages.
International Preliminary Report on Patentability for International Application No. PCT/US2018/063980, mailed Jun. 18, 2020, 7 pages.

(56) References Cited

OTHER PUBLICATIONS

International Preliminary Report on Patentability for International Application No. PCT/US2019/037015, mailed Dec. 24, 2020, 7 pages.
International Preliminary Report on Patentability for International Application No. PCT/US2021/051647 dated Aug. 3, 2023, 6 pages.
International Search Report and Written Opinion for International Application No. PCT/US2008/001549, mailed May 16, 2008, 7 pages.
International Search Report and Written Opinion for International Application No. PCT/US2014/033317, mailed Aug. 25, 2014, 16 pages.
International Search Report and Written Opinion for International Application No. PCT/US2014/065669, mailed Jan. 29, 2015, 18 pages.
International Search Report and Written Opinion for International Application No. PCT/US2015/036693, mailed Oct. 16, 2015, 9 pages.
International Search Report and Written Opinion for International Application No. PCT/US2015/041709, mailed Oct. 23, 2015, 9 pages.
International Search Report and Written Opinion for International Application No. PCT/US2015/041714, mailed Oct. 30, 2015, 10 pages.
International Search Report and Written Opinion for International Application No. PCT/US2016/032123, mailed Oct. 17, 2016, 12 pages.
International Search Report and Written Opinion for International Application No. PCT/US2017/015237, mailed Apr. 5, 2017, 10 pages.
International Search Report and Written Opinion for International Application No. PCT/US2017/065270, mailed Apr. 13. 2018, 12 pages.
International Search Report and Written Opinion for International Application No. PCT/US2018/063980, mailed Feb. 14, 2019, 9 pages.
International Search Report and Written Opinion for International Application No. PCT/US2019/037015, mailed Oct. 1, 2019, 10 pages.
International Search Report and Written Opinion for International Application No. PCT/US2021/051647, mailed Dec. 13, 2021, 7 pages.
International Search Report and Written Opinion for International Application No. PCT/US2023/060033 mailed Jul. 7, 2023, 17 pages.
Intlekofer A.M., et al., "At the Bench: Preclinical Rationale for CTLA-4 and PD-1 Blockade as Cancer Immunotherapy," Journal of Leukocyte Biology, Jul. 2013, vol. 94 (1), pp. 25-39.
Invitation to Pay Additional Fees for International Application PCT/US2023/060033, mailed Mar. 30, 2023, 2 pages.
Isfort, C. S. et al., "Helical Complexes Containing Diamide-Bridged Benzene-o-dithiolato/Catecholato Ligands," Chemistry-A European Journal, vol. 13, Issue 8, Mar. 2007, pp. 2344-2357.
Ishida, Y. et al., Treatment of myeloid leukemic cells with the phosphatase inhibitor okadaic acid induces cell cycle arrest at either G1/S or G2/M depending on dose. J Cell Physiol 150:484-492 (1992).
Ito, T. et al. (2021). Paralog knockout profiling identifies DUSP4 and DUSP6 as a digenic dependence in MAPK pathway-driven cancers. Nature Genetics, 53(12): 1664-1672. https://doi.org/10.1038/s41588-021-00967-z.
Jain, G. et al., "Theory and Practice of Physical Pharmacy," Elsevier India, 1st Ed. E-Book, Jan. 2013, pp. 150-154, ISBN: 9788131232651.
Janssens, V. et al., "PP2A Holoenzyme Assembly: In Cauda Venenum (The Sting Is in the Tail)," Trends in Biochemical Sciences, 2008, vol. 33, No. 3, pp. 113-121.
Janssens, V. et al., Review Article: Protein phosphatase 2A: a highly regulated family of serine/threonine phosphatases implicated in cell growth and signalling. Biochem. J., 353(Pt 3):417-439 (Feb. 2001).

Janssens, V. et al., "The Role and Therapeutic Potential of Ser/Thr Phosphatase PP2A in Apoptotic Signalling Networks in Human Cancer Cells," Current Molecular Medicine, 2012, vol. 12, No. 3, pp. 268-287.
Jia, D. et al., "Elucidating the Metabolic Plasticity of Cancer: Mitochondrial Reprogramming and Hybrid Metabolic States," Cells, 7, 21 (2018), 19 pages.
Jin, H. et al.,. EGFR activation limits the response of liver cancer to lenvatinib. Nature. Jul. 2021, 595(7869):730-734.
Jin, N. et al., "Identification of metabolic vulnerabilities of receptor tyrosine kinases-driven cancer," Nature Communications, 10:2701 (2019), 15 pages.
Johansson H., et al., "Immune Checkpoint Therapy for Pancreatic Cancer," World Journal of Gastroenterology, Nov. 21, 2016, vol. 22 (43), pp. 9457-9476.
Johnson et al., Plk1 activation by Ste20-like kinase (Slk) phosphorylation and polo-box phosphopeptide binding assayed with the substrate translationally controlled tumor protein (TCTP), Biochemistry, vol. 47, No. 12, Mar. 2008 (pp. 3688-3696).
Johnstone, R. W. et al., Apoptosis: a link between cancer genetics and chemotherapy. Cell, 108:153-164 (Jan. 2002).
Joshi et al., "Retinoic acid receptors and tissue-transglutaminase mediate short-term effect of retinoic acid on migration and invasion of neuroblastoma SH-SY5Y cells," Oncogene, vol. 25, No. 2, Jan. 2006 (pp. 240-247).
Junttila, M. R. et al., "CIP2A inhibits PP2A in human malignancies," Cell, vol. 130, No. 1, Jul. 2007, pp. 51-62.
Kalev, P. et al., "Loss of PPP2R2A inhibits homologous recombination DNA repair and predicts tumor sensitivity to PARP inhibition," Cancer Research, vol. 72, No. 24, Dec. 2012, pp. 6414-6424.
Kamat, P. K. et al., Molecular and cellular mechanism of okadaic acid (OKA)-induced neurotoxicity: a novel tool for Alzheimer's disease therapeutic application. Mol. Neurobiol 50:852-865 (2014).
Kamitani et al., "Histone acetylation may suppress human glioma cell proliferation when p21 WAF/Cip1 and gelsolin are induced," Neuro-Oncology, vol. 4, No. 2, Apr. 2002 (pp. 95-101).
Kang, D. E. et al., "Presenilins mediate phosphatidylinositol 3-kinase/AKT and ERK activation via select signaling receptors," The Journal of Biological Chemistry, vol. 280, No. 36, Sep. 2005, pp. 31537-31547.
Kantarjian, H. et al., "Proposal for a new risk model in myelodysplastic syndrome that accounts for events not considered in the original International Prognostic Scoring System," Cancer, 113(6):1351-1361 (Sep. 2008).
Kanteti, R. et al., "MET and PI3K/mTOR as a potential combinatorial therapeutic target in malignant pleural mesothelioma," PLoS ONE, 9(9):e105919 (2014), 16 pages.
Karras, D. J. et al., Poisoning from "Spanish Fly" (Cantharidin). Am J Emerg Med 14:478-483 (1996).
Kato, T. et al., "Overexpression of MAD2 predicts clinical outcome in primary lung cancer patients," Lung Cancer, vol. 4, No. 1, Oct. 2011, pp. 124-131.
Katsushima, K. et al., Non-coding RNAs as epigenetic regulator of glioma stem-like cell differentiation. Frontiers in Genetics, vol. 5, Article 14, (Feb. 2014), 8 pages.
Kauko, O. et al., Non-genomic mechanisms of protein phosphatase 2A (PP2A) regulation in cancer. Int J Biochem Cell Biol 96, 157-164 (2018).
Kawada, I. et al., Paxillin mutations affect focal adhesions and lead to altered mitochondrial dynamics: relevance to lung cancer. Cancer Biol Ther 14, 679-691 (2013).
Kawamura et al., "Endothall thioanhydride: structural aspects of unusually high mouse toxicity and specific binding site in liver," Chemical Research in Toxicology, vol. 3, No. 4, Jul. 1990 (pp. 318-324).
Kayser et al., "Metal hydride reductions of unsymmetrical cyclic anhydrides. The importance of the antiperiplanar effect on the regioselectivity of these reactions," Canadian Journal of Chemistry, vol. 60, No. 10, May 1982 (pp. 1192-1198).
Kayser et al., "On the regioselectivity of Wittig reactions with unsymmetrically substituted succinic anhydrides," Canadian Journal of Chemistry, vol. 67, No. 9, Sep. 1989 (pp. 1401-1410).

(56) References Cited

OTHER PUBLICATIONS

Kaytor, M. D. et al., "The GSK3β signaling cascade and neurodegenerative disease," vol. 12, (2002), pp. 275-278.

Kazi, A. et al. (2018), "GSK3 suppression upregulates β-catenin and c-Myc to abrogate KRas-dependent tumors," Nature Communications, vol. 9, No. 1, 9 pages.

Kelland, L., "The resurgence of platinum-based cancer chemotherapy," Nature Reviews Cancer, Aug. 2007, vol. 7, No. 8, pp. 573-584.

Kelly, W.K., et al., "Drug insight: Histone deacetylase inhibitors—development of the new targeted anticancer agent suberoylanilide hydroxamic acid", Nat ClinPract Oncol. (2005), 2(3): 150-157.

Kent, L. N. et al. (Jun. 2019), "The broken cycle: E2F dysfunction in cancer," Nat Rev Cancer, vol. 19, pp. 326-338. https://doi.org/10.1038/s41568-019-0143-7.

Keytruda Prescribing Information, Merck Sharp & Dohme Corp., FDA Approved Labeling, Reference ID: 3621876, 2014, 16 Pages, Retrieved from the Internet: URL: www.accessdata.fda.gov/drugsatfda_docs/label/2014/125514lbl.pdf.

Kiely M., et al., "PP2A: The Wolf in Sheep's Clothing?," Cancers (Basel), 2015, vol. 7, pp. 648-669.

Kijima, M., et al., "Trapoxin, an antitumor cyclic tetrapeptide, is an irreversible inhibitor of mammalian histone deacetylase," Journal of Biological Chemistry, vol. 268, No. 30, Oct. 1993 (pp. 22429-22435).

Kilari, D. et al., Role of copper transporters in platinum resistance. World J Clin Oncol 7, 106-113 (2016).

Kim et al., "Selective Induction of cyclin-Dependent Kinase Inhibitors and Their Roles in Cell Cycle Arrest Caused by Trichostatin A, an Inhibitor of Histone Deacetylase," Annals of the New York Academy of Sciences, vol. 886, Dec. 1999 (pp. 200-203).

Kim et al., "Susceptibility and radiosensitization of human glioblastoma cells to trichostatin A, a histone deacetylase inhibitor," International Journal of Radiation Oncology, Biology, Physics, vol. 59, No. 4, Jul. 2004 (pp. 1174-1180).

Kim, H. Y. et al., "Molecularly Targeted Therapies for Hepatocellular Carcinoma: Sorafenib as a Stepping Stone," Digestive Diseases, vol. 29, No. 3, Aug. 2011, pp. 303-309.

Kim, Y. et al., "MAD2 and CDC20 are upregulated in high-grade squamous intraepitheliallesions and squamous cell carcinomas of the uterine cervix," International Journal of Gynecological Pathology, vol. 33, No. 5, Sep. 2014, pp. 517-523.

King, F. D. et al., "Bioisosteres, Conformational Restriction and Pro-drugs—Case History: An Example of a Conformational Restriction Approach," Medicinal Chemistry: Principles and Practice, vol. 1994, Chapter 14, pp. 206-209.

Kingwell K., "Cancer: Live Screening of Immunotherapy Targets," Nature Reviews Drug Discovery, Apr. 2014, vol. 13, 1 Page.

Kirsch, D. G. et al., Tumor-suppressor p53: implications for tumor development and prognosis. J Clin Oncol 16:3158-3168 (1998).

Kitamura, K. et al. (Mar. 2000), "Histone deacetylase inhibitor but not arsenic trioxide differentiates acute promyelocytic leukaemia cells with t(11;17) in combination with all-trans retinoic acid," British Journal of Haematology, vol. 108, No. 4, pp. 696-702.

Kok, S-H et al., "Norcantharidin-induced apoptosis in oral cancer cells is associated with an increase of proapoptotic to antiapoptotic protein ratio," Cancer Letters, vol. 217, No. 1, Jan. 2005, pp. 43-52.

Komrokji, R. S. et al., "Role of Lenalidomide in the Treatment of Myelodysplastic Syndromes," Seminars in Oncology, Oct. 2011, vol. 38, No. 5, pp. 648-657.

Kong, A. et al., "WEE1 Inhibitor: Clinical Development," Curr Oncol Rep., 23(9):107, Jul. 2021, 8 pages. doi: 10.1007/s11912-021-01098-8.

Kopetz, S et al. (2019). Encorafenib, Binimetinib, and Cetuximab in BRAF V600E-Mutated Colorectal Cancer. New England Journal of Medicine, 381(17):1632-1643. https://doi.org/10.1056/nejmoa1908075.

Korotkevich, G. et al. (Jun. 2016), "Fast gene set enrichment analysis," Version 3, doi: https://doi.org/10.1101/060012, 40 pages.

Korzus et al., "CBP histone acetyltransferase activity is a critical component of memory consolidation," Neruon, vol. 42, No. 6, Jun. 2004 (pp. 961-972).

Kotsantis, P. et al. (May 2018), "Mechanisms of oncogene-induced replication stress: Jigsaw falling into place," Cancer Discov., vol. 8, No. 5, pp. 537-555. doi: 10.1158/2159-8290.CD-17-1461.

Koukourakis, M. I. et al.,"Concurrent twice-a-week docetaxel and radiotherapy a dose escalation trial with immunological toxicity evaluation," International Journal of Radiation Oncology, Biology, Physics, vol. 43, No. 1, Jan. 1999, pp. 107-114.

Kouno, T. et al., "Standardization of the body surface area (BSA) formula to calculate the dose of anticancer agents in Japan," Jpn J. Clin. Oncol., Jun. 2003, vol. 33, No. 6, pp. 309-313.

Kovach et al., "Enhancement of the antiproliferative activity of human interferon by polyamine depletion," Cancer Treatment Reports, vol. 69, No. 1, Jan. 1985 (pp. 97-103).

Kovalchuk, O. et al., Involvement of microRNA-451 in resistance of the MCF-7 breast cancer cells to chemotherapeutic drug doxorubicin. Mol. Cancer Ther., 7:2152-2159 (2008).

Kozikowski et al., "Functional differences in epigenetic modulators—superiority of mercaptoacetamide-based histone deacetylase inhibitors relative to hydroxamates in cortical neuron neuroprotection studies," Journal of Medicinal Chemistry, vol. 50, No. 13, Jun. 2007 (pp. 3054-3061).

Krasinska, L. et al. (2011). Protein phosphatase 2A controls the order and dynamics of cell-cycle transitions. Molecular Cell, 44(3):437-450. https://doi.org/10.1016/j.molcel.2011.10.007.

Kreickmann, T. et al., "Metallosuprarnolecular Chemistry with Bis (benzene-o-dithiolato) Ligands," J. Am. Chem. Soc., vol. 128, No. 36, 2006, pp. 11808-11819.

Kulasekararaj, A. G. et al., "TP53 mutations in myelodysplastic syndrome are strongly correlated with aberrations of chromosome 5, and correlate with adverse prognosis," Br J Haematol, vol. 160, No. 5, pp. 660-672 (Jan. 2013).

Kumar, M. S. et al., "Coordinate loss of a microRNA and protein-coding gene cooperate in the pathogenesis of 5q-syndrome," Blood, vol. 118, No. 17, pp. 4666-4673 (Oct. 2011).

Kuo, J-H et al., "Cantharidin induces apoptosis in human bladder cancer TSGH 8301 cells through mitochondria-dependent signal pathways," Int. J. Oncol., (2010) vol. 37, pp. 1243-1250.

Kurebayashi et al., "Expression levels of estrogen receptor-alpha, estrogen receptor-beta, coactivators, and corepressors in breast cancer," Clinical Cancer Research, vol. 6, No. 2, Feb. 2000 (pp. 512-518).

Kwon, H.J., et al., "Depudecin induces morphological reversion of transformed fibroblasts via the inhibition of histone deacetylase," Proceedings of the National Academy of Sciences U.S.A., vol. 95, No. 7, Mar. 1998 (pp. 3356-3361).

Langley et al., "Pulse inhibition of histone deacetylases induces complete resistance to oxidative death in cortical neurons without toxicity and reveals a role for cytoplasmic p21(waf1/cip1) in cell cycle-independent neuroprotection," Journal of Neuroscience, vol. 28, No. 1, Jan. 2008 (pp. 163-176).

Larive, S. et al., "Carboplatin-etoposide combination in small cell lung cancer patients older than 70 years: a phase II trial," Lung Cancer, 2002;35(1):1-7.

Larkin, J. et al., "Combined Nivolumab and Ipilimumab or Monotherapy in Untreated Melanoma," New England Journal of Medicine, Jul. 2015, 373(1), pp. 23-34.

Latchman, Y., et al., "PD-L2 is a second ligand for PD-1 and inhibits T cell activation", Nature Immunology (2001); 2(3): 261-268.

Lavinsky et al., "Diverse signaling pathways modulate nuclear receptor recruitment of N-CoR and SMRT complexes," Proceedings of the National Academy of Sciences U.S.A., vol. 95, No. 6, Mar. 1998 (pp. 2920-2925).

Le L.H., et al., "Phase I and Pharmacokinetic Study of Fostriecin Given as an Intravenous Bolus Daily for Five Consecutive Days," Investigational New Drugs, 2004, vol. 22, pp. 159-167.

Lecarpentier, Y. et al. (Nov. 2019), "Multiple Targets of the Canonical WNT/β-Catenin Signaling in Cancers," Frontiers in Oncology, vol. 9, Article 1248, 7 pages. https://doi.org/10.3389/fonc.2019.01248.

(56) References Cited

OTHER PUBLICATIONS

Lecca S., et al., "Rescue of GABAB and GIRK Function in the Lateral Habenula by Protein Phosphatase 2A Inhibition Ameliorates Depression-Like Phenotypes in Mice," Nature Medicine, Mar. 2016, vol. 22 (3), pp. 254-261.

Lee, M-O et al., Role of Coactivators and Corepressors in the Induction of the RARbeta gene in human colon cancer cells Biological and Pharmaceutical Bulletin, vol. 25, No. 10, (2002), pp. 1298-1302.

Lee, Y. S. et al., MicroRNAs in cancer. Annu. Rev. Pathol. Mech. Dis., 4:199-227 (2009).

Lei et al., "Plk1 depletion in nontransformed diploid cells activates the DNA-damage checkpoint," Oncogene, vol. 27, No. 28, Jun. 2008 (pp. 3935-3943).

Lerga, A. et al., Apoptosis and mitotic arrest are two independent effects of the protein phosphatases inhibitor okadaic acid in K562 leukemia cells. Biochem Biophys Res Commun 260:256-264 (1999).

Levenson et al., "Regulation of histone acetylation during memory formation in the hippocampus," Journal of Biological Chemistry, vol. 279, No. 39, Sep. 2004 (pp. 40545-40559).

Levesque, D., "Reduction of L-DOPA-induced dyskinesias by retinoid agonists: a new way to improve Parkinson's disease treatment," The Parkinson Alliance, 2004 Pilot Study Grants (abstract), 6 pages.

Li et al., "Valproic acid induces growth arrest, apoptosis, and senescence in medulloblastomas by increasing histone hyperacetylation and regulating expression of p21Cip1, CDK4, and CMYC," Molecular Cancer Therapeutics, vol. 4, No. 12, Dec. 2005 (pp. 1912-1922).

Li, F. et al., "CHK1 Inhibitor Blocks Phosphorylation of FAM122A and Promotes Replication Stress," Molecular Cell, vol. 80, Nov. 2020, with Supplemental Information, 35 pages.

Li, L. et al., "Combination analysis of Bub1 and Mad2 expression in endometrial cancer: act as a prognostic factor in endometrial cancer," Archives of Gynecology and Obstetrics, vol. 288, No. 1, Jul. 2013 pp. 155-165.

Li, W. et al., Cantharidin, a potent and selective PP2A inhibitor, induces an oxidative stress-independent growth inhibition of pancreatic cancer cells through G2/M cell-cycle arrest and apoptosis. Cancer Sci. 101:1226-1233 (2010).

Li, Y-M et al., "Cantharidin-binding protein: identification as protein phosphatase 2A," Proc Natl Acad Sci USA, vol. 89, No. 24, pp. 11867-11870 (Dec. 1992).

Li Y-M., et al., "Protein Phosphatase 2A and its [3H]Cantharidin/[3H]Endothall Thioanhydride Binding Site, Inhibitor Specificity of Cantharidin and ATP Analogues," Biochemical Pharmacology, Oct. 1993, vol. 46 (8), pp. 1435-1443.

Li, Z. et al., Up-regulation of a HOXA-PBX3 homeobox-gene signature following down-regulation of miR-181 is associated with adverse prognosis in patients with cytogenetically abnormal AML. Blood, 119(10):2314-2324 (Mar. 2012).

Lim, K-H. et al., "Tumour maintenance is mediated by eNOS," Nature, vol. 452, Apr. 2008, pp. 646-649.

Lim, Z. et al., "Allogeneic Hematopoietic Stem-Cell Transplantation for Patients 50 Years or Older with Myelodysplastic Syndromes or Secondary Acute Myeloid Leukemia," Journal of Clinical Oncology, vol. 28, No. 3, pp. 405-411 (Jan. 2010).

Lin et al., "Role of the histone deacetylase complex in acute promyelocytic leukaemia," Nature, vol. 391, No. 6669, Feb. 1998 (pp. 811-814).

Lindqvist, A. et al. (2009). The decision to enter mitosis: feedback and redundancy in the mitotic entry network. Journal of Cell Biology, vol. 185, Issue 2, pp. 193-202. https://doi.org/10.1083/jcb.200812045.

List, A. et al., "Efficacy of lenalidomide in myelodysplastic syndromes," N Engl J Med, vol. 352, No. 6, pp. 549-557 (Feb. 2005).

List, A. et al., "Lenalidomide in the Myelodysplastic Syndrome with Chromosome 5q Deletion," The New England Journal of Medicine, Oct. 2006, vol. 355, No. 14, pp. 1456-1465.

List, A. F. et al., "Extended survival and reduced risk of AML progression in erythroid-responsive lenalidomide-treated patients with lower-risk del(5q) MDS," Leukemia, vol. 28, No. 5, pp. 1033-1040 (May 2014).

List, A. F. et al., "Lenalidomide (CC-5013; Revlimid(R)) Promotes Erythropoiesis in Myelodysplastic Syndromes (MDS) by CD45 Protein Tyrosine Phosphatase (PTP) Inhibition," ASH Annual Meeting Abstracts, Blood, 108:1360 (2006) (Abstract), 2 pages.

List, A. F. et al., "Lenalidomide: targeted anemia therapy for myelodysplastic syndromes," Cancer Control, vol. 13, Supplement, pp. 4-11 (Dec. 2006).

Littler, S. et al. (Jul. 2019), "Oncogenic MYC amplifies mitotic perturbations," Open Biol. vol. 9:190136, 20 pages. http://dx.doi.org/10.1098/rsob.190136.

Liu, C-Y et al., Tamoxifen induces apoptosis through cancerous inhibitor of protein phosphatase 2A-dependent phospho-Akt inactivation in estrogen receptor-negative human breast cancer cells. Breast Cancer Research 16:431 (2014), 15 pages.

Liu, D. et al., "The effects of cantharidin and cantharidin derivates on tumour cells," Anti-Cancer Agents in Medicinal Chemistry, vol. 9, No. May 2009, pp. 392-396.

Liu et al., "Normal cells, but not cancer cells, survive severe Plk1 depletion," Molecular and Cellular Biology, vol. 26, No. 6, Mar. 2006 (pp. 2093-2108).

Liu et al., "Stabilization and enhancement of the antiapoptic activity of Mcl-1 by TCTP," Molecular and Cellular Biology, vol. 25, No. 8, Apr. 2005 (pp. 3117-3126).

Liu, F. et al., "The inhibition of glycogen synthase kinase 3β by a metabotropic glutamate receptor 5 mediated pathway confers neuroprotection to Aβ peptides," Journal of Neurochemistry, vol. 95, No. 5, (2005) pp. 1363-1372.

Liu, G. P. et al., Silencing PP2A inhibitor by lenti-shRNA interference ameliorates neuropathologies and memory deficits in tg2576 mice. Mol Ther. 2013;21(12):2247-2257.

Liu, L. et al., Inhibition of Protein Phosphatase 2A Sensitizes Mucoepidermoid Carcinoma to Chemotherapy via the PI3K-AKT Pathway in Response to Insulin Stimulus. Cell Physiol Biochem 50, 317-331 (2018).

Llovet et al. "Sorafenib in advanced hepatocellular carcinoma", N Engl J Med 2008; 359:378-90.

Longacre, L. S. et al., "New Horizons in Cardioprotection. Recommendations From the 2010 National Heart, Lung, and Blood Institute Workshop," Circulation, vol. 124, No. 10, Sep. 2011, pp. 1172-1179.

Lopez-Pajares et al., "Phosphorylation of MDMX mediated by Akt leads to stabilization and induces 14-3-3 binding," Journal of Biological Chemistry, vol. 283, No. 20, May 2008 (pp. 13707-13713).

Love, M. I. et al. (2014), "Moderated estimation of fold change and dispersion for RNA-seq data with DESeq2," Genome Biology, vol. 15:550, 21 pages. DOI 10.1186/s13059-014-0550-8.

Lu, F. et al., "miR-181b increases drug sensitivity in acute myeloid leukemia via targeting HMGB1 and Mcl-1," Int J Oncol. 2014; 45(1):383-392.

Lu, J. et al., "Inhibition of serine/threonine phosphatase PP2A enhances cancer chemotherapy by blocking DNA damage induced defense mechanisms," PNAS, vol. 106, No. 28, pp. 11697-11702 (Jul. 2009).

Lu, J. et al. (May 2008), "LB-1, an inhibitor of serine-threonine protein phosphatase PP2A, suppresses the growth of glioblastoma cells in vitro and in vivo," Cancer Research, vol. 68, Issue 9 Supplement, Abstract 5693, 99th AACR Annual Meeting, Apr. 12-16, 2008; San Diego, CA, 4 pages.

Lu, J. et al., "The effect of a PP2A inhibitor on the nuclear receptor corepressor pathway in glioma," J Neurosurg, vol. 113, No. 2, pp. 225-233 (Aug. 2010).

Lu, S., et al., "Aqueous ring-opening metathesis polymerization and copolymerization of 2,3-dicarboxylic acid anhydride, 2,3-bis(methoxymethyl) and 2,3-dicarboxylic acid monomethyl ester derivatives of 7-oxanorbornene," European Polymer Journal, vol. 29, No. 2-3, Feb.-Mar. 1993 (pp. 269-279).

(56) References Cited

OTHER PUBLICATIONS

Lu, S., et al., "Aqueous ring-opening metathesis polymerization of 7-oxanorbornene derivatives with oxygen-containing functionalities," Macromolecular Chemistry and Physics, vol. 195, No. 4, Apr. 1994 (pp. 1273-1288).

Luchenko, V. L. et al., "Schedule-dependent synergy of histone deacetylase inhibitors with DNA damaging agents in small cell lung cancer," Cell Cycle, vol. 10, No. 18, (2011) pp. 3119-3128.

Luo, J. et al. (2009). Principles of Cancer Therapy: Oncogene and Non-oncogene Addiction the Current State of Cancer Research. Cell, 136(5):823-837. https://doi.org/10.1016/j.cell.2009.02.024.

Luserna di Rorà, A. G. et al. (2020). A WEE1 family business: Regulation of mitosis, cancer progression, and therapeutic target. Journal of Hematology and Oncology, vol. 13, Issue 1, 17 pages. https://doi.org/10.1186/s13045-020-00959-2.

Lv, P. et al., "Inhibition of protein phosphatase 2A with a small molecule LB100 radiosensitizes nasopharyngeal carcinoma xenografts by inducing mitotic catastrophe and blocking DNA damage repair," Oncotarget. 5(17):7512-7524 (Jul. 2014).

Ma, L. et al., "Metabolic Symbiosis in Chemoresistance: Refocusing the Role of Aerobic Glycolysis," Front Oncol., vol. 10, Article 5 (Jan. 2020), 8 pages.

Ma, P. C. et al., Expression and mutational analysis of MET in human solid cancers. Genes Chromosomes Cancer 47, 1025-1037 (2008).

Maggio, D. et al., "Inhibition of protein phosphatase-2A with LB-100 enhances antitumor immunity against glioblastoma," Journal of Neuro-Oncology, 148(2):231-244 (Jun. 2020) and Supplementary Material, 28 pages.

Maghfoor, I. et al., "Lung cancer," Ann Saudi Med. 2005;25(1):1-12.

Maillet, M. et al. (2008). DUSP6 (MKP3) null mice show enhanced ERK1/2 phosphorylation at baseline and increased myocyte proliferation in the heart affecting disease susceptibility. Journal of Biological Chemistry, 283(45):31246-31255. https://doi.org/10.1074/jbc.M806085200.

Mallo, M. et al., "Impact of adjunct cytogenetic abnormalities for prognostic stratification in patients with myelodysplastic syndrome and deletion 5q," Leukemia, vol. 25, No. 1, pp. 110-120 (Jan. 2011).

Mangan et al, "Turning Back the Clock on Neurodegeneration," Cell, vol. 129, No. 5, Jun. 2007 (pp. 851-853).

Manka, J.T., et al., "Retro Diels-Alder Reactions of 5,6-Disbustituted-7-oxabicyclo[2.2.1]hept-2-enes: Experimental and Density Functional Theory Studies," Journal of Organic Chemistry, vol. 65, No. 17, Aug. 2000 (pp. 5202-5206).

Marcucci, G. et al., MicroRNA expression in cytogenetically normal acute myeloid leukemia. N Engl J Med 358:1919-1928 (2008).

Marcucci, G. et al., Phase 1 and pharmacodynamic studies of G3139, a Bcl-2 antisense oligonucleotide, in combination with chemotherapy in refractory or relapsed acute leukemia. Blood, 101:425-432 (2003).

Marcucci, G. et al., Prognostic significance of, and gene and microRNA expression signatures associated with, CEBPA mutations in cytogenetically normal acute myeloid leukemia with high-risk molecular features: a Cancer and Leukemia Group B Study. J. Clin. Oncol. 26(31):5078-5087 (Nov. 2008).

Mardor et al., "Monitoring response to convection-enhances taxol delivery in brain tumor patients using diffusion-weighted magnetic resonance imaging," Cancer Research, vol. 61, No. 13, Jul. 2001 (pp. 4971-4973).

Marks et al., "Histone deacetylases," Current Opinion in Pharmacology, vol. 3, No. 4, Aug. 2003 (pp. 344-351).

Martiniova, L. et al., "Pharmacologic Modulation of Serine/Threonine Phosphorylation Highly Sensitizes PHEO in a MPC Cell and Mouse Model to Conventional Chemotherapy," PLoS ONE, Feb. 2011, vol. 6, No. 2, e14678, 8 pages.

Martinou, J-C et al., Breaking the mitochondrial barrier. Nat Rev Mol Cell Biol 2:63-67 (Jan. 2001).

Matsuzawa et al., "Endothal and cantharidin analogs: relation of structure to herbicidal activity and mammalian toxicity," Journal of Agricultural and Food Chemistry, vol. 35, No. 5, Sep. 1987 (pp. 823-829).

Matthay et al., "Treatment of High-Risk Neuroblastoma and Intensive Chemotherapy, Radiotherapy, Autologous Bone Marrow Transplantation, and 13-cis-Retinoic Acid," New England Journal of Medicine, vol. 341, Oct. 1999 (pp. 1165-1173).

Mazhar, S. et al., "Targeting PP2A in cancer: Combination therapies," Biochim. Biophys Acta Mol Cell Res. Jan. 2019; 1866(1):51-63.

McCluskey, A. et al., "Anhydride modified cantharidin analogues. Is ring opening important in the inhibition of protein phosphatase 2A?," European Journal of Medicinal Chemistry, vol. 35, No. 10, Oct. 2000, pp. 957-964.

McCluskey, A. et al., "Anhydride modified cantharidin analogues: synthesis, inhibition of protein phosphatases 1 and 2A and anticancer activity," Bioorganic & Medicinal Chemistry Letters, vol. 10, No. 15, Aug. 2000, pp. 1687-1690.

McCluskey, A. et al., "Inhibition of Protein Phosphatase 2A by Cantharidin Analogues," Bioorganic and Medicinal Chemistry Letters, vol. 6, No. 9, May 1996, pp. 1025-1028.

McDaniel, J. M. et al., "Reversal of T-cell Tolerance in Myelodysplastic Syndrome through Lenalidomide Immune Modulation," Leukemia, Jun. 2012, vol. 26, No. 6, pp. 1425-1429.

McDaniel, J. M., "Lenalidomide Targets the T-Cell Co-Stimulatory Pathway to Mediate Immune Modulation," Graduate Thesis and Dissertations, University of South Florida, Scholar Commons, Jan. 2012, 191 pages.

McGraw, K. L. et al., "Lenalidomide induces lipid raft assembly to enhance erythropoietin receptor signaling in myelodysplastic syndrome progenitors," PLoS One, 9(12):e114249 (Dec. 2014), 18 pages.

Mehta, R. S., "Dose-Dense and/or Metronomic Schedules of Specific Chemotherapies Consolidate the Chemosensitivity of Triple-Negative Breast Cancer: A Step Toward Reversing Triple-Negative Paradox," Journal of Clinical Oncology, vol. 26, No. 19, Jul. 2008, pp. 3286-3288.

Melero I., et al., "T-Cell and NK-Cell Infiltration into Solid Tumors: A Key Limiting Factor for Efficacious Cancer Immunotherapy," Cancer Discovery, May 2014, vol. 4, pp. 522-526.

Meng, F. et al., "EGFL9 promotes breast cancer metastasis by inducing cMET activation and metabolic reprogramming," Nature Communications, 10:5033 (2019), 17 pages.

Meske, V. et al., "Coupling of Mammalian Target of Rapamycin with Phosphoinositide 3-Kinase Signaling Pathway Regulates Protein Phosphatase 2A- and Glycogen Synthase Kinase-3beta-dependent Phosphorylation of Tau," vol. 283, No. 1, Jan. 2008, pp. 100-109.

Mi, S. et al., MicroRNA expression signatures accurately discriminate acute lymphoblastic leukemia from acute myeloid leukemia. Proc Natl Acad Sci USA, 104(50):19971-19976 (Dec. 2007).

Mielnicki et al., "Epigenetic regulation of gelsolin expression in human breast cancer cells," Experimental Cell Research, vol. 249, No. 1, May 1999 (pp. 161-176).

Millar, J. et al., cdc25 M-phase inducer. Cold Spring Harbor Symposia on Quantitative Biology, 56:577-584 (1991).

Millward, T. A. et al., Regulation of protein kinase cascades by protein phosphatase 2A. Trends Biochem Sci. 24:186-191 (May 1999).

Mirzaei, H. R. et al., "Chimeric Antigen Receptors T Cell Therapy in Solid Tumor: Challenges and Clinical Applications," Front Immunol, Dec. 2017, vol. 8 Article 1850, 13 pages.

Mirzapoiazova, T. et al., HABP2 is a Novel Regulator of Hyaluronan-Mediated Human Lung Cancer Progression. Front Oncol., vol. 5, Article 164 (Jul. 2015), 12 pages.

Mirzapoiazova, T. et al., "Protein Phosphatase 2A as a Therapeutic Target in Small Cell Lung Cancer," Molecular Cancer Therapeutics, 2021, 20(10):1820-1835.

Momparler, R. L. (1980), "In vitro systems for evaluation of combination chemotherapy," Pharmacol. Ther., vol. 8, No. 1, pp. 21-35.

(56) References Cited

OTHER PUBLICATIONS

Moore, C. D. et al., "Immunotherapy in Cancer Treatment: A Review of Checkpoint Inhibitors," U.S. Pharmacist, 2018, vol. 43, No. 2, pp. 27-31.
Morse et al., "Docetaxel induces cell death through mitotic catastrophe in human breast cancer cells," Molecular Cancer Therapeutics, vol. 4, No. 10, Oct. 2005 (pp. 1495-1504).
Mumby, M., "PP2A: Unveiling A Reluctant Tumor Suppressor," Cell, Jul. 2007, vol. 130, pp. 21-24.
Munster, P. N. et al., "Phase I trial of vorinostat and doxorubicin in solid tumors: histone deacetylase 2 expression as a predictive marker," British Journal of Cancer, vol. 101, (2009) pp. 1044-1050.
Musacchio, A. et al., "The spindle-assembly checkpoint in space and time," Nature Reviews, Molecular Cell Biology, vol. 8, No. 5, May 2007, pp. 379-393.
Muzny, D. M. et al. (2012). Comprehensive molecular characterization of human colon and rectal cancer. Nature, 487(7407):330-337. https://doi.org/10.1038/nature11252.
Myers, E. et al., "Associations and Interactions between Ets-1 and Ets-2 and Coregulatory Proteins, SRC-1, AIB1, and NCoR in Breast Cancer," Clinical Cancer Research, vol. 11, Mar. 2005, pp. 2111-2122.
Nair and Jacob, "A Simple Practice Guide for Dose Conversion Between Animals and Human," Journal of Basic and Clinical Pharmacy, vol. 7, Issue 2, Mar.-May 2016, pp. 27-31.
Nakano, Y. et al., "Mitotic arrest deficiency 2 induces carcinogenesis in mucinous ovarian tumors," Oncology Letters, vol. 3, No. 2, Feb. 2012, pp. 281-286.
National Library of Medicine—Medical Subject Headings, 2009 MeSH, MeSH Descriptor Data, Phosphoric Monoester Hydrolases, Phosphatases (2009), 2 pages.
Neviani et al., "FTY720, a new alternative for treating blast crisis chronic myelogenous leukemia and Philadelphia chromosome-positive acute lymphocytic leukemia," Journal of Clinical Investigation, vol. 117, No. 9, Sep. 2007 (pp. 2408-2421).
Ngan et al., "Oxaliplatin induces mitotic catastrophe and apoptosis in esophageal cancer cells," Cancer Science, vol. 99, No. 1, Jan. 2008 (pp. 129-139).
Ngiow S.F., et al., "A Threshold Level of Intratumor CD8+ T-cell PD1 Expression Dictates Therapeutic Response to Anti-PD1," Cancer Research, Sep. 15, 2015, vol. 75 (18), pp. 3800-3811.
Niell, H. B. et al., Carboplatin/etoposide/paclitaxel in the treatment of patients with extensive small-cell lung cancer. Clin Lung Cancer. 2001;2(3):204-209.
Niell, H. B. et al., Randomized phase III intergroup trial of etoposide and cisplatin with or without paclitaxel and granulocyte colony-stimulating factor in patients with extensive-stage small-cell lung cancer: Cancer and Leukemia Group B Trial 9732. J Clin Oncol. 2005;23(16):3752-3759.
Nieto, P. et al., A Braf kinase-inactive mutant induces lung adenocarcinoma. Nature. Aug. 2017, 548(7666):239-243.
Nifoussi, S. K. et al., "Inhibition of Protein Phosphatase 2A (PP2A) Prevents Mc1-1 Protein Dephosphorylation and the Thr-163/Ser-159 Phosphodegron, Dramatically Reducing Expression in Mcl-1-amplified Lymphoma Cells," The Journal of Biological Chemistry, Aug. 2014, vol. 289, No. 32, pp. 21950-21959.
Nikaki, A. et al., "Role of microRNAs in gliomagenesis: targeting miRNAs in glioblastoma multiforme therapy," Expert Opin Investig Drugs, 21(10):1475-1488 (Oct. 2012).
Nimer, S. D., "Myelodysplastic Syndromes," Blood, May 2008, vol. 111, No. 10, pp. 4841-4851.
Nobumori, Y. et al., B56gamma tumor-associated mutations provide new mechanisms for B56gamma-PP2A tumor suppressor activity. Mol. Cancer Res. 11(9):995-1003 (2013).
Nogami, K. et al., "Mechanisms of Plasmin-catalyzed Inactivation of Factor VIII a crucial role for proteolytic cleavage at arg336 responsible for plasmin-catalyzed factor VIII inactivation," The Journal of Biological Chemistry, vol. 282, (Feb. 2007), pp. 5287-5295.
Olivier, M. et al. (Sep. 2008), "Recent advances in p53 research: an interdisciplinary perspective," Cancer Gene Therapy, vol. 16, pp. 1-12.
Olmos et al., "Targeting polo-like kinase: learning too little too late?," Journal of Clinical Oncology, vol. 26, No. 34, Dec. 2008 (pp. 5497-5499).
Opdivo Prescribing Information, Bristol-Myers Squibb Company, FDA Approved Labeling, Reference ID:3677021, 2014, 20 Pages, Retrieved from the Internet: URL: www.accessdata.fda.gov/drugsatfdadocs/label/2014/125554lbl.pdf.
Ory, S. et al., Protein phosphatase 2A positively regulates Ras signaling by dephosphorylating KSR1 and Raf-1 on critical 14-3-3 binding sites. Curr Biol 13:1356-1364 (Aug. 2003).
Owonikoko, T. K. et al., "Vorinostate increases carboplatin and paclitaxel activity in non-small cell lung cancer cells," Int. J. Cancer, vol. 126, (2010), pp. 743-755.
Padron, E. et al., "The 5q- Syndrome: Biology and Treatment," Current Treatment Options in Oncology, Dec. 2011, vol. 12, No. 4, pp. 354-368.
Paez, J. G. et al., "PI3K/PTEN/Akt Pathway," Signal Transduction in Cancer, vol. 115, 2006, pp. 145-167.
Pagliarini, R. et al. (2015). Oncogene addiction: pathways of therapeutic response, resistance, and road maps toward a cure. EMBO Reports, 16(3):280-296. https://doi.org/10.15252/embr.201439949.
Park D.M., et al., "N-CoR Pathway Targeting Induces Glioblastoma Derived Cancer Stem Cell Differentiation," Cell Cycle, Feb. 15, 2007, vol. 6 (4), pp. 467-470.
Parry, R. V. et al., "CTLA-4 and PD-1 Receptors Inhibit T-Cell Activation by Distinct Mechanisms," Molecular and Cellular Biology, Nov. 2005, vol. 25, No. 21, pp. 9543-9553.
Parsons, R., "Phosphatases and tumorigenesis," Curr. Opin. Oncol. 10:88-91(1998).
Peng, F. et al., Induction of apoptosis by norcantharidin in human colorectal carcinoma cell lines: involvement of the CD95 receptor/ligand. J Cancer Res Clin Oncol 128:223-230 (2002).
Pepper, C. et al., Bcl-2 antisense oligonucleotides enhance the cytotoxicity of chlorambucil in B-cell chronic lymphocytic leukemia cells. Leukemia & Lymphoma 42(3):491-498 (2001).
Perera, D. et al. (Jul. 2016), "Oncogenic KRAS triggers MAPK-dependent errors in mitosis and MYC-dependent sensitivity to anti-mitotic agents," Scientific Reports, vol. 6:29741, 15 pages. DOI: 10.1038/srep29741.
Perrotti, D. et al., "Targeting A Tumor Suppressor to Suppress Tumor Growth: News and Views on Protein Phosphatase 2A (PP2A) as a Target for Anti-cancer Therapy," The Lancet Oncology, May 2013, vol. 14, No. 6, pp. e229-e238.
Perrotti et al., "Protein phosphatases 2A (PP2A), a drugable tumor suppressor in Ph1(+) leukemias," Cancer and Metastasis Reviews, vol. 27, No. 2, Jun. 2008 (pp. 159-168).
Peruzzi, P. et al., MicroRNA-128 coordinately targets Polycomb Repressor Complexes in glioma stem cells. Neuro-Oncology, 15(9):1212-1224 (2013).
"Phase I Study of LB-100 with Docetaxel in Solid Tumors," ClinicalTrials.gov Identifier: NCT01837667, 2013, 8 Pages, Retrieved from the Internet: URL: https://clinicaltrials.gov/ct2/show/NCT01837667?term=NCT01837667&draw=2&rank=1 [Retrieved on Jan. 3, 2018].
Prados et al., "Phase II Study of Erlotinib Plus Temozolomide During and After Radiation Therapy in Patients with Newly Diagnosed Glioblastoma Multiforme or Gliosarcoma," Journal of Clinical Oncology, vol. 27, No. 4, Feb. 2009 (pp. 579-584).
Prendiville, J. et al., "Therapy for small cell lung cancer using carboplatin, ifosfamide, etoposide (without dose reduction), midcycle vincristine with thoracic and cranial irradiation," Eur J Cancer. 1994;30A(14):2085-2090.
Price et al., "Histone deacetylase inhibitors: an analysis of recent patenting activity," Expert Opinion on Therapeutic Patents, vol. 17, No. 7, Aug. 2007 (pp. 745-765).
Quang C., et al., "LC-MS/MS Method Development and Validation for The Quantification of LB-100 and Endothall Metabolite in Biological Matrices," Poster MP 158, 64th American Society for

(56) References Cited

OTHER PUBLICATIONS

Mass Spectrometry Conference on Mass Spectrometry and Allied Topics, San Antonio, TX, Jun. 6, 2016, 1 page.
Quesnel, B. et al., Methylation of the p15INK4b gene in myelodysplastic syndromes is frequent and acquired during disease progression. Blood 91(8):2985-2990 (Apr. 1998).
Quoix, E. et al., Etoposide phosphate with carboplatin in the treatment of elderly patients with small-cell lung cancer: a phase II study. Ann Oncol. 2001; 12(7):957-962.
Rabik, C. A. et al., Molecular mechanisms of resistance and toxicity associated with platinating agents. Cancer Treat Rev 33, 9-23 (2007).
Rajapaksa, R. et al., Altered oncoprotein expression and apoptosis in myelodysplastic syndrome marrow cells. Blood 88(11):4275-4287 (Dec. 1996).
Ramanarayanan, J. et al., Pro-apoptotic therapy with the oligonucleotide Genasense (oblimersen sodium) targeting Bcl-2 protein expression enhances the biological anti-tumour activity of rituximab. Br J Haematol 127:519-530 (2004).
Ramezanian et al., "A new super-electrophile: alpha(phenylsulfonyl)maleic anhydride," Journal of Organic Chemistry, vol. 54, No. 12, Jun. 1989 (pp. 2852-2854).
Rautio, J., et al., "Prodrugs: design and clinical applications", Nature Reviews Drug Discovery (Mar. 2008); 7: 255-270.
Reed, J. C., Dysregulation of apoptosis in cancer. J Clin Oncol 17:2941-2953 (1999).
Registry (STN) Online, Nov. 16, 1984, CAS registered No. 57958-23-3, Search Date Jan. 16, 2013, 2 pages.
Reid, M. A. et al., "The B55α subunit of PP2A drives a p53-dependent metabolic adaptation to glutamine deprivation," Molecular Cell, vol. 50, No. 2, Apr. 2013, pp. 200-211.
Reynhout, S. et al. (2019). Physiologic functions of PP2A: Lessons from genetically modified mice. Biochimica et Biophysica Acta—Molecular Cell Research, vol. 1866, Issue 1, pp. 31-50. https://doi.org/10.1016/j.bbamcr.2018.07.010.
Richon, V.M., et al., "A class of hybrid polar inducers of transformed cell differentiation inhibits histone deacetylases," Proceedings of the National Academy of Sciences U.S.A., vol. 95, No. 6, Mar. 1998 (pp. 3003-3007).
Ries, V. et al., "Oncoprotein Akt/PKB induces trophic effects in murine models of Parkinson's disease," PNAS, vol. 103, No. 49, Dec. 2006, pp. 18757-18762.
Riester et al., "Histone deacetylase inhibitors—turning epigenic mechanisms of gene regulation into tools of therapeutic intervention in malignant and other diseases," Applied Microbiology and Biotechnology, vol. 75, Jun. 2007 (pp. 499-514).
Rinkenberger et al., "Mcl-1 deficiency results in peri-implantation embryonic lethality," Genes and Development, vol. 14, No. 1, Jan. 2000 (pp. 23-27).
Riordan, F. A. et al., Okadaic acid-induced apoptosis of HL60 leukemia cells is preceded by destabilization of bd-2 mRNA and downregulation of bd-2 protein. FEBS Lett 435:195-198 (1998).
Robert C., et al., "Nivolumab in Previously Untreated Melanoma Without BRAF Mutation," The New England Journal of Medicine, Jan. 22, 2015, vol. 372 (4), pp. 320-330.
Roberts, K. G. et al., Essential requirement for PP2A inhibition by the oncogenic receptor c-KIT suggests PP2A reactivation as a strategy to treat c-KIT+ cancers. Cancer Res., 70(13):5438-5447 (2010).
Robertson, M. J. et al., "Norcantharimide analogues possessing terminal phosphate esters and their anti-cancer activity," Bioorg. Med. Chem., vol. 19, Issue 18, Sep. 2011, pp. 5734-5741.
Rodriguez-Acebes, S. et al. (2018). Uncoupling fork speed and origin activity to identify the primary cause of replicative stress phenotypes. Journal of Biological Chemistry, 293(33):12855-12861. https://doi.org/10.1074/jbc.RA118.003740.
Ronk, H. et al., "Targeting PP2A for cancer therapeutic modulation," Cancer Biol Med., vol. 19, No. 10, Oct. 2022, pp. 1428-1439; doi: 10.20892/j.issn.2095-3941.2022.0330, 12 pages.
Rosenberg, J. E. et al., Atezolizumab in patients with locally advanced and metastatic urothelial carcinoma who have progressed following treatment with platinum-based chemotherapy: a single-arm, multicentre, phase 2 trial. Lancet. 2016;387(10031):1909-1920.
Rossini G.P., et al., "The Toxic Responses Induced by Okadaic Acid Involve Processing of Multiple Caspase Isoforms," Toxicon, 2001, vol. 39, pp. 763-770.
Rubbia-Brandt, L. et al. (2007), "Importance of histological tumor response assessment in predicting the outcome in patients with colorectal liver metastases treated with neo-adjuvant chemotherapy followed by liver surgery," Annals of Oncology, vol. 18, pp. 299-304. 10.1093/annonc/mdl386.
Rubie et al., "Phase II Study of Temozolomide in Relapsed or Refractory high-Risk Neuroblastoma: A Joint Societe Francaise des Cancers del'Enfant and United Kingdom Children Cancer Study Group—New Agents Group Study," Journal of Clinical Oncology, vol. 24, No. 33, Nov. 2006 (pp. 5259-5264).
Rutka et al., "Effect of retinoids on the proliferation, morphology and expression of glial fibrillary acidic protein of an anaplastic astrocytoma cell line," International Journal of Cancer, vol. 42, No. 3, Sep. 1988 (pp. 419-427).
Ruvolo, P. P. et al., A functional role for the B56 alpha-subunit of protein phosphatase 2A in ceramide-mediated regulation of Bcl2 phosphorylation status and function. J. Biol. Chem. 277(25):22847-22852 (Jun. 2002).
Ruvolo, P. P. et al., Phosphorylation of Bcl2 and regulation of apoptosis. Leukemia 15:515-522 (2001).
Sagiv-Barfi I., et al., "Therapeutic Antitumor Immunity by Checkpoint Blockade is Enhanced by Ibrutinib, An Inhibitor of Both BTK and ITK," Proceedings of the National Academy of Sciences of the United States of America, Feb. 17, 2015, vol. 112, pp. E966-E972.
Sahin, M. et al. (2005), "Retinoic acid isomers protect hippocampal neurons from amyloid-β induced neurodegeneration," Neurotoxicity Research, vol. 7, No. 3, pp. 243-250.
Saito et al., "A synthetic inhibitor of deacetylase, MS-27-275, with marked in vivo antitumor activity against human tumors," Proceedings of the National Academy of Sciences U.S.A., vol. 96, No. 8, Apr. 1999 (pp. 4592-4597).
Sakoff et al., "Anticancer Activity and Protein Phosphatase 1 and 2A Inhibition of a New Generation of Cantharidin Analogues," Investigational New Drugs, vol. 20, No. 1, Feb. 2002 (pp. 1-11).
Sakoff, J. A. et al. (2004), "Protein Phosphatase Inhibition: Structure Based Design. Towards New Therapeutic Agents," Current Pharmaceutical Design, vol. 10, No. 10, pp. 1139-1159.
Salgia, R., "Role of c-Met in cancer: emphasis on lung cancer," Semin Oncol., vol. 36, No. 2, Suppl. 1, pp. S52-S58 (Apr. 2009).
Sallman, D. A. et al., "PP2A: The Achilles Heal in MDS with 5q Deletion," Frontiers in Oncology, vol. 4, Article 264, (Sep. 2014), 7 pages.
Sanderson et al., "Plasma pharmacokinetics and metabolism of the histone deacetylase inhibitor trichostatin a after intraperitoneal administration to mice," Drug Metabolism and Disposition, vol. 32, No. 10, Jul. 2004, (pp. 1132-1138).
Sandroni, P., Aphrodisiacs past and present: a historical review. Clin Auton Res 11:303-307 (2001).
Sangodkar, J. et al., "All Roads Lead to PP2A: Exploiting The Therapeutic Potential of This Phosphatase," The Federation of European Biochemical Societies (FEBS) Journal, 2016, vol. 283, pp. 1004-1024.
Schapira, A. H. et al., "Neuroprotection in Parkinson disease: mysteries, myths, and misconceptions," JAMA, vol. 291, No. 3, Feb. 2004, pp. 358-364.
Schmid, P. et al., Atezolizumab and Nab-Paclitaxel in Advanced Triple-Negative Breast Cancer. N Engl J Med. 2018;379(22):2108-2121.
Schmitt, C. A. et al., Genetic analysis of chemoresistance in primary murine lymphomas. Nature Medicine, vol. 6, No. 8, pp. 1029-1035(Sep. 2000).
Schonthal, A. H., Role of serine/threonine protein phosphatase 2A in cancer. Cancer Letters, 170:1-13 (2001).

(56) References Cited

OTHER PUBLICATIONS

Schvartzman J-M., et al., "Mad2 is a Critical Mediator of the Chromosome Instability Observed Upon Rb and p53 Pathway Inhibition," Cancer Cell, Jun. 14, 2011, vol. 19, pp. 701-714.
Schvartzman, J-M et al., "Mitotic chromosomal instability and cancer: mouse modelling of the human disease," Nature Reviews, Cancer, vol. 10, No. 2, Feb. 2010, pp. 102-115.
Schwind, S. et al., Prognostic significance of expression of a single microRNA, miR-181a, in cytogenetically normal acute myeloid leukemia: a Cancer and Leukemia Group B study. J. Clin. Oncol. 28(36):5257-5264 (Dec. 2010).
Science IP, The CAS Search Service, Structure Search of Thiophenols, Sep. 2007, 375 pages.
Seshacharyulu, P. et al., "Phosphatase: PP2A Structural Importance, Regulation and Its Aberrant Expression in Cancer," Cancer Letters, Jul. 2013, vol. 335, No. 1, pp. 9-18.
Shain, A.H. et al. (Jan. 2013) "The spectrum of SWI/SNF mutations, ubiquitous in human cancers" PLOS One, 8(1):e55119, 11 pages.
Shen, D-W et al., "Cisplatin Resistance: A Cellular Self-Defense Mechanism Resulting from Multiple Epigenetic and Genetic Changes," Pharmacological Reviews, vol. 64, No. 3, pp. 706-721 (2012).
Shen, J. et al., "Skeletal and CNS defects in presenilin-1-deficient mice," Cell, vol. 89, Issue 4, May 1997, pp. 629-639.
Sherrington, R. et al., "Cloning of a gene bearing missense mutations in early-onset familial Alzheimer's disease," Nature, vol. 375, Jun. 1995, pp. 754-760.
Shi Y., "Serine/Threonine Phosphatases: Mechanism Through Structure," Cell, Oct. 2009, vol. 139, pp. 468-484.
Shimi et al., "A new antitumour substance, 7-oxabicyclo (2.2.1)-5-heptene-2,3-dicarboxylic anhydride," European Journal of Cancer, vol. 18, No. 8, Aug. 1982 (pp. 785-793).
Short et al., "DNA repair after irradiation in glioma cells and normal human astrocytes," Neuro-Oncology, vol. 9, No. 4, Oct. 2007 (pp. 404-411).
Shukron, O. et al., Analyzing transformation of myelodysplastic syndrome to secondary acute myeloid leukemia using a large patient database. Am. J. Hematol. 87:853-860 (2012).
Silver, D. P. et al., "Efficacy of neoadjuvant Cisplatin in triple-negative breast cancer," Journal of Clinical Oncology, vol. 28, No. 7, Mar. 2010, pp. 1145-1153.
Simboeck, E. et al., A phosphorylation switch regulates the transcriptional activation of cell cycle regulator p21 by histone deacetylase inhibitors. J Biol Chem 285(52):41062-41073 (2010).
Simizu, S. et al., Dephosphorylation of Bcl-2 by protein phosphatase 2A results in apoptosis resistance. Cancer Sci 95:266-270 (2004).
Singh, et al., "Identification of a cancer stem cell in human brain tumors." Cancer Res. (2003); 63 (18): 5821-5828.
Singh, et al., "Identification of human brain tumour initiating cells." Nature (2004); 432 (7015): 396-401.
Smith et al., "Histone deacetylase inhibitors enhance Candida albicans sensitivity to azoles and related antifungals: correlation with reduction in CDR and ERG upregulation," Antimicrobial Agents and Chemotherapy, vol. 46, No. 11, Nov. 2002 (pp. 3532-3539).
Smith-Cohn, M. A. et al., "Molecularly Targeted Clinical Trials," Feb. 2021, Neurosurgery Clinics, vol. 32, Issue 2, pp. 191-210.
Snyder A., et al., "Genetic Basis for Clinical Response to CTLA-4 Blockade in Melanoma," The New England Journal of Medicine, Dec. 4, 2014, vol. 371 (23), pp. 2189-2199.
Song et al., Synthesis and Biological Properties of Amino Acid Amide Ligand-Based Pyridinioalkanoyl Thioesters as Anti-HIV Agents, Bioorganic and Medicinal Chemistry, vol. 10, No. 5, May 2002 (pp. 1263-1273).
Sontag, E. et al., "Regulation of the Phosphorylation State and Microtubule-Binding Activity of Tau by Protein Phosphatase 2A," Neuron, vol. 17, Issue 6, Dec. 1996, pp. 1201-1207.
Sorrentino, A. et al., Role of microRNAs in drug-resistant ovarian cancer cells. Gynecol. Oncol., 111:478-486 (2008).
Sotillo, R. et al., "Mad2 overexpression promotes aneuploidy and tumorigenesis in mice," Cancer Cell, vol. 11, No. 1, Jan. 2007, pp. 9-23.
Sotillo, R. et al., "Mad2-induced chromosome instability leads to lung tumour relapse after oncogene withdrawal," Nature, vol. 464, No. 7287, Mar. 2010, pp. 436-440; doi:10.1038/nature08803.
Sridharan et al., "Illuminating the black box of reprogramming," Cell Stem Cell, vol. 2, No. 4, Apr. 2008 (pp. 295-297).
Srivastava, R. K. et al., MS-275 sensitizes TRAIL-resistant breast cancer cells, inhibits angiogenesis and metastasis, and reverses epithelial-mesenchymal transition in vivo. Mol. Cancer Ther. 9(12):3254-3266 (2010).
Stanford, S. M. et al., "Targeting protein phosphatases in cancer immunotherapy and autoimmune disorders," Nature Reviews Drug Discovery, (Jan. 2023), https://doi.org/10.1038/s41573-022-00618-w, 22 pages.
Stewart et al., "Synthesis and biological evaluation of norcantharidin analogues: towards PP1 selectivity," Bioorganic and Medicinal Chemistry, vol. 15, No. 23, Dec. 2007 (pp. 7301-7310).
Stoll, V. S. et al., Chapter 6: "Buffers: Principles and Practice," In Methods in Enzymology, Academic Press, 1990, vol. 463, ISSN 0076-6879, pp. 43-56.
Strebhardt et al., "Targeting polo-like kinase 1 for cancer therapy," Nature Reviews: Cancer, vol. 6, Apr. 2006 (11 pages).
Stuart, T. et al. (Jun. 2019), "Comprehensive Integration of Single-Cell Data," Cell, vol. 177, pp. 1888-1902. https://doi.org/10.1016/j.cell.2019.05.031.
Stupp R., et al., "Effects of Radiotherapy With Concomitant and Adjuvant Temozolomide Versus Radiotherapy Alone on Survival in Glioblastoma in a Randomised Phase III study: 5-year Analysis of The EORTC-NCIC Trial," Lancet, Oncology, May 2009, vol. 10 (5), pp. 459-466.
Stupp, R. et al., "Radiotherapy plus Concomitant and Adjuvant Temozolomide for Glioblastoma," N Engl J Med, 352(10):987-996 (2005).
Subbiah, S., et al., "Small Cell Lung Cancer from Traditional to Innovative Therapeutics: Building a Comprehensive Network to Optimize Clinical and Translational Research," Journal of Clinical Medicine, Jul. 30, 2020, vol. 9(8), 19 pages. [Retrieved on Nov. 9, 2021]. Retrieved from the Internet: URL: https://www.mdpi.com/2077-0383/9/8/2433.
Subramanian, A. et al. (Oct. 2005), "Gene set enrichment analysis: A knowledge-based approach for interpreting genome-wide expression profiles, " Proc Natl Acad Sci USA, vol. 102, No. 43, pp. 15545-15550. www.pnas.orgcgidoi10.1073pnas.0506580102.
Suganuma, M. et al., "Okadaic acid: an additional non-phorbol-12-tetradecanoate-13-acetate-type tumor promoter," Proceedings of the National Academy of Sciences, USA, vol. 85, No. 6, Mar. 1988, pp. 1768-1771.
Sukari A., et al., "Cancer Immunology and Immunotherapy," Anticancer Research, 2016, vol. 36, pp. 5593-5606.
Sundstrom, S. et al., "Cisplatin and etoposide regimen is superior to cyclophosphamide, epirubicin, and vincristine regimen in small-cell lung cancer: results from a randomized phase III trial with 5 years' follow-up," Journal of Clinical Oncology, Dec. 2002, vol. 20, No. 24, pp. 4665-4672.
Sunny-Roberts, E. O. et al., "The protective effect of monosodium glutamate on survival of lactobacillus rhamnosus GG and lactobacillus rhamnosus E-97800 (E800) strains during spray-drying and storage in trehalose-containing powders," International Dairy Journal, 2009, vol. 19, pp. 209-214.
Susini, L. et al., "TCTP protects from apoptotic cell death by antagonizing bax function," Cell Death and Differentiation, vol. 15, No. 8, Feb. 2008, pp. 1211-1220.
Suzuki, T., et al., "Synthesis and histone deacetylase inhibitory activity of new benzamide derivatives," Journal of Medicinal Chemistry, vol. 42, No. 15, Jul. 1999 (pp. 3001-3003).
Swart M., et al., "Combination Approaches with Immune-Checkpoint Blockade in Cancer Therapy," Frontiers in Oncology, Nov. 1, 2016, vol. 6, Article 233, pp. 1-16.
Sweatt, "Behavioural Neuroscience: Down Memory Lane," Nature, vol. 447, May 2007 (pp. 151-152).

(56) References Cited

OTHER PUBLICATIONS

Szklarczyk, D. et al. (2015). STRING v10: Protein-protein interaction networks, integrated over the tree of life. Nucleic Acids Research, 43(D1):D447-D452. https://doi.org/10.1093/nar/gku1003.
Taffs, R. E. et al., "Modulation of Cytolytic T Lymphocyte Functions by an Inhibitor of Serine/Threonine Phosphatase, Okadaic Acid. Enhancement of Cytolytic T Lymphocyte-Mediated Cytotoxicity," The Journal of Immunology, Jul. 1991, vol. 147, No. 2, pp. 722-728.
Tanaka, H. et al., "Studies on sulfur-containing chelating agents. X. Mercapto-acid amides and their metal chelates," Chemical and Pharmaceutical Bulletin (Tokyo), vol. 10, Jul. 1962, pp. 556-562.
Tanaka, K. et al., "Mitotic checkpoint protein hsMAD2 as a marker predicting liver metastasis of human gastric cancers," Japanese Journal of Cancer Research, vol. 92, No. 9, pp. 952-958 (Sep. 2001).
Tecentriq Prescribing Information, Genentech Inc., FDA Approved Labeling, Reference ID:4000525, 2016, p. 23, Retrieved from the Internet: URL: www.accessdata.fda.gov/drugsatfda docs/label/2016/761041lbl.pdf.
Tefferi and Vardiman, "Myelodysplastic syndromes". N Engl J Med. (Nov. 5, 2009); 361(19): 1872-1885.
Teft, W. A. et al., "A Molecular Perspective of CTLA-4 Function," Annu. Rev. Immunol. (2006) 24:65-97.
Teft, W. A. et al., "Structure-Function Analysis of The CTLA-4 Interaction with PP2A," BioMed Central (BMC) Immunology, Apr. 2009, vol. 10, No. 23, pp. 1-10.
Testa, B. et al., "The Hydrolysis of Carboxylic Acid Ester Prodrugs," Chapter 8 In: Hydrolysis in Drug and Prodrug Metabolism: Chemistry, Biochemistry, and Enzymology, Helvetica Chimica Acta, Jan. 2003, pp. 419-534.
Thi, T. et al., "Metabolic Reprogramming by c-MET Inhibition as a Targetable Vulnerability in Glioblastoma," Oncoscience, vol. 7(1-2), (Jan. 2020), pp. 14-16.
Thiel, K.A. (May 2004) "Structure-aided drug design's next generation" Nat Biotechnol, 22(5):513-519.
Thiery, J. P. et al., "Hepatocellular Carcinoma Cell Lines From Diethylnitrosamine Phenobarbital-Treated Rats. Characterization and Sensitivity to Endothall, a Protein Serine/Threonine Phosphatase-2A Inhibitor," Hepatology, May 1999, vol. 29, No. 5, pp. 1406-1417.
Thompson, J. J. et al. (2018). Protein phosphatase 2A in the regulation of wnt signaling, stem cells, and cancer. Genes, vol. 9, Issue 121, 11 pages. https://doi.org/10.3390/genes9030121.
Tian, Q. et al., "Role of Serine/Threonine Protein Phosphatase in Alzheimer's Disease," Neurosignals, vol. 11, No. 5, (2002), pp. 262-269.
Tocris Biosciences, "Retinoic Acid Receptors," Product Data Sheet (2010), 1 page.
Toma et al., "Retinoids and human breast cancer: in vivo effects of an antagonist for RAR-alpha," Cancer Letters, vol. 219, No. 1, Feb. 2005 (pp. 27-31).
Tong, H. et al., P-285, "LB1, Targeting Inhibiting Protein Phosphatase 2A (PP2A), Enhances Daunorubicin Suppression of MDS Cell Line (SKM-1) in Vitro and in Vivo," Leukemia Research, 2013, vol. 37(S1), pp. S150-S151.
Topalian et al., "Immune Checkpoint Blockade: A Common Denominator Approach to Cancer Therapy," Cancer Cell, 2015, vol. 27, pp. 450-461.
Topalian, S. L. et al., "Immunotherapy: The Path to Win the War on Cancer?," Cell, Apr. 2015, vol. 161, No. 2, pp. 185-186.
Touma et al., "Retinoic acid and the histone deacetylase inhibitor trichostatin a inhibit the proliferation of human renal cell carcinoma in a xenograft tumor model," Clinical Cancer Research, vol. 11, No. 9, May 2005 (pp. 3558-3566).
Traag, V. A. et al. (Mar. 2019), "From Louvain to Leiden: guaranteeing well-connected communities," Scientific Reports, vol. 9:5233, 12 pages. https://doi.org/10.1038/s41598-019-41695-z.
Trost et al., "New synthetic reagents, Methylthiomaleic anhydride: a synthon for protected carbomethoxyketene," Journal of the American Chemical Society, vol. 99, No. 21, Oct. 1977 (pp. 7079-7082).
Tsang, A. et al., "Myocardial postconditioning: reperfusion injury revisited," American Journal of Physiology-Heart Circulation Physiology, vol. 289, No. 1, Jul. 2005, pp. H2-H7.
Tsauer W., et al., "The Effects of Cantharidin Analogues on Xanthine Oxidase," Anticancer Research, May-Jun. 1997, vol. 17 (3C), pp. 2095-2098.
Tsiatas, M. et al., "Future Perspective in Cancer Immunotherapy," Annals of Translational Medicine, Jul. 2016, 4(14):273, 7 pages.
Tuynder et al., "Biological models and genes of tumor reversion: cellular reprogramming through tpt1/TCTP and SIAH-1," Proceedings of the National Academy of Sciences U.S.A., vol. 99, No. 23, Nov. 2002 (pp. 14976-14981).
Tuynder et al., "Translationally controlled tumor protein is a target of tumor reversion," Proceedings of the National Academy of Sciences U.S.A., vol. 101, No. 43, Oct. 2004 (pp. 15364-154369).
Uchida, et al., "Direct isolation of human central nervous system stem cells." Proc Natl Acad Sci U S A. (2000); 97 (26): 14720-14725.
Uemura, K. et al., "GSK3B Activity Modifies the Localization and Function of Presenilin 1," The Journal of Biological Chemistry, vol. 282, No. 21, May 2007, pp. 15823-15832.
Ugi, S. et al., Protein phosphatase 2A forms a molecular complex with Shc and regulates Shc tyrosine phosphorylation and downstream mitogenic signaling. Mol Cell Biol 22(7):2375-2387 (Apr. 2002).
Unni, A. M. et al. (2018). Hyperactivation of ERK by multiple mechanisms is toxic to RTK-RAS mutation-driven lung adenocarcinoma cells. ELife, 7, pp. 1-24. https://doi.org/10.7554/eLife.33718.
Unni, A. M. et al. (Jun. 2015). Evidence that synthetic lethality underlies the mutual exclusivity of oncogenic KRAS and EGFR mutations in lung adenocarcinoma. ELife, e06907. http://dx.doi.org/10.7554/eLife.06907, 23 pages.
U.S. Department of Health and Human Services, et al., "Guidance for Industry: Estimating the Maximum Safe Starting Dose in Initial Clinical Trials for Therapeutics in Adult Healthy Volunteers", Pharmacology and Toxicology (Jul. 2005) [online] https://www.fda.gov/media/72309/download"https://www.fda.gov/media/72309/download (Access Date: Jun. 9, 2020); 30 pages.
Vainonen, J. P. et al. (Apr. 2021). Druggable cancer phosphatases. Sci. Transl. Med. vol. 13, eabe2967, 13 pages.
Valdiglesias, V. et al., Okadaic acid: more than a diarrheic toxin. Mar. Drugs 11:4328-4349 (2013).
Valeriote et al., "Synergistic interaction of anticancer agents: a cellular perspective," Cancer Chemotherapy Reports, vol. 59, No. 5, Sep.-Oct. 1975 (pp. 895-900).
Van Deursen, J. M., "Rb loss causes cancer by driving mitosis mad," Cancer Cell, vol. 11, No. 1, Jan. 2007, pp. 1-3.
Van Hoof, C. et al., "PP2A fulfills its promises as tumor suppressor: which subunits are important?" Cancer Cell, vol. 5, No. 5, Feb. 2004, pp. 105-106.
Vardiman, J., "The Classification of MDS: from FAB to WHO and Beyond," Leukemia Research, Dec. 2012, vol. 36, No. 12, pp. 1453-1458.
Vardiman, J. W. et al., "The 2008 revision of the World Health Organization (WHO) classification of myeloid neoplasms and acute leukemia: rationale and important changes," Blood, vol. 114, No. 5, pp. 937-951 (Jul. 2009).
Vardiman, J. W., The World Health Organization (WHO) classification of tumors of the hematopoietic and lymphoid tissues: an overview with emphasis on the myeloid neoplasms. Chem Biol Interact 184:16-20 (2010).
Vazquez A., et al., "The Genetics of the p53 Pathway, Apoptosis and Cancer Therapy," Nature Reviews Drug Discovery, Dec. 2008, vol. 7, pp. 979-987.
Vigneron, S. et al., Greatwall maintains mitosis through regulation of PP2A. The EMBO Journal, 28:2786-2793 (2009).
Virzi, A. R. et al., "Reviving oncogenic addiction to MET bypassed by BRAF (G469A) mutation," Proc Natl Acad Sci USA, vol. 115, No. 40, pp. 10058-10063 (Oct. 2018).

(56) References Cited

OTHER PUBLICATIONS

Vitale, I. et al. (2011). Mitotic catastrophe: a mechanism for avoiding genomic instability. Nature Reviews. Molecular Cell Biology, 12(6):385-392. https://doi.org/10.1038/nrm3115.
Walter, M. J. et al., Clonal architecture of secondary acute myeloid leukemia. N Engl J Med 366:1090-1098 (2012).
Wang, C., et al., "In Vitro Characterization of the Anti-PD-1 Antibody Nivolumab, BMS-936558, and In Vivo Toxicology in Non-Human Primates Characterization of the Anti-PD-1 Antibody Nivolumab", Cancer Immunology Research (2014); 2(9): 846-856.
Wang, C-C et al., Cytotoxic effects of cantharidin on the growth of normal and carcinoma cells. Toxicology 147:77-87 (2000).
Wang, G. S. (1983), "Hydrolysis and demethylation of cantharidin on the relief of its urinary irritation," Chin. Pharmac. Bull., vol. 18, No. 7, pp. 18-19.
Wang, G. S. et al. (1986), "Results of clinical trials in 244 cases of primary hepatoma and with norcantharidin," Chinese Pharm. Bull., vol. 21, No. 2. pp. 90-93.
Wang, G. S. et al. (1987), "Effect of norcantharidin on the number of white blood cells," Chinese Pharm. Bull., vol. 22, pp. 517-519.
Wang, G. S., "Medical Uses of Mylabris in Ancient China and Recent Studies," Journal of Ethnopharmacology, Sep. 1989, vol. 26, Issue 2, pp. 147-162.
Wang, J. et al., Inhibiting crosstalk between MET signaling and mitochondrial dynamics and morphology: a novel therapeutic approach for lung cancer and mesothelioma. Cancer Biol Ther 19, 1023-1032 (2018).
Wang, L. et al. (2022). Exploiting senescence for the treatment of cancer. In Nature Reviews Cancer, Nature Research, vol. 22, Issue 6, pp. 340-355. https://doi.org/10.1038/s41568-022-00450-9.
Wang, L. et al., An Acquired Vulnerability of Drug-Resistant Melanoma with Therapeutic Potential. Cell. May 2018, 173(6):1413-1425.
Wang, L. et al., High-Throughput Functional Genetic and Compound Screens Identify Targets for Senescence Induction in Cancer. Cell Rep. Oct. 2017, 21(3):773-783.
Wang, L. et al., "MAD2 as a key component of mitotic checkpoint: A probable prognostic factor for gastric cancer," American Journal of Clinical Pathology, vol. 131, No. 6, Jun. 2009, pp. 793-801.
Wang, R. et al., Okadaic acid inhibits cell multiplication and induces apoptosis in a549 cells, a human lung adenocarcinoma cell line. Int J Clin Exp Med 7(8):2025-2030 (2014).
Wang, X., The expanding role of mitochondria in apoptosis. Genes & Development, 15:2922-2933 (2001).
Wang, Y. et al., "Cross talk between PI3K-AKT-GSK-3beta and PP2A pathways determines tau hyperphosphorylation," Neurobiol Aging. 2015;36(1):188-200.
Warr, M. R. et al. (2008), "Unique Biology of Mcl-1: Therapeutic opportunities in cancer," Current Molecular Medicine, vol. 8, No. 2, pp. 139-147.
Warrell et al., "Therapeutic Targeting of Transcription in Acute Promyelocytic Leukemia by Use of an Inhibitor of Histone Deacetylase," Journal of the National Cancer Institute, vol. 90, No. 21, Nov. 1998 (pp. 1621-1625).
Warren K., et al., "A phase 2 Study of Pegylated Interferon α-2b (PEG-Intron®) in Children with Diffuse Intrinsic Pontine Glioma," Cancer, Jul. 15, 2012, vol. 118 (14), pp. 3607-3613.
Wassmann, K. et al., "Mad2 phosphorylation regulates its association with Mad1 and the APC/C," The EMBO Journal, vol. 22, No. 4, Feb. 2003, pp. 797-806.
Waters, C. E. et al., "Analysis of Co-Factor Function in a Glucocorticoid-Resistant Small Cell Carcinoma Cell Line," Journal of Endocrinology, 2004, vol. 183, pp. 375-383.
Waters, J. S. et al., Phase I clinical and pharmacokinetic study of bcl-2 antisense oligonucleotide therapy in patients with non-Hodgkin's lymphoma. J Clin Oncol 18:1812-1823 (2000).
Wei, D. et al., "Inhibition of protein phosphatase 2A radiosensitizes pancreatic cancers by modulating CDC25C/CDKI and homologous recombination repair," Clin Cancer Res. 2013; 19(16):4422-4432.
Wei, K-C. et al., "Focused Ultrasound-Induced Blood-Brain Barrier Opening to Enhance Temozolomide Delivery for Glioblastoma Treatment: A Preclinical Study," PLoS One, 2013, vol. 8(3), e58995, 10 pages.
Wei, M. C. et al., Proapoptotic BAX and BAK: a requisite gateway to mitochondrial dysfunction and death. Science 292:727-730 (Apr. 2001).
Wei, S. et al., "A critical role for phosphatase haplodeficiency in the selective suppression of deletion 5q MDS by lenalidomide," PNAS, vol. 106, No. 31, pp. 12974-12979 (Aug. 2009); with Correction, PNAS, vol. 110, No. 35 (Aug. 2013), p. 14504.
Wei, S. et al., "Lenalidomide promotes p53 degradation by inhibiting MDM2 auto-ubiquitination in myelodysplastic syndrome with chromosome 5q deletion," Oncogene, 32(9):1110-1120 (Feb. 2013).
Wei, W. et al., "Hypoxia induces a phase transition within a kinase signaling network in cancer cells," Proceedings of the National Academy of Sciences, U.S.A., vol. 110, No. 15, Apr. 2013, pp. E1352-E1360.
Weinmann et al., "Histone deacetylase inhibitors: a survey of recent patents," Expert Opinion on Therapeutic Patents, vol. 15, No. 12, Nov. 2005 (pp. 1677-1690).
Westermarck J., et al., "Multiple Pathways Regulated by the Tumor Suppressor PP2A in Transformation," Trends in Molecular Medicine, 2008, vol. 14 (4), pp. 152-160.
Wikipedia, "Platinum-based Antineoplastic," [Online], https://en.wikipedia.org/wiki/platinum-based_antineoplastic, Visited Jan. 2018, 4 pages.
Williams, Lad et al., In vitro anti-proliferation/cytotoxic activity of cantharidin (Spanish Fly) and related derivatives. West Indian Med J., 52(1):10-13 (2003).
Winstanley, K. J. et al., "Ortho-substituted catechol derivatives: The effect of intramolecular hydrogen-bonding pathways on chloride anion recognition," J. Org. Chem., vol. 72, No. 8, 2007, pp. 2803-2815.
Wolchok, J. D. et al., "Nivolumab Plus Ipilimumab in Advanced Melanoma," The New England Journal of Medicine, Jul. 2013, vol. 369, No. 2, pp. 122-133.
Xia, L et al., miR-15b and miR-16 modulate multidrug resistance by targeting BCL2 in human gastric cancer cells. Int. J. Cancer, 123:372-379 (2008).
Xiao, C. et al., MicroRNA control in the immune system: basic principles. Cell, 136:26-36 (Jan. 2009).
Xiao, G. et al., "B-Cell-Specific Diversion of Glucose Carbon Utilization Reveals a Unique Vulnerability in B Cell Malignancies," Cell, Apr. 2018; 173(2):470-484.
Xie, Z. et al. (2021), "Gene Set Knowledge Discovery with Enrichr.," Current Protocols, vol. 1, e90, 52 pages. doi: 10.1002/cpz1.90.
Xu, Y. et al., "Structure of the Protein Phosphatase 2A Holoenzyme," Cell, 2006, vol. 127, No. 6, pp. 1239-1251.
Yadav, B. et al. (2015). Searching for Drug Synergy in Complex Dose-Response Landscapes Using an Interaction Potency Model. Computational and Structural Biotechnology Journal, vol. 13, pp. 504-513. https://doi.org/10.1016/j.csbj.2015.09.001.
Yan et al., "Inhibition of protein phosphatase activity induces p53-dependent apoptosis in the absence of p53 transactivation," Journal of Biological Chemistry, vol. 272, No. 24, Jun. 1997 (pp. 15220-15226).
Yanez, A. G., Regulation of microRNA activity by translation initiation factors in melanoma. Doctoral Dissertation, Harvard University (May 2014), 162 pages.
Yang et al., "An N-terminal region of translationally controlled tumor protein is required for its antiapoptotic activity," Oncogene, vol. 24, No. 30, Jul. 2005 (pp. 4778-4788).
Yang, S-H. et al., "Perspectives on the combination of radiotherapy and targeted therapy with DNA repair inhibitors in the treatment of pancreatic cancer," Aug. 2016, World Journal of Gastroenterology, vol. 22, Issue 32, pp. 7275-7288.
Yang, Y. et al., Reactivating PP2A by FTY720 as a novel therapy for AML with C-KIT tyrosine kinase domain mutation. J. Cell. Biochem., 113:1314-1322 (2012).
Yang Y-H., et al., "Enzyme-mediated Hydrolytic Activation of Prodrugs," Acta Pharmaceutica Sinica B, Oct. 2011, vol. 1 (3), pp. 143-159.

(56) References Cited

OTHER PUBLICATIONS

Yao, D. et al. (2014). A review of the clinical diagnosis and therapy of cholangiocarcinoma. Journal of International Medical Research, vol. 42, Issue 1, pp. 3-16. https://doi.org/10.1177/0300060513505488.

Yarm, "Plk phosphorylation regulates the microtubule-stabilizing protein TCTP," Molecular and Cellular Biology, vol. 22, No. 17, Sep. 2002 (pp. 6209-6221).

Yatsunami, J. et al., "Hyperphosphorylation of Cytokeratins by Okadaic Acid Class Tumor Promoters in Primary Human Keratinocytes," Cancer Research, Mar. 1993, vol. 53, pp. 992-996.

Yellon, D. M. et al., "Realizing the clinical potential of ischemic preconditioning and postconditioning," Nature Clinical Practice Cardiovascular Medicine, vol. 2, No. 11, Nov. 2005, pp. 568-575.

Yen Y-T., et al., "Protein Phosphatase 2A Inactivation Induces Microsatellite Instability, Neoantigen Production and Immune Response," Nature Communications, 2021, vol. 12, Article No. 7297, pp. 1-14.

YERVOY® (Ipilimumab), Label; Highlights of Prescribing Information, approved by the U.S. Food and Drug Administration; Revised: Oct. 2015(Oct. 2015), Initial U.S. Approval: 2011, Reference ID: 3839653, Manufactured by: Bristol-Myers Squibb Company, Princeton, NJ 08543 USA, 32 pages.

Yi, C. et al., "Determination of malignant disease-associated DNA-binding protein 2 in patients with liver cancer," Hua Xi Yi Ke Da Xue Xue Bao, vol. 31, No. 3, Sep. 2000, pp. 310-311, English Abstract, 1 page.

Yin, X. et al., "Regulation of LC3-dependent protective autophagy in ovarian cancer cells by protein phosphatase 2A," Int J Gynecol Cancer, May 2013; 23(4):630-641. doi: 10.1097/IGC.0b013e3182892cee.

Yoshida et al., "Potent and specific inhibition of mammalian histone deacetylase both in vivo and in vitro by trichostatin A," Journal of Biological Chemistry, vol. 265, No. 28, Oct. 1990 (pp. 17174-17179).

Yoshida, M. et al. (1999), "Trichostatin and leptomycin. Inhibition of histone deacetylation and signal-dependent nuclear export," Annals of the New York Academy of Sciences, vol. 886, pp. 23-26.

Yu, L. et al., "Mitotic arrest defective protein 2 expression abnormality and its clinicopathologic significance in human osteosarcoma," APMIS, vol. 118, No. 3, Mar. 2010, pp. 222-229.

Yu, L. et al., Modeling the Genetic Regulation of Cancer Metabolism: Interplay between Glycolysis and Oxidative Phosphorylation. Cancer Res 77, 1564-1574 (2017).

Yung, W. K. A. et al., "Treatment of Recurrent Malignant Gliomas With High-Dose 13-cis-Retinoic Acid," Clinical Cancer Research, Dec. 1996, vol. 2, No. 12, pp. 1931-1935.

Zeman, M. K. et al. (Jan. 2014), "Causes and consequences of replication stress," Nat. Cell. Biol., vol. 16, No. 1, 8 pages.

Zhang, C. et al., "A synthetic cantharidin analog for the enhancement of doxorubicin suppression of stem cell-derived aggressive sarcoma," Biomaterials, 31(36):9535-9543 (Dec. 2010).

Zhang C., et al., "Inhibition of Protein Phosphatase 2A with the Small Molecule LB100 Overcomes Cell Cycle Arrest in Osteosarcoma After Cisplatin Treatment," Cell Cycle, Jul. 1, 2015, vol. 14 (13), pp. 2100-2108.

Zhang, L. et al., Role of BAX in the apoptotic response to anticancer agents. Science 290:989-992 (Nov. 2000).

Zhang, M. et al., "Viewing Serine/Threonine Protein Phosphatases through the Eyes of Drug Designers," FEBS J., Oct. 2013, vol. 280, No. 19, pp. 4739-4760.

Zhang, S-H et al., "Clinicopathologic significance of mitotic arrest defective protein 2 overexpression in hepatocellular carcinoma," Human Pathology, vol. 39, No. 12, Dec. 2008, pp. 1827-1834.

Zhao, X. Z. et al., "2,3-dihydro-6,7-dihydroxy-1 H-isoindol-1- one based HIV-1 integrase inhibitors," J Med Chem, vol. 51, No. 2, (2008) pp. 251-259.

Zhao, Y. et al., Roles of Greatwall kinase in the regulation of cdc25 phosphatase. Mol. Biol. Cell, 19:1317-1327 (Apr. 2008).

Zheng, T. et al., Role of microRNA in anticancer drug resistance. Int. J. Cancer, 126:2-10 (2010).

Zhou, B. et al., The specificity of extracellular signal-regulated kinase 2 dephosphorylation by protein phosphatases. J Biol Chem 277(35):31818-31825 (Aug. 2002).

Zhou, P. et al., "In Vivo Discovery of Immunotherapy Targets in The Tumour Microenvironment," Nature, Feb. 2014, vol. 506, No. 7486, pp. 52-57.

Zhu, J. et al. (May 2008), "Activation of PI3K/Akt and MAPK pathways regulates Myc-mediated transcription by phosphorylating and promoting the degradation of Mad1," Proc Natl Acad Sci USA, vol. 105, No. 18, pp. 6584-6589.

Zhu W., et al., "miR-181b Modulates Multidrug Resistance by Targeting BCL2 in Human Cancer Cell Lines," International Journal of Cancer, 2010, vol. 127 (11), pp. 2520-2529.

Zhu, X. N. et al., PP2A-AMPKalpha-HSF1 axis regulates the metal-inducible expression of HSPs and ROS clearance. Cell Signal. 2014;26(4):825-832.

Zhuang, Z. et al., "Enhancement of cancer chemotherapy by simultaneously altering cell cycle progression and DNA-damage defenses through global modification of the serine/threonine phosphoproteome," Cell Cycle, 8(20):3303-3306 (Oct. 2009).

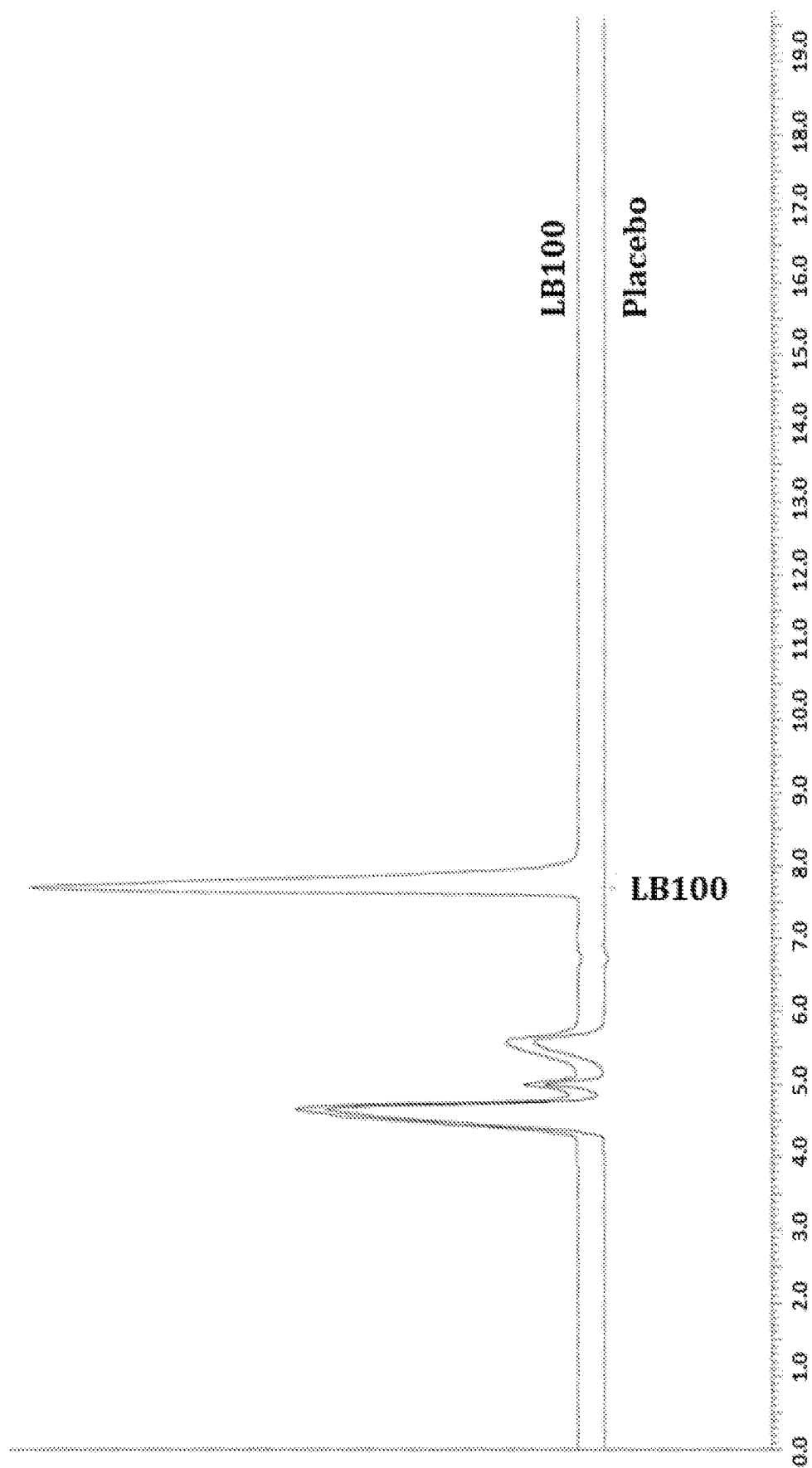

METHODS FOR TREATING SOFT TISSUE SARCOMA

CROSS-REFERENCE TO RELATED APPLICATIONS

This application is a continuation of U.S. application Ser. No. 16/705,699, filed Dec. 6, 2019, which is a division of U.S. application Ser. No. 14/783,360, filed Oct. 8, 2015, now U.S. Pat. No. 10,532,050, which is the U.S. national stage of International Patent Application No. PCT/US2014/033317, filed Apr. 8, 2014, which claims the benefit of U.S. Provisional Application No. 61/810,053, filed Apr. 9, 2013, each of which is incorporated by reference herein in its entirety.

Throughout this application various publications are referenced. The disclosures of these documents in their entireties are hereby incorporated by reference into this application in order to more fully describe the state of the art to which this invention pertains.

BACKGROUND OF THE INVENTION

PCT International Application Publication Nos. WO 2008/097561, WO 2009/020565, WO 2010/014141, WO 2010/014220, WO 2010/014254, WO 2010/147612, and WO 2012/162535 describe small molecule protein phosphatase 2A (PP2A) inhibitors and their use for treating a variety of conditions including cancers, neurodegenerative diseases, and diseases characterized by loss of protein function.

One of the PP2A inhibitors described in PCT International Application Publication No. WO 2008/097561, LB-100, has shown antiproliferative activity as a single agent and in combination with other cytotoxic agents against cancer cells in vitro and against tumor xenografts in in vivo animal models. For example, LB-100 was shown to inhibit the growth of glioblastoma multiforme (GBM) xenograft cells (Lu et al., J. Neurosurg. 113:225-233 (2010)), increase the effectiveness of the standard anti-sarcoma chemotherapeutic agent doxorubicin in a rat fibrosarcoma model (Zhang et al., Biomaterials vol. 31(36):9535-43 (2010)), and delay tumor growth when administered with temozolomide (TMZ) in a mouse model of metastatic pheochromocytoma (PHEO) (Martiniova et al., Plos One, vol. 6(2):e14678 (2011)).

To date, the PP2A inhibitors described in PCT International Application Publication Nos. WO 2008/097561, WO 2009/020565, WO 2010/014141, WO 2010/014220, WO 2010/014254, WO 2010/147612, and WO 2012/162535 have not been explored in human clinical trials. However, LB-100 has been approved by the Food and Drug Administration for Phase I study in patients with advanced cancers given alone and then in combination with the widely used anticancer drug docetaxel.

Accordingly, there is a need for pharmaceutical compositions comprising PP2A inhibitors, and LB-100 in particular, which are suitable for administration to human subjects in, for example, clinical trials. Such pharmaceutical compositions should be stable under long term storage conditions and under the conditions of clinical use.

SUMMARY OF THE INVENTION

The subject invention provides a pharmaceutical composition comprising a protein phosphatase 2A inhibitor and monosodium glutamate.

In an embodiment of the pharmaceutical composition, the protein phosphatase 2A inhibitor has the structure

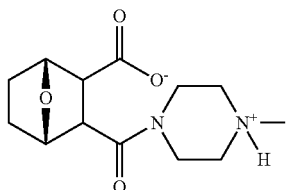

or a salt or enantiomer thereof.

The invention also provides a sealed package comprising the pharmaceutical composition of the invention.

The invention also provides a method of preparing a pharmaceutical composition for administration to a subject, comprising mixing an amount of the pharmaceutical composition of the invention with a saline solution.

The invention also provides a method of preparing a pharmaceutical composition for administration to a subject, comprising removing an amount of pharmaceutical composition from the sealed package of the invention and mixing the amount of the pharmaceutical composition with a saline solution.

The invention also provides a pharmaceutical composition produced by the above methods.

The invention also provides a method of making the pharmaceutical composition of the invention, comprising
  a) adding an amount of monosodium glutamate to an amount of water to form a mixture of monosodium glutamate and water; and
  b) adding an amount of a protein phosphatase 2 inhibitor to the mixture.

The invention also provides a pharmaceutical composition produced by the above method.

The invention also provides a method of treating a subject afflicted with a condition or disease amenable to treatment with a PP2A inhibitor comprising administering to the subject a pharmaceutical composition of the invention in an amount effective to treat the subject.

The invention also provides a method of treating a subject afflicted with cancer comprising administering to the subject a pharmaceutical composition of the invention in an amount effective to treat the subject.

The invention also provides a method of treating a subject afflicted with a neurodegenerative disease comprising administering to the subject a pharmaceutical composition of the invention in an amount effective to treat the subject.

The invention also provides a method of treating a subject afflicted with a disease characterized by a loss of protein function caused by a genetic abnormality associated with the disease comprising administering to the subject a therapeutically effective amount of a pharmaceutical composition of the invention.

The invention also provides methods of reducing reperfusion injury, tissue damage associated with reperfusion injury, vascular leakage associated with reperfusion injury, tissue damage due to an acute trauma, and vascular leakage due to an acute trauma, comprising administering a therapeutically effective amount of a pharmaceutical composition of the invention to a subject in need thereof.

BRIEF DESCRIPTION OF THE DRAWINGS

FIG. 1: Representative HPLC chromatogram for the formulation of 1 mg/ml LB-100 in 0.1 M monosodium glutamate, pH 10.5, after 9 months of storage at −20° C.±10° C.

DETAILED DESCRIPTION OF THE INVENTION

The subject invention provides a pharmaceutical composition comprising a protein phosphatase 2A inhibitor and monosodium glutamate.

In an embodiment of the pharmaceutical composition, the protein phosphatase 2A inhibitor has the structure

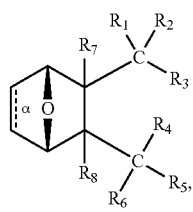

wherein
bond α is present or absent;
$R_1$ and $R_2$ is each independently H, O⁻ or $OR_9$,
    where $R_9$ is H, alkyl, alkenyl, alkynyl or aryl,
or $R_1$ and $R_2$ together are =O;
$R_3$ and $R_4$ are each different, and each is OH, O⁻, $OR_9$, SH, S⁻, $SR_9$,

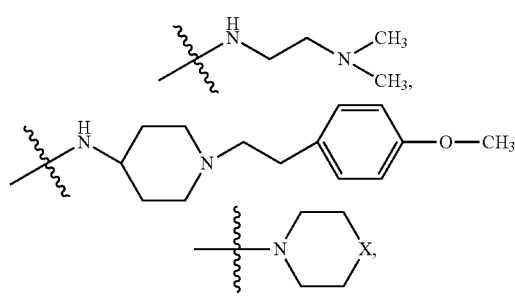

where X is O, S, $NR_{10}$, or $N^+R_{10}R_{10}$,
    where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

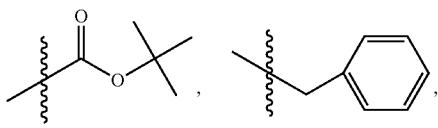

—$CH_2CN$, —$CH_2CO_2R_{11}$, —$CH_2COR_{11}$, —$NHR_{11}$ or —$NH^+(R_{11})_2$,
    where each $R_{11}$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
    where $R_{12}$ is H, aryl or a substituted or unsubstituted alkyl, alkenyl or alkynyl;
or a salt, enantiomer or zwitterion of the compound.

In an embodiment of the pharmaceutical composition, the protein phosphatase 2A inhibitor has the structure

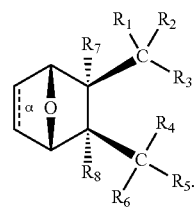

In an embodiment of the pharmaceutical composition, the protein phosphatase 2A inhibitor has the structure

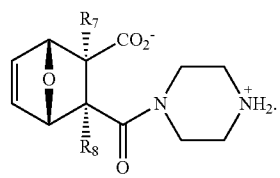

In an embodiment of the pharmaceutical composition, the protein phosphatase 2A inhibitor has the structure

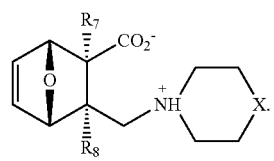

In an embodiment of the pharmaceutical composition, bond α is present.

In an embodiment of the pharmaceutical composition, bond α is absent.

In an embodiment of the pharmaceutical composition, $R_1$ and $R_2$ together are =O;
$R_3$ is O⁻ or $OR_9$,
    where $R_9$ is H, methyl, ethyl or phenyl;
$R_4$ is

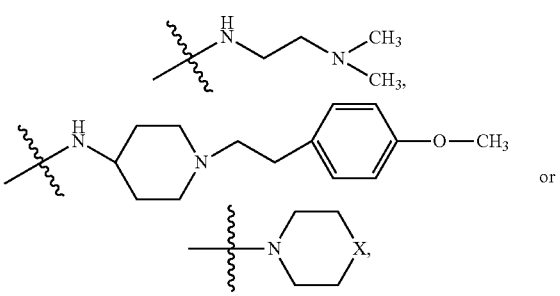

where X is O, S, $NR_{10}$, or $N^+R_{10}R_{10}$,
    where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

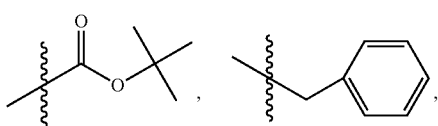

—CH$_2$CN, —CH$_2$CO$_2$R$_{11}$, —CH$_2$COR$_{11}$, —NHR$_{11}$ or —NH$^+$(R$_{11}$)$_2$,
  where R$_{11}$ is alkyl, alkenyl or alkynyl, each of which is substituted or unsubstituted, or H;

R$_5$ and R$_6$ taken together are =O; and

R$_7$ and R$_8$ is each independently H, F, Cl, Br, SO$_2$Ph, CO$_2$CH$_3$, or SR$_{12}$,
  where R$_{12}$ is a substituted or unsubstituted alkyl, alkenyl or alkynyl.

In an embodiment of the pharmaceutical composition, R$_3$ is O$^-$.

In an embodiment of the pharmaceutical composition, R$_4$ is

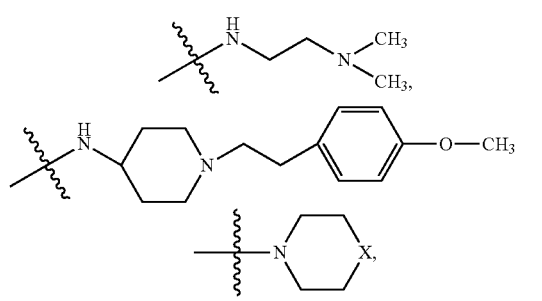

where X is O, NR$_{10}$, N$^+$R$_{10}$R$_{10}$
  where each R$_{10}$ is independently H, alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

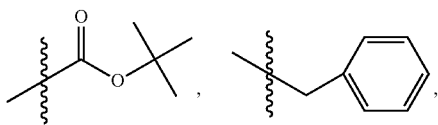

—CH$_2$CN, —CH$_2$CO$_2$R$_{11}$, —CH$_2$COR$_{11}$, —NHR$_{11}$ or —NH$^+$(R$_{11}$)$_2$, where R$_{11}$ is H or alkyl.

In an embodiment of the pharmaceutical composition, the protein phosphatase inhibitor 2A has the structure

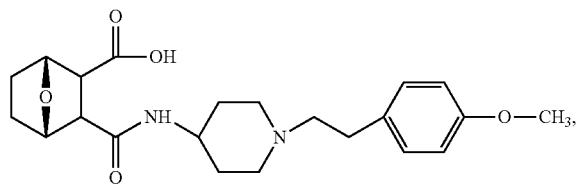

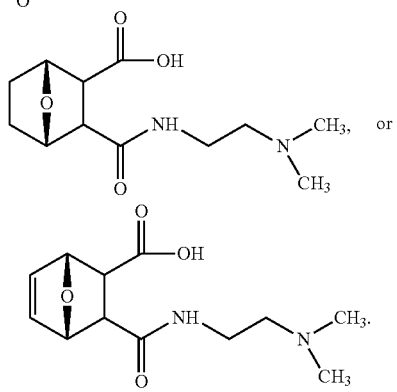

In an embodiment of the pharmaceutical composition, R$_4$ is

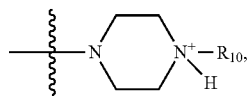

where R$_{10}$ is R$_{10}$H, alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,

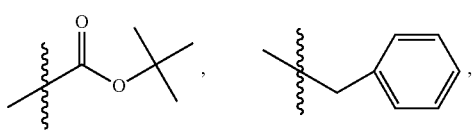

—CH$_2$CN, —CH$_2$CO$_2$R$_{11}$, —CH$_2$COR$_{11}$, —NHR$_{11}$ or —NH$^+$(R$_{22}$)$_2$, where R$_{11}$ is H or alkyl.

In an embodiment of the pharmaceutical composition, R$_4$ is

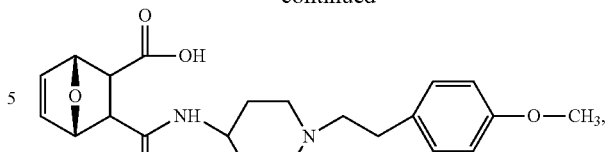

In an embodiment of the pharmaceutical composition, R$_4$ is

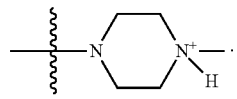

where $R_{10}$ is

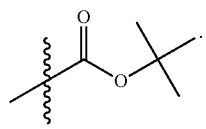 [SMILES: *C(=O)OC(C)(C)C]

In an embodiment of the pharmaceutical composition, $R_4$ is

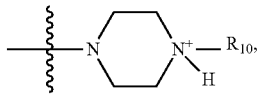

where $R_{10}$ is

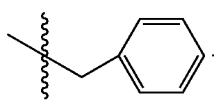

In an embodiment of the pharmaceutical composition, $R_4$ is

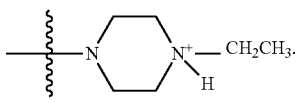

In an embodiment of the pharmaceutical composition, $R_4$ is

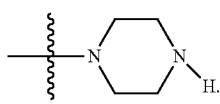

In an embodiment of the pharmaceutical composition, $R_5$ and $R_6$ together are =O.

In an embodiment of the pharmaceutical composition, $R_7$ and $R_8$ are each H.

In an embodiment of the pharmaceutical composition, the protein phosphatase 2A inhibitor has the structure

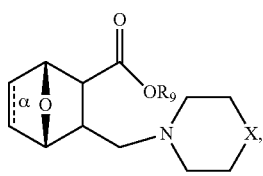

wherein bond α is present or absent; $R_9$ is present or absent and when present is H, $C_1$-$C_{10}$ alkyl, $C_2$-$C_{10}$ alkenyl or phenyl; and X is O, S, $NR_{10}$ or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

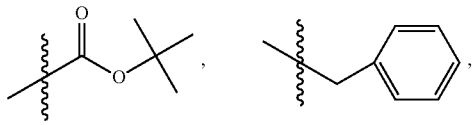

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substitutent that is a precursor to an aziridinyl intermediate, or a salt, zwitterion or enantiomer of the compound.

In an embodiment of the pharmaceutical composition, the protein phosphatase 2A inhibitor has the structure

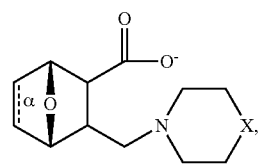

wherein,
bond α is present or absent;
X is O, S, $NR_{10}$ or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

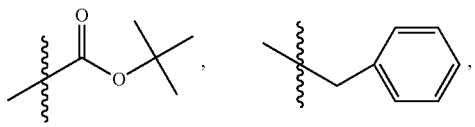

—$CH_2CO_2R_{11}$, —$CH_2COR_{11}$, —$CH_2CN$, or —$CH_2CH_2R_{16}$, where $R_{11}$ is H or alkyl, and where $R_{16}$ is any substitutent that is a aziridinyl intermediate, or a salt, zwitterion or enantiomer of the compound.

In an embodiment of the pharmaceutical composition, X is O or $NH^+R_{10}$,
where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

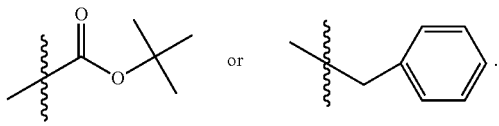

In an embodiment of the pharmaceutical composition, X is —$CH_2CH_2R_{16}$, where $R_{16}$ is any substitutent that is a precursor to an aziridinyl intermediate.

In an embodiment of the pharmaceutical composition, X is O.

In an embodiment of the pharmaceutical composition, X is $NH^+R_{10}$,
where $R_{10}$H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

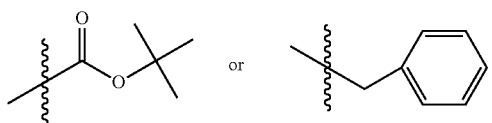 or

In an embodiment of the pharmaceutical composition, $R_{10}$ is methyl.

In an embodiment of the pharmaceutical composition, $R_{10}$ is

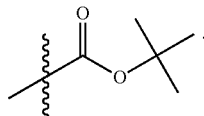

In an embodiment of the pharmaceutical composition, $R_{10}$ is

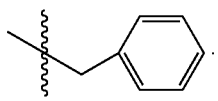

In an embodiment of the pharmaceutical composition, $R_{10}$ is ethyl.

In an embodiment of the pharmaceutical composition, $R_{10}$ is absent.

In an embodiment of the pharmaceutical composition, the protein phosphatase 2A inhibitor has the structure

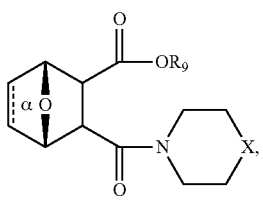

wherein
bond α is present or absent;
$R_9$ is present or absent and when present is H, alkyl, alkenyl, alkynyl or phenyl; and
X is O, $NR_{10}$, or $N^+R_{10}R_{10}$,
  where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

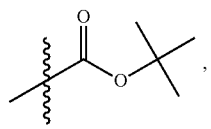 [SMILES: *C(=O)OC(C)(C)C] , 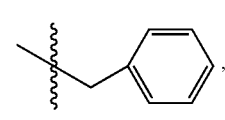 ,

—$CH_2CN$, —$CH_2CO_2R_{12}$, or —$CH_2COR_{12}$, where $R_{12}$ is H or alkyl,
or a salt, zwitterion, or enantiomer of the compound.

In an embodiment of the pharmaceutical composition, the protein phosphatase 2A inhibitor has the structure

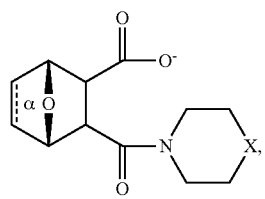

wherein
bond α is present or absent;
X is O or $NH^+R_{10}$,
  where $R_{10}$ is H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

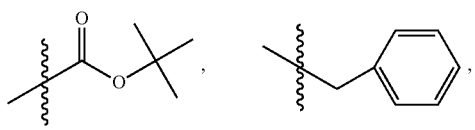

—$CH_2CN$, —$CH_2CO_2R_{22}$, or —$CH_2COR_{12}$, where $R_{12}$ is H or alkyl.

In an embodiment of the pharmaceutical composition, bond α is present.

In an embodiment of the pharmaceutical composition, bond α is absent.

In an embodiment of the pharmaceutical composition, the protein phosphatase 2A inhibitor has the structure

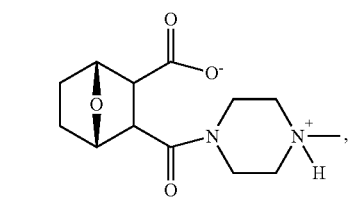

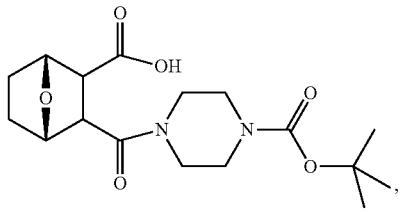

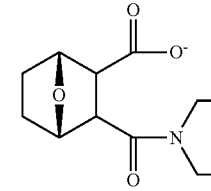

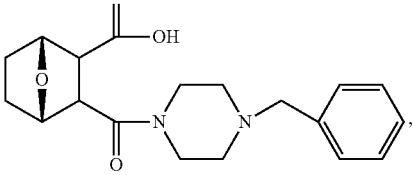

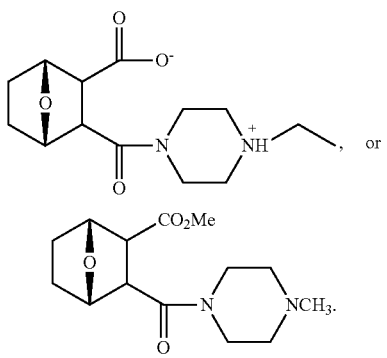

In an embodiment of the pharmaceutical composition, the protein phosphatase 2A inhibitor has the structure

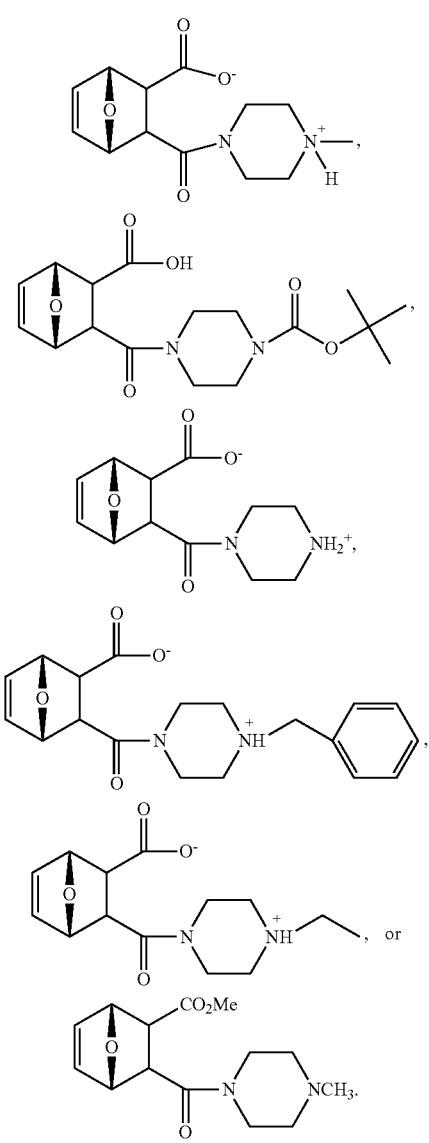

In an embodiment of the pharmaceutical composition, the protein phosphatase 2A inhibitor has the structure

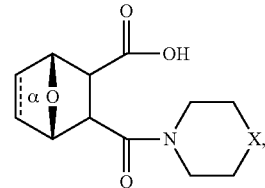

wherein
bond α is present or absent; X is $NH^+R_{10}$,
where $R_{10}$ is present or absent and when present $R_{10}$ is alkyl, substituted $C_2$-$C_{12}$ alkyl, alkenyl, substituted $C_4$-$C_{12}$ alkenyl,

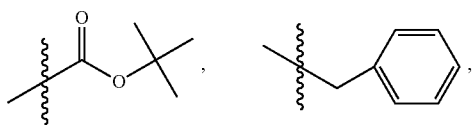

—$CH_2CN$, —$CH_2CO_2R_{12}$, or —$CH_2COR_{12}$, where $R_{12}$ is H or alkyl.

In an embodiment of the pharmaceutical composition, the protein phosphatase 2A inhibitor has the structure

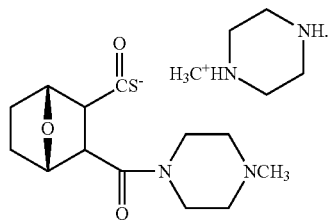

In an embodiment of the pharmaceutical composition, the protein phosphatase 2A inhibitor has the structure

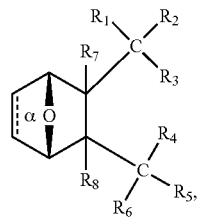

wherein
bond α is present or absent;
$R_1$ and $R_2$ is each independently H, $O^-$ or $OR_9$,
where $R_9$ is H, alkyl, substituted alkyl, alkenyl, alkynyl or aryl,
or $R_1$ and $R_2$ together are =O;
$R_3$ and $R_4$ are each different, and each is $O(CH_2)_{1-6}R_9$ or $OR_{10}$, or

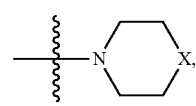

where X is O, S, $NR_{11}$, or $N^+R_{11}R_{11}$,
  where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

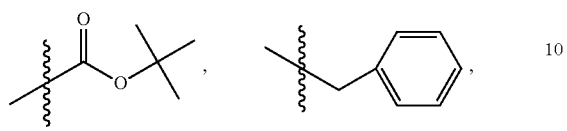

—$CH_2CN$,   —$CH_2CO_2R_{12}$,   —$CH_2COR_{12}$,
—$NHR_{12}$ or —$NH^+(R_{12})_2$,
  where each $R_{12}$ is independently alkyl, alkenyl or alkynyl, each of which is substituted or unsubstituted, or H;
where $R_{10}$ is substituted alkyl, substituted alkenyl, substituted alkynyl, or substituted aryl,
or $R_3$ and $R_4$ are each different and each is OH or

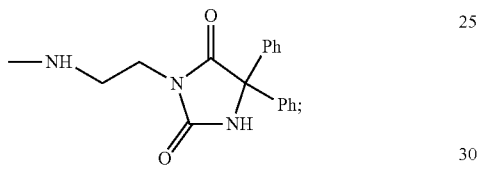

$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{13}$,
  where $R_{13}$ is H, aryl or a substituted or unsubstituted alkyl, alkenyl or alkynyl,
or a salt, enantiomer or zwitterion of the compound.
In an embodiment of the pharmaceutical composition, the protein phosphatase 2A inhibitor has the structure

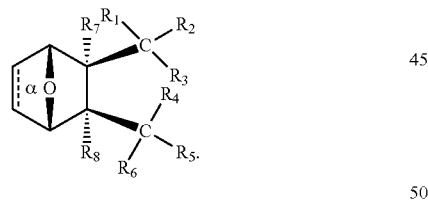

In an embodiment of the pharmaceutical composition, bond α is present.
In an embodiment of the pharmaceutical composition, bond α is absent.
In an embodiment of the pharmaceutical composition, $R_3$ is $OR_9$ or $O(CH_2)_{1-6}R_{10}$;
  where $R_9$ is aryl or substituted ethyl;
  where $R_{10}$ is substituted phenyl, wherein the substituent is in the para position;
$R_4$ is

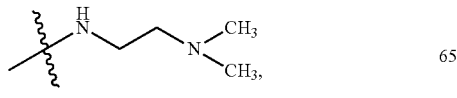

-continued

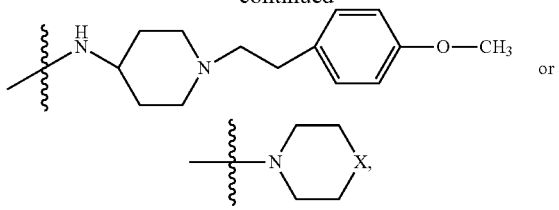

where X is O, S, $NR_{11}$, or $N^+R_{11}R_{11}$,
  where each $R_{11}$ is independently H, alkyl, hydroxyalkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro,

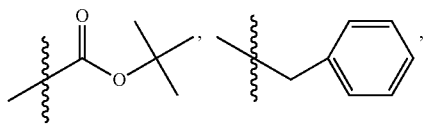

—$CH_2CN$,   —$CH_2CO_2R_{12}$,   —$CH_2COR_{12}$,
—$NHR_{12}$ or —$NH^+(R_{12})_2$,
  where $R_{12}$ is alkyl, alkenyl or alkynyl, each of which is substituted or unsubstituted, or H;
or where $R_3$ is OH and $R_4$ is

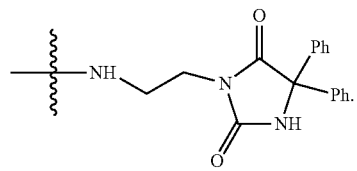 [SMILES: *NCCN1C(=O)NC(c2ccccc2)(c2ccccc2)C1=O]

In an embodiment of the pharmaceutical composition, $R_4$ is

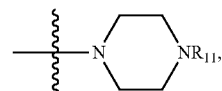

where $R_{11}$ is alkyl or hydroxylalkyl
or $R_4$ is

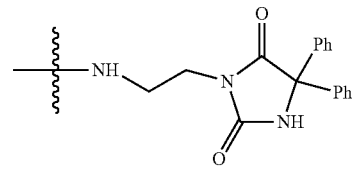 [SMILES: *NCCN1C(=O)NC(c2ccccc2)(c2ccccc2)C1=O]

when $R_3$ is OH.
In an embodiment of the pharmaceutical composition,
$R_1$ and $R_2$ together are =O;
$R_3$ is $OR_9$ or $OR_{10}$ or $O(CH_2)_{1-2}R_9$,
  where $R_9$ is aryl or substituted ethyl;
  where $R_{10}$ is substituted phenyl, wherein the substituent is in the para position;

or R₃ is OH and R₄ is

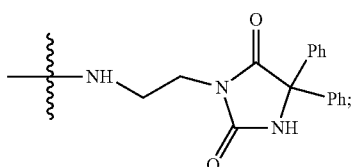

R₄ is

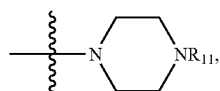

where $R_{11}$ is alkyl or hydroxyl alkyl;
$R_5$ and $R_6$ together are =O; and
$R_7$ and $R_8$ are each independently H.
In an embodiment of the pharmaceutical composition,
$R_1$ and $R_2$ together are =O;
$R_3$ is OH, O(CH₂)R₉, or OR₁₀,
  where $R_9$ is phenyl;
  where $R_{10}$ is CH₂CCl₃,

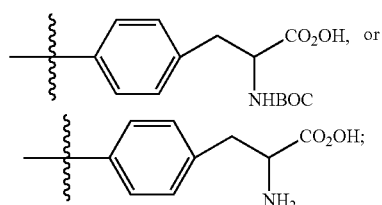

R₄ is

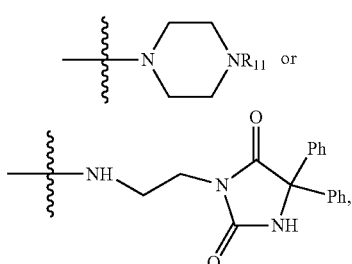

where $R_{11}$ is CH₃ or CH₃CH₂OH;
$R_5$ and $R_6$ together are =O; and
$R_7$ and $R_8$ are each independently H.
In an embodiment of the pharmaceutical composition, $R_3$ is $OR_{10}$, where $R_{10}$ is (CH₂)₁₋₆(CHNHBOC)CO₂H, (CH₂)₁₋₆(CHNH₂)CO₂H, or (CH₂)₁₋₆CCl₃.
In an embodiment of the pharmaceutical composition, $R_{10}$ is CH₂(CHNHBOC)CO₂H.
In an embodiment of the pharmaceutical composition, $R_{10}$ is CH₂(CHNH₂)CO₂H.
In an embodiment of the pharmaceutical composition, $R_{10}$ is CH₂CCl₃.
In an embodiment of the pharmaceutical composition, $R_3$ is O(CH₂)₁₋₆R₉ where $R_9$ is phenyl.

In an embodiment of the pharmaceutical composition, $R_3$ is O(CH₂)R₉ where $R_9$ is phenyl.
In an embodiment of the pharmaceutical composition, $R_3$ is OH and $R_4$ is

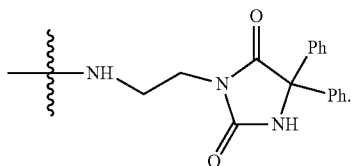

In an embodiment of the pharmaceutical composition, $R_4$ is

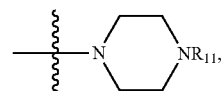

wherein $R_{11}$ is hydroxyalkyl.
In an embodiment of the pharmaceutical composition, $R_{11}$ is —CH₂CH₂OH.
In an embodiment of the pharmaceutical composition, $R_4$ is

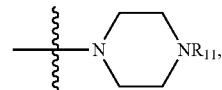

wherein $R_{11}$ is alkyl.
In an embodiment of the pharmaceutical composition, $R_{11}$ is —CH₃.
In an embodiment of the pharmaceutical composition, $R_4$ is

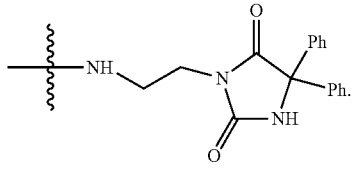 [SMILES: *NCCN1C(=O)NC(c2ccccc2)(c2ccccc2)C1=O]

In an embodiment of the pharmaceutical composition, the protein phosphatase 2A inhibitor has the structure

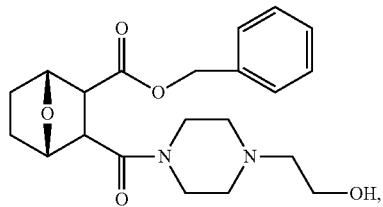

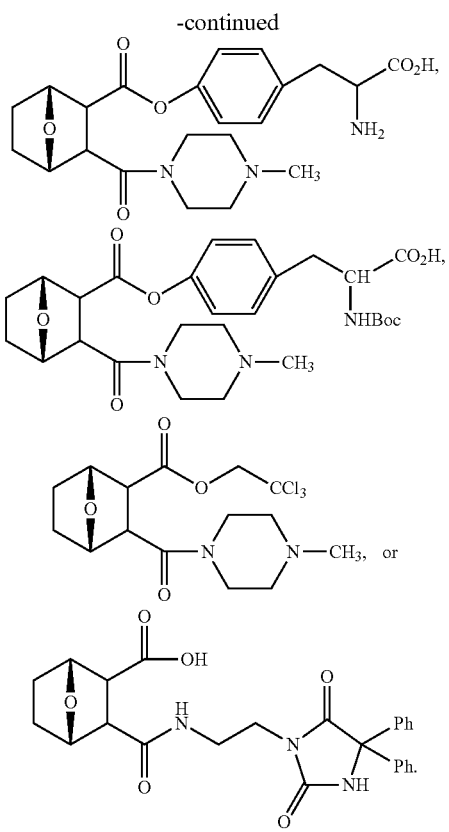

In an embodiment of the pharmaceutical composition, the protein phosphatase 2A inhibitor has the structure

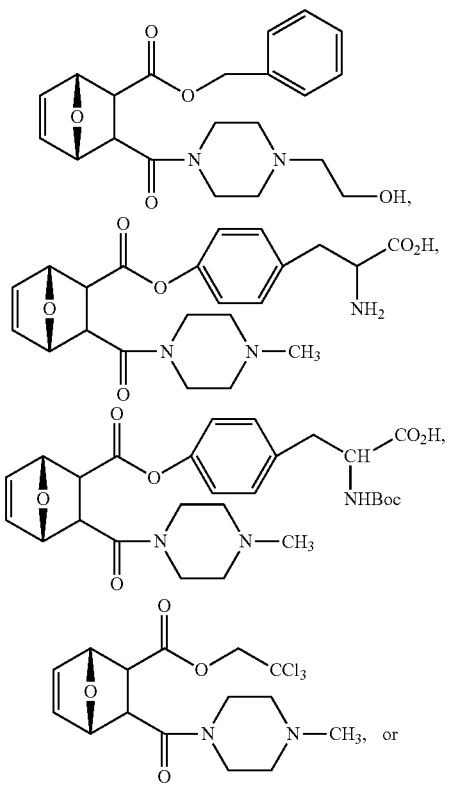

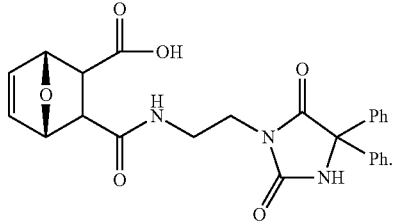

In an embodiment of the pharmaceutical composition, the protein phosphatase 2A inhibitor has the structure

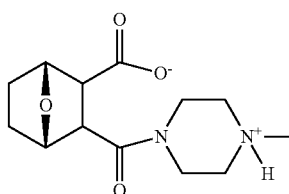

or a salt or enantiomer thereof.

In an embodiment of the pharmaceutical composition, the pharmaceutical composition further comprises water.

In an embodiment, the pH of the pharmaceutical composition is 10-11.

In an embodiment, the pH of the pharmaceutical composition is 10.4-10.6.

In an embodiment, the pH of the pharmaceutical composition is 10.5.

In an embodiment of the pharmaceutical composition, the protein phosphatase 2A inhibitor is present in the pharmaceutical composition at a concentration of 1.0 mg/mL.

In an embodiment of the pharmaceutical composition, the monosodium glutamate is present in the pharmaceutical composition at a concentration of 0.1 M.

The invention also provides a sealed package comprising a pharmaceutical composition of the invention.

In an embodiment, the sealed package is a vial.

In an embodiment, the sealed package comprises 10 mL of the pharmaceutical composition.

The invention also provides a method of preparing a pharmaceutical composition for administration to a subject, comprising mixing an amount of the pharmaceutical composition of the invention with a saline solution.

The invention also provides a method of preparing a pharmaceutical composition for administration to a subject, comprising removing an amount of pharmaceutical composition from the sealed package of the invention and mixing the amount of the pharmaceutical composition with a saline solution.

In an embodiment of the methods, the amount of the saline solution is mL.

In an embodiment of the methods, the saline solution contains an anti-cancer cancer agent which is not LB-100.

In an embodiment of the methods, the saline solution contains a pharmaceutically acceptable carrier.

The invention also provides a pharmaceutical composition produced by the above methods.

The invention also provides a method of making the pharmaceutical composition of the invention, comprising (a) adding an amount of monosodium glutamate to an amount of water to form a mixture of monosodium glutamate and water, and (b) adding an amount of a protein phosphatase 2 inhibitor to the mixture.

In an embodiment, the method further comprises a step of adjusting the pH of the mixture after step (a), a step or adjusting the pH of the mixture after step (b), or a step of adjusting the pH of the mixture after step (a) and a step of adjusting the pH of the mixture after step (b), wherein the pH of the mixture is adjusted to a pH range of 10-11 in each pH adjusting step.

In an embodiment, the pH of the mixture is adjusted to a pH range of in each pH adjusting step.

In an embodiment, the pH of the mixture is adjusted to 10.5 in the final pH adjustment step.

In an embodiment, the pH of the mixture is adjusted with one or both of sodium hydroxide and hydrochloric acid.

In an embodiment, the methods of making the pharmaceutical composition of the invention further comprise a final step of sterile filtering the mixture.

The invention also provides a pharmaceutical composition produced by any of the above methods.

The invention also provides a method of treating a subject afflicted with a condition or disease amenable to treatment with a PP2A inhibitor comprising administering to the subject a pharmaceutical composition of the invention in an amount effective to treat the subject.

The invention also provides a method of treating a subject afflicted with cancer comprising administering to the subject a pharmaceutical composition of the invention in an amount effective to treat the subject.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promyelocytic leukemia, prostate carcinoma, rectal cancer, renal cancer, soft tissue sarcoma, small cell lung cancer, stomach cancer, thyroid cancer and throat cancer.

In an embodiment, cells of the cancer overexpress N-CoR.

In an embodiment, cells of the cancer do not overexpress N-CoR.

In an embodiment, cells of the cancer overexpress TCTP.

In an embodiment, the method further comprises administering to the subject an anti-cancer agent in an amount such that the amount of the pharmaceutical composition and the amount of anti-cancer agent together are effective to treat the subject.

In an embodiment, the anti-cancer agent is a chemotherapeutic agent, a DNA intercalating agent, a spindle poison or a DNA damaging agent.

In an embodiment, the anti-cancer agent is docetaxel.

In an embodiment, the method further comprises administering to the subject an amount of ionizing radiation such that the amount of the pharmaceutical composition and the amount of the ionizing radiation together are effective to treat the subject.

In an embodiment, the method further comprises administering a retinoid receptor ligand in an amount such that the amount of the pharmaceutical composition and the amount of the retinoid receptor ligand together are effective to treat the subject. In an embodiment, the retinoid receptor ligand may be a retinoid, such as a retinoic acid, e.g. cis retinoic acid or trans retinoic acid. The cis retinoic acid may be 13-cis retinoic acid and the trans retinoic acid may be all-trans retinoic acid. In an embodiment, the retinoic acid is all-trans retinoic acid (ATRA).

Retinoid receptor ligands used in the method of the invention include vitamin A (retinol) and all its natural and synthetic derivatives (retinoids).

In an embodiment, the method further comprises administering a histone deacetylase ligand in an amount such that the amount the pharmaceutical composition and the amount of the histone deacetylase ligand together are effective to treat the subject.

In an embodiment, the histone deacetylase ligand may be an inhibitor, e.g. the histone deacetylase inhibitor HDAC-3 (histone deacetylase-3). The histone deacetylase ligand may also be selected from the group consisting of 2-amino-8-oxo-9,10-epoxy-decanoyl, 3-(4-aroyl-1H-pyrrol-2-yl)-N-hydroxy-2-propenamide, APHA Compound 8, apicidin, arginine butyrate, butyric acid, depsipeptide, depudecin, HDAC-3, m-carboxycinnamic acid bis-hydroxamide, N-(2-aminophenyl)-4-[N-(pyridin-3-ylmethoxycarbonyl) aminomethyl] benzamide, MS 275, oxamflatin, phenylbutyrate, pyroxamide, scriptaid, sirtinol, sodium butyrate, suberic bishydroxamic acid, suberoylanilide hydroxamic acid, trichostatin A, trapoxin A, trapoxin B and valproic acid. In another embodiment of the invention, the inhibitor is valproic acid.

In an embodiment, the method further comprises administering both a retinoid receptor ligand and a histone deacetylase ligand each in an amount such that the amount of the pharmaceutical composition, the amount of the histone deacetylase ligand and the amount of the retinoid receptor ligand together are effective to treat the subject.

The invention also provides a method of treating a subject afflicted with a neurodegenerative disease comprising administering to the subject a pharmaceutical composition of the invention in an amount effective to treat the subject.

In an embodiment, the neurodegenerative disease is Alzheimer's disease, Mild Cognitive Impairment, Parkinsons Disease, Frontotemporal Dementia, Dementia, or Lewy Body Dementia.

In an embodiment, the method further comprises administering to the subject an NMDA receptor antagonist, an acetylcholinesterase inhibitor, an anti-amyloid antibody, a 5-HT6 antagonist, a gamma secretase inhibitor, a beta secretase inhibitor, an inhibitor of aggregation of amyloid-$\beta$ peptide, or a tau aggregation inhibitor.

The invention also provides a method of treating a subject afflicted with a disease characterized by a loss of protein function caused by a genetic abnormality associated with the disease comprising administering to the subject a therapeutically effective amount of a pharmaceutical composition of the invention.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocirne Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

In an embodiment, the method further comprises administering to the subject an amount of a histone deacetylase inhibitor such that the amount of the pharmaceutical composition and the amount of histone deacetylase inhibitor together are effective to treat the subject.

The invention also provides a method of reducing reperfusion injury in a subject comprising administering to the subject a therapeutically effective amount of a pharmaceutical composition of the invention.

The invention also provides a method of reducing tissue damage associated with reperfusion injury in a subject comprising administering to the subject a therapeutically effective amount of a pharmaceutical composition of the invention.

In an embodiment, the subject has suffered an ischemia.

In an embodiment, the ischemia is caused by a myocardial infarction, stroke, or sepsis.

In an embodiment, the tissue is myocardial tissue, brain tissue, or endothelial tissue.

The invention also provides a method of reducing vascular leakage associated with reperfusion injury in a subject suffering from sepsis comprising administering to the subject a therapeutically effective amount of a pharmaceutical composition of the invention.

The invention also provides a method of reducing tissue damage due to an acute trauma in a subject comprising administering to the subject a therapeutically effective amount of a pharmaceutical composition of the invention.

The invention also provides a method of reducing vascular leakage due to an acute trauma in a subject, comprising administering to the subject a therapeutically effective amount of a pharmaceutical composition of the invention.

In an embodiment of the above methods, the pharmaceutical composition is administered intravenously.

In an embodiment of the above methods, the amount of LB-100 administered is 1 mg to 12 mg per dose.

The invention also provides a pharmaceutical composition as described herein for use in treating a subject afflicted with a condition or disease amenable to treatment with a PP2A inhibitor.

The invention also provides a pharmaceutical composition as described herein for use in treating a subject afflicted with cancer.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promylocytic leukemia, prostate carcinoma, rectal cancer, renal cancer, soft tissue sarcoma, small cell lung cancer, stomach cancer, thyroid cancer and throat cancer.

The invention also provides a pharmaceutical composition as described herein for use in treating a subject afflicted with a neurodegenerative disease.

In an embodiment, the neurodegenerative disease is Alzheimer's disease, Mild Cognitive Impairment, Parkinsons Disease, Frontotemporal Dementia, Dementia, or Lewy Body Dementia.

The invention also provides a pharmaceutical composition as described herein for use in treating a subject afflicted with a disease characterized by a loss of protein function caused by a genetic abnormality associated with the disease.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocirne Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

The invention also provides a pharmaceutical composition as described herein for use in reducing reperfusion injury.

The invention also provides a pharmaceutical composition as described herein for use in reducing tissue damage associated with reperfusion injury.

The invention also provides a pharmaceutical composition as described herein for use in reducing vascular leakage associated with reperfusion injury in a subject suffering from sepsis.

The invention also provides a pharmaceutical composition as described herein for use in reducing tissue damage due to an acute trauma.

The invention also provides a pharmaceutical composition as described herein for use in reducing vascular leakage due to an acute trauma.

The subject invention also provides the use of the pharmaceutical composition for the manufacture of a medicament for treating a subject afflicted with a condition or disease amenable to treatment with a PP2A inhibitor.

The subject invention also provides the use of the pharmaceutical composition for the manufacture of a medicament for treating a subject afflicted with cancer.

In an embodiment, the cancer is selected from acute lymphocytic leukemia, adenocarcinoma of the lung, adrenocortical cancer, bladder cancer, breast cancer, cervical cancer, chronic myelocytic leukemia, colon cancer, esophageal, gallbladder, glioblastoma multiforme, head and neck cancer, Hodgkin lymphoma, non-Hodgkin lymphoma, large cell lung cancer, liver cancer, medulloblastoma, melanoma, neuroblastoma, osteosarcoma, ovary adenocarcinoma, pancreatic cancer, promylocytic leukemia, prostate carcinoma, rectal cancer, renal cancer, soft tissue sarcoma, small cell lung cancer, stomach cancer, thyroid cancer and throat cancer.

The subject invention also provides the use of the pharmaceutical composition for the manufacture of a medicament for treating a subject afflicted with a neurodegenerative disease.

In an embodiment, the neurodegenerative disease is Alzheimer's disease, Mild Cognitive Impairment, Parkinsons Disease, Frontotemporal Dementia, Dementia, or Lewy Body Dementia.

The subject invention also provides the use of the pharmaceutical composition for the manufacture of a medicament for treating a subject afflicted with a disease characterized by a loss of protein function caused by a genetic abnormality associated with the disease.

In an embodiment, the disease is selected from Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocirne Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary Transthyretin (TTR) amyloidosis.

The subject invention also provides the use of the pharmaceutical composition for the manufacture of a medicament for reducing reperfusion injury.

The subject invention also provides the use of the pharmaceutical composition for the manufacture of a medicament for reducing tissue damage associated with reperfusion injury.

The subject invention also provides the use of the pharmaceutical composition for the manufacture of a medicament for reducing reperfusion injury in a subject suffering from sepsis.

The subject invention also provides the use of the pharmaceutical composition for the manufacture of a medicament for reducing tissue damage due to an acute trauma.

The subject invention also provides the use of the pharmaceutical composition for the manufacture of a medicament for reducing vascular leakage due to an acute trauma.

In an embodiment of the methods and uses described herein, the subject is a mammal. In an embodiment, the subject is a human.

The invention further contemplates the use of prodrugs which are converted in vivo to the PP2A inhibitor compounds described herein (see, e.g., R. B. Silverman, 1992, "The Organic Chemistry of Drug Design and Drug Action", Academic Press, Chapter 8, the entire contents of which are hereby incorporated by reference). Such prodrugs can be used to alter the biodistribution (e.g., to allow compounds which would not typically enter a reactive site) or the pharmacokinetics of the compound.

The compounds described in the present invention are in racemic form or as individual enantiomers. The enantiomers can be separated using known techniques, such as those described, for example, in Pure and Applied Chemistry 69, 1469-1474, (1997) IUPAC.

The pharmaceutical compositions described herein can be used to treat any of the conditions identified as being treatable with a PP2A inhibitor in any of PCT International Application Publication Nos. WO 2008/097561, WO 2009/020565, WO 2010/014141, WO 2010/014220, WO 2010/014254, WO 2010/147612, and WO 2012/162535, and U.S. Provisional application No. 61/782,894. Similarly, the pharmaceutical compositions described herein can be used in any of the methods reciting a PP2A inhibitor and for any of the uses of PP2A inhibitors described in PCT International Application Publication Nos. WO 2008/097561, WO 2009/020565, WO 2010/014141, WO 2010/014220, WO 2010/014254, WO 2010/147612, and WO 2012/162535, and U.S. Provisional application No. 61/782,894.

For the foregoing embodiments, each embodiment disclosed herein is contemplated as being applicable to each of the other disclosed embodiments. Thus, all combinations of the various elements described herein are within the scope of the invention.

Definitions

As used herein, and unless otherwise stated, each of the following terms shall have the definition set forth below.

As used herein "LB-100" refers to the compound having the following structure:

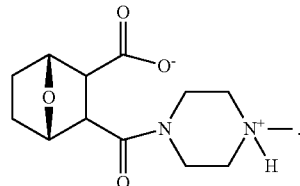

The chemical name of LB-100 is 3-(4-methylpiperazine-1-carbonyl)-7-oxabicyclo[2.2.1]heptane-2-carboxylic acid. LB-100 is also referred to as Compound 100 and LB1 in the art. Pharmaceutical compositions of the invention can comprise LB-100, or an enantiomer, or salt thereof.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , n−1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, . . . , n−1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2, . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be substituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "zwitterion" means a compound that is electrically neutral but carries formal positive and negative charges on different atoms. Zwitterions are polar, have high solubility in water and have poor solubility in most organic solvents.

As used herein, a "compound" is a small molecule that does not include proteins, peptides or amino acids.

As used herein, a "mixture" is material system made up of two or more different substances. Examples of mixtures include suspensions and solutions.

As used herein, an "isolated" compound is a compound isolated from a crude reaction mixture or from a natural source following an affirmative act of isolation. The act of isolation necessarily involves separating the compound from the other components of the mixture or natural source, with some impurities, unknown side products and residual amounts of the other components permitted to remain. Purification is an example of an affirmative act of isolation.

As used herein, "anti-cancer agent" means standard cancer regimens which are currently known in the art. Examples include, but are not limited to, x-radiation, ionizing radiation, DNA damaging agents, DNA intercalating agents, microtubule stabilizing agents, microtubule destabilizing agents, spindle toxins, and chemotherapeutic agents. Further examples include cancer regimens approved by the Food and Drug Administration, which include, but are not limited to, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, clyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, flurouracile, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, ruacil mustard, valrunicin, vinblastine, vincristine, vinorelbine, vorinostat, zoledronate, and zoledronic acid. A complete list of all FDA approved cancer drugs can be found at accessdata.fda.gov/scripts/cder/onctools/druglist.cfm.

Examples of DNA intercalating agents include, but are not limited to, doxorubicin, daunorubicin, dactinomycin. Examples of Spindle Poisons include, but are note limited to vincristine, vinblastine, taxol. DNA damaging agents include antracyclines, bleomycin, cisplatin, etoposide, temozolomide, and nitrosoureas.

As used herein, "treatment of a condition or disease" or "treating" encompasses inducing inhibition, regression, or stasis of a condition or disease.

As used herein, "inhibition" of a condition or disease in a subject means preventing or reducing the condition or disease progression and/or complication in the subject.

As used herein, a "saline solution" is a solution of NaCl in water. A saline solution can be sterile or non-sterile. A saline solution can have additional components in addition to NaCl and water, e.g. dextrose or other pharmaceutically acceptable excipient. In an embodiment, the saline solution used is "normal saline," a sterile solution of 0.9% w/v of NaCl in water.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Other injectable drug delivery systems include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

The compounds used in the pharmaceutical compositions and methods of the present invention may be in a salt form. As used herein, a "salt" is a salt of the instant compounds which has been modified by making acid or base salts of the compounds. In the case of compounds used to treat an infection or disease, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

As used herein, an "amount" or "dose" of an agent measured in milligrams refers to the milligrams of agent present in a drug product, regardless of the form of the drug product.

As used herein, the term "therapeutically effective amount" or "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "cancer cell" is a cell that is characterized by uncontrolled growth and cell division and can include tumor cells. Cancer cells, which can include tumor cells, may or may not overexpress N-CoR.

As used herein, "disease characterized by a loss of protein function" is any disease wherein loss of protein function is a factor in the cause and/or progression of the disease.

As used herein, a "loss of protein function disease" or a "loss of function disease" is a "disease characterized by a loss of protein function" as defined above.

Examples of a disease characterized by a loss of protein function include, but are not limited to, Gaucher's disease, von Hippel-Lindau disease, cystic fibrosis, Phenylketonuria, Fabry disease, Tay-Sachs disease, Pompe disease, Neimann-Pick disease (Type A, B and C), Marfan syndrome, Hemophilia A & B, retinitis pigmentosa, Neurofibromatosis Type 2, pheochromocytoma, paraganglioma, Multiple Endocirne Neoplasia Type 1, Familial Hypercholesterolemia, Hurler's disease, Hunter syndrome, Sanfilippo syndrome, Morquio syndrome, Maroteaux-Lamy syndrome, Sly syndrome, Sandhoff's disease, Fucosidosis, alpha-mannosidosis, beta-mannosidosis, aspartylglucosaminuria, Sialidosis, Inclusion-cell (I-cell) disease, Pseudo-Hurler polydystrophy, Krabbe's disease, Metachromatic leukodystrophy, multiple sulfatase deficiency, Wolmen's disease, Cholesteryl ester storage disease, Late onset GAA deficiency, Danon's disease, Neutropenia, X-linked hyper IgM syndrome, X-linked agammaglobulinemia, X-linked lymphoproliferative disease, Severe Combined Immunodeficiency, Noonan syndrome, juvenile myelomonocytic leukemia, Basal cell carcinoma, STAT1 deficiency, Alzheimer's disease, Parkinson's disease, Huntington's disease, TTR Amyloid Polyneuropathy, Ataxia Telangiectasia, Creutzfeldt-Jakob disease, Type II diabetes and Hereditary transthyretin (TTR) amyloidosis.

In particular, the invention is directed to a pharmaceutical composition for treating Gaucher's disease, von Hippel-Lindau disease, pheochromocytoma, and paraganglioma.

As used herein, "overexpressing N-CoR" means that the level of the Nuclear receptor co-repressor (N-CoR) expressed in cells of the tissue tested are elevated in comparison to the levels of N-CoR as measured in normal healthy cells of the same type of tissue under analogous conditions. The nuclear receptor co-repressor (N-CoR) of the subject invention may be any molecule that binds to the ligand binding domain of the DNA-bound thyroid hormone receptor (T3R) and retinoic acid receptor (RAR). (U.S. Pat. No. 6,949,624, Liu et al.) Examples of tumors that overexpress N-CoR may include glioblastoma multiforme, breast cancer (Myers et al.), colorectal cancer (Giannini and Cavallini), small cell lung carcinoma (Waters et al.) or ovarian cancer (Havrilesky et al.).

As used herein, "overexpressing TCTP" means that the level of TCTP expressed in cells of the tissued tested are elevated in comparison to the levels of TCTP as measure in normal healthy cells of the same type of tissued under analgous conditions.

As used herein, a "neurodegenerative disease" refers to a disease in which degeneration occurs of either gray or white matter, or both, of the nervous system. Thus, such a disease can be diabetic neuropathy, senile dementias, Alzheimer's disease, Mild Cognitive Impairment (MCI), dementia, Lewy Body Dementia, Frontal Temporal Lobe dementia, Parkinson's Disease, facial nerve (Bell's) palsy, glaucoma, Huntington's chorea, amyotrophic lateral sclerosis (ALS), status epilepticus, non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA and IgG gammapathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease and lipoproteinemia.

As used herein, "tauopathies" refers to a class of neurodegenerative diseases which result from aggregation of tau protein in neurofibrillary tangles. Examples of tauopathies include, but are not limited to, Alzheimer's disease, Frontotemproal dementia (Pick's disease), Progressive Supranuclear Palsy, and Corticobasal degeneration.

Where a range is given in the specification it is understood that the range includes all integers and 0.1 units within that range, and any sub-range thereof. For example, a range of 77 to 90% is a disclosure of 77, 78, 79, 80, and 81% etc.

Where a chemical name and a chemical structure conflict, the chemical structure shall govern.

All combinations of the various elements described herein are within the scope of the invention.

This invention will be better understood by reference to the following Example, but those skilled in the art will readily appreciate that the Example is only illustrative of the invention as described more fully in the claims which follow thereafter.

Example 1. Stability Study of LB-100 in Normal Saline and Sodium Bicarbonate 1.1 Objective To determine the stability of LB-100 in normal saline and 4.2% sodium bicarbonate formulations stored at room temperature and refrigerated.

1.2 Materials and Methods 1.2.1 Formulations

LB-100 (Ash Stevens, Inc., Riverview, MI) was stored refrigerated and was considered stable under this storage condition.

The vehicles used in preparation of the LB-100 formulations were normal saline (0.9% sodium chloride injection USP) (Baxter, Deerfield, IL) and 4.2% sodium bicarbonate, prepared by diluting sodium bicarbonate injection, 8.4% (Seneca Medical, Tiffin OH) 2-fold with Milli-Q water.

A normal saline formulation and a 4.2% sodium bicarbonate formulation were each prepared at a target LB-100 concentration of 1.00 mg/mL as follows. Approximately 20 mg of LB-100 was weighed in a tared glass vial. Vehicle was added to obtain the desired concentration, and the preparation was mixed as necessary to achieve complete dissolution of the test article.

1.2.2 Stability Testing

A normal saline formulation and a 4.2% sodium bicarbonate formulation, each prepared at a LB-100 concentration of 1.00 mg/mL were analyzed by HPLC/MS/MS to determine LB-100 concentration on the day of preparation. Aliquots of the formulations were stored at room temperature or refrigerated for 4, 8, 24, and 48 hours before being re-analyzed to assess LB-100 stability. The mean concentration and percent of time-zero values obtained are summarized in Table 1.

TABLE 1

| Storage Condition | Storage Duration (hours) | Mean Concentration, mg/mL (% of Time-Zero) | |
|---|---|---|---|
| | | Normal Saline Formulation (1.00 mg/mL) | 4.2% Sodium Bicarbonate Formulation (1.00 mg/mL) |
| Room Temperature | 4 | 0.751 (78.7) | 0.952 (96.3) |
| | 8 | 0.579 (60.6) | 0.921 (93.2) |
| | 24 | 0.199 (20.9) | 0.797 (80.7) |
| | 48 | 0.0553 (5.80) | 0.662 (67.0) |
| Refrigerated | 4 | 0.957 (100) | 1.01 (102) |
| | 8 | 0.967 (101) | 0.974 (98.6) |
| | 24 | 0.823 (86.3) | 0.970 (98.2) |
| | 48 | 0.795 (83.4) | 0.980 (99.2) |

1.3 Results

The normal saline formulation failed to meet the acceptance criteria (mean post-storage concentration 90% of the pre-storage value) following 4, 8, 24, and 48 hours of room temperature storage (78.7%, 60.6%, 20.9%, and 5.80% of the time-zero concentration, respectively) and following 24 and 48 hours of refrigerated storage (86.3% and 83.4% of the time-zero concentration, respectively). The sodium bicarbonate formulation failed to meet the acceptance criteria following 24 and 48 hours of room temperature storage (80.7% and 67.0% of the time-zero concentration, respectively).

1.4 Conclusions

An HPLC/MS/MS method for the determination of LB-100 concentration was used to assess test article stability in a normal saline formulation and in a 4.2% sodium bicarbonate formulation, each prepared at a target test article concentration of 1.00 mg/mL. The stability assessments were conducted following 4, 8, 24, and 48 hours of room temperature or refrigerated storage. The normal saline formulation failed to meet the acceptance criteria following 4, 8, 24, and 48 hours of room temperature storage and following 24 and 48 hours of refrigerated storage. The sodium bicarbonate formulation failed to meet the acceptance criteria following 24 and 48 hours of room temperature storage.

Example 2. Stability of LB-100 in Glutamate, Triethanolamine, and Phosphate Buffers 2.1 Objective To compare the long term storage stability of LB-100 in the following formulations:

1 mg/mL LB-100 in a glutamate buffer at pH 8.5±0.1;
1 mg/mL LB-100 in a glutamate buffer at pH 10.5±0.1;
1 mg/mL LB-100 in a triethanolamine buffer at pH 7.0±0.1;
1 mg/mL LB-100 in a triethanolamine buffer at pH 9.0±0.1; and
1 mg/mL LB-100 in a phosphate buffer at pH 8.0±0.1.

2.2 Materials and Methods 2.2.1 Formulations 2.2.1.1 0.1 M Glutamate Solution 28.1 g±0.1 g of L-glutamic acid monosodium salt monohydrate was weighed and added to 1500 mL of nanopure water. The mixture was mixed until all of the salt was dissolved to form a stock solution of 0.1 M L-glutamic acid monosodium salt monohydrate.

The pH of 750 mL of the L-glutamic acid monosodium salt monohydrate stock solution was adjusted to 8.5±0.1 using 0.1 N sodium hydroxide and/or 0.1 N hydrochloric acid, as necessary.

The pH of 750 mL of the L-glutamic acid monosodium salt monohydrate stock solution was adjusted to 10.5±0.1 using 0.1 N sodium hydroxide and/or 0.1 N hydrochloric acid, as necessary.

2.2.1.2 0.1 M Triethanolamine Solution 22.4 g±0.1 g of triethanolamine was weighed an added to 1500 mL of nanopure water. The mixture was mixed to form a 0.1 M triethanolamine stock solution.

The pH of 750 ml of the triethanolamine stock solution was adjusted to 7.0±0.1 using 0.1 N sodium hydroxide and/or 0.1 N hydrochloric acid, as necessary.

The pH of 750 ml of the triethanolamine stock solution was adjusted to 9.0±0.1 using 0.1 N sodium hydroxide and/or 0.1 N hydrochloric acid, as necessary.

2.2.1.3 0.1 M Phosphate Buffer 0.71 g±0.01 g of monosodium phosphate, monohydrate and 18.7±0.1 g disodium phosphate, heptahydrate were weighed and added to 750 mL of nanopure water. The mixture was mixed to form a solution 0.1 M phosphate buffer, pH 8.0±0.1.

2.2.1.4 LB-100 Formulations

For each of the buffer solutions above, 650 mL of a 1 mg/mL LB-100 solution was prepared by weighing and transferring 650 mg±10 mg of LB-100 (free acid) into a vessel containing 650 mL of the appropriate buffer. Using magnetic stirring, the mixtures were mixed until all LB-100 was completely dissolved. The pH of the solutions were checked and adjusted back into the stated range of the buffer, if necessary, using 0.1 N sodium hydroxide or 0.1 N hydrochloric acid. The solutions were filtered through a 0.22 μm nylon membrane filter.

2.2.2 Filling and Storage of Vials

Using USP type I glass vials and teflon stoppers, 50 vials were filled for each solution. The vials were stored according to the conditions of Table 2.

TABLE 2

| Storage Condition | Orientation | Number of Vials |
|---|---|---|
| 25° C./60% | Upright | 5 |
| 25° C./60% | Inverted | 5 |
| 2 to 8° C. | Upright | 12 |
| 2 to 8° C. | Inverted | 12 |
| −20° C. | Upright | 12 |
| −20° C. | Inverted | 12 |

2.3 Results 2.3.1 Analysis at 1 Month

LB-100 concentrations were measured by HPLC at time zero and one month. Samples were visually inspected for the presence of particulates. Time zero results are shown in Table 3. One month results are shown in Tables 4-7.

TABLE 3

| Formulation | Analyzed Conc. (mg/mL) | Analyzed Conc. (mean) | Mean Conc. Percent of Target | Visual Observation |
|---|---|---|---|---|
| Glutamate Buffer, pH 8.5 ± 0.1 | 0.959 1.02 | 0.991 | 99.1 | No particulates No particulates |

TABLE 3-continued

| Formulation | Analyzed Conc. (mg/mL) | Analyzed Conc. (mean) | Mean Conc. Percent of Target | Visual Observation |
|---|---|---|---|---|
| Glutamate Buffer, pH 10.5 ± 0.1 | 1.15<br>1.18 | 1.17 | 117 | No particulates<br>No particulates |
| Triethanolamine Buffer, pH 7.0 ± 0.1 | 0.877<br>0.913 | 0.895 | 89.5 | No particulates<br>No particulates |
| Triethanolamine Buffer, pH 9.0 ± 0.1 | 1.19<br>1.14 | 1.16 | 116 | No particulates<br>No particulates |
| Phosphate Buffer, pH 8.0 ± 0.1 | 1.09<br>1.06 | 1.07 | 107 | No particulates<br>No particulates |

TABLE 4

| Formulation | Analyzed Conc. (mg/mL) | Percent of Target | Percent of Time Zero | Visual Observation |
|---|---|---|---|---|
| Glutamate Buffer, pH 8.5 ± 0.1, 25° C./60%, Upright | 0.00509 | 0.509 | 0.514 | No particulates |
| Glutamate Buffer, pH 10.5 ± 0.1, 25° C./60%, Upright | 0.88 | 88.0 | 75.5 | No particulates |
| Triethanolamine Buffer, pH 7.0 ± 0.1, 25° C./60%, Upright | 0.0718 | 7.18 | 8.03 | No particulates |
| Triethanolamine Buffer, pH 9.0 ± 0.1, 25° C./60%, Upright | 0.563 | 56.3 | 48.4 | No particulates |
| Phosphate Buffer, pH 8.0 ± 0.1, 25° C./60%, Upright | 0.287 | 28.7 | 26.7 | No particulates |

TABLE 5

| Formulation | Analyzed Conc. (mg/mL) | Percent of Target | Percent of Time Zero | Visual Observation |
|---|---|---|---|---|
| Glutamate Buffer, pH 8.5 ± 0.1, 25° C./60%, Inverted | .00353 | 0.353 | 0.356 | No particulates |
| Glutamate Buffer, pH 10.5 ± 0.1, 25° C./60%, Inverted | 0.950 | 95.0 | 81.5 | No particulates |
| Triethanolamine Buffer, pH 7.0 ± 0.1, 25° C./60%, Inverted | 0.0728 | 7.28 | 8.14 | No particulates |
| Triethanolamine Buffer, pH 9.0 ± 0.1, 25° C./60%, Inverted | 0.593 | 59.3 | 51.0 | No particulates |
| Phosphate Buffer, pH 8.0 ± 0.1, 25° C./60%, Inverted | 0.300 | 30.0 | 28.0 | No particulates |

TABLE 6

| Formulation | Analyzed Conc. (mg/mL) | Percent of Target | Percent of Time Zero | Visual Observation |
|---|---|---|---|---|
| Glutamate Buffer, pH 8.5 ± 0.1, 2-8° C., Upright | 0.704 | 70.4 | 71.0 | No particulates |
| Glutamate Buffer, pH 10.5 ± 0.1, 2-8° C., Upright | 0.978 | 97.8 | 83.9 | No particulates |
| Triethanolamine Buffer, pH 7.0 ± 0.1, 2-8° C., Upright | 0.372 | 37.2 | 41.6 | No particulates |
| Triethanolamine Buffer, pH 9.0 ± 0.1, 2-8° C., Upright | 0.975 | 97.5 | 83.8 | No particulates |
| Phosphate Buffer, pH 8.0 ± 0.1, 2-8° C., Upright | 0.864 | 86.4 | 80.5 | No particulates |

TABLE 7

| Formulation | Analyzed Conc. (mg/mL) | Percent of Target | Percent of Time Zero | Visual Observation |
|---|---|---|---|---|
| Glutamate Buffer, pH 8.5 ± 0.1, 2-8° C., Inverted | 0.645 | 64.5 | 65.1 | No particulates |
| Glutamate Buffer, pH 10.5 ± 0.1, 2-8° C., Inverted | 0.985 | 98.5 | 84.5 | No particulates |
| Triethanolamine Buffer, pH 7.0 ± 0.1, 2-8° C., Inverted | 0.374 | 37.4 | 41.8 | No particulates |
| Triethanolamine Buffer, pH 9.0 ± 0.1, 2-8° C., Inverted | 0.909 | 90.9 | 78.1 | No particulates |
| Phosphate Buffer, pH 8.0 ± 0.1, 2-8° C., Inverted | 0.838 | 83.8 | 78.1 | No particulates |

2.3.2 Analysis at 3 Months

LB-100 concentrations were measured by HPLC at three months for the top two performing formulations at one month (glutamate buffer, pH and triethanolamine buffer, pH 9.0). Three month results for these formulations are shown in Table 8.

2.4 Discussion

Glutamate buffer, pH 10.5 was the clear standout among the tested formulations. The formulation of 1 mg/mL LB-100 in monosodium glutamate, pH 10.5, showed superior storage stability at one and three months at 25° C. and 2-8° C., and retained LB-100 potency up to and including 9 months of storage at −20° C.

TABLE 8

| Formulation | Analyzed Conc. (mg/mL) | Analyzed Conc. (mean) | Mean Conc. Percent of Target | Visual Observation |
|---|---|---|---|---|
| Glutamate Buffer, pH 10.5 ± 0.1, 2-8° C. | 1.00<br>1.01 | 1.00 | 98.3 | Particulates were present |
| Triethanolamine Buffer, pH 9.0 ± 0.1, 2-8° C. | 0.858<br>0.783 | 0.820 | 81.1 | Particulates were present |
| Glutamate Buffer, pH 10.5 ± 0.1, −20° C. | 1.04<br>1.04 | 1.04 | 102 | No particulates |
| Triethanolamine Buffer, pH 9.0 ± 0.1, −20° C. | 0.982<br>0.914 | 0.948 | 93.8 | No particulates |

2.3.3 Analysis of Glutamate Buffer, pH 10.5 at 9 Months

The top performing formulation at 1 and 3 months (1 mg/mL LB-100 in 0.1 M glutamate buffer, pH 10.5) was selected for further analysis. Properties of the formulation following 1 month of storage at 5° C.±3° C. are shown in Table 9. Properties of the formulation following 1, 3, 6, and 9 months of storage at −20° C.±10° C. are shown in Table 10. A representative HPLC chromatogram of the formulation at 9 months is shown in FIG. 1.

TABLE 9

| Test | Initial Time Point | 1-Month Time Point |
|---|---|---|
| Appearance | Clear liquid free of any visible particulates | Clear liquid free of any visible particulate |
| pH | 10.3 | 10.4 |
| Assay by HPLC | 102.5% | 101.9% |
| Sterility (bacterial endotoxin) | Meets USP 34 | n/a[1] |
| Particulate Matter | Meets USP 34 | n/a[1] |

[1]Testing not performed

Example 3. Pharmaceutical Composition Comprising LB-100

The following protocol is used to make 42 L of a pharmaceutical composition comprising 1 mg/mL LB-100 and 0.1M monosodium glutamate, pH 10.5.

3.1 Materials

TABLE 11

| Formulation Ingredients | |
|---|---|
| Component | Amount |
| Sodium-L-Glutamate Monohydrate FCC, NF | 785.9 g |
| 5N Hydrochloric Acid, NF | As needed to adjust pH |
| 5N Sodium Hydroxide, NF | As needed to adjust pH |
| LB-100 | 42.00 g* |
| Sterile Water for Injection, USP | 42.5 kg** |

*Theoretical weight of LB-100 required. The actual amount of LB-100 added from a given lot should be determined based upon purity and moisture content of the lot.
**Batch size of 42,000 mL adjusted for formulation density of 1.012 g/mL

TABLE 10

| Test | Initial Time Point | 1-Month Time Point | 3-Month Time Point | 6-Month Time Point | 9-Month Time Point |
|---|---|---|---|---|---|
| Appearance | Clear liquid free of any visible particulates | Clear liquid free of any visible particulates | Clear liquid free of any visible particulates | Clear liquid free of any visible particulates | Clear liquid free of any visible particulates |
| pH | 10.3 | 10.4 | 10.4 | 10.4 | 10.3 |
| Assay by HPLC | 102.5% | 102.7% | 103.9% | 101.3% | 101.1% |
| Sterility (bacterial endotoxin) | Meets USP 34 | n/a[1] | n/a[1] | n/a[1] | n/a[1] |
| Particulate Matter | Meets USP 34 | n/a[1] | n/a[1] | n/a[1] | n/a[1] |
| Impurities by HPLC | n/a[1] | n/a[1] | <LOQ[2] | <LOQ[2] | <LOQ[2] |

[1]Testing not performed;
[2]LOQ (Limit of Quantitation) = 2%

TABLE 12

Container and Closure Components

| Component | Type |
|---|---|
| Vial | 10 mL clear, 20 mm opening, USP Type 1 glass (Wheaton 223739) |
| Stopper | 20 mm, 4416/50, gray butyl, Teflon ®-2 coated (West 1014-4937) |
| Seal | 20 mm, 3766 white, 8-bridge flip-off (West 5420-3028) |

TABLE 13

Filter & Tubing Components

| Component | Type |
|---|---|
| Solution Filter | 4 inch Opticap, 0.22 micron Durapore ®, sterile (Millipore KVGLS4HH3) |
| Peristaltic Pump Tubing | 0.375 inch ID × 0.625 inch OD, Pharma 50 Silastic ® (Dow Corning 3100499) |
| Filter Outlet Tubing | 0.375 inch ID × 0.563 inch OD, Pharma 50 Silastic ® (Dow Corning 3100481) |
| Flexicon 3.2 Tubing | 0.125 inch ID × 0.250 inch OD, Pharma 50 Silastic ® (Dow Corning 3100430) |

3.2 Formulation Manufacturing Process

Approximately 34 kg of the Sterile Water for Injection, USP is added to a 40 L glass carboy. The Sodium-L-Glutamate Monohydrate is then added to the carboy and mixed for a minimum of ten minutes. The pH of the resulting mixture is adjusted with the sodium hydroxide and/or hydrochloric acid to a pH within the range 10.4-10.6. The target pH for this pH adjustment step is 10.5. Mixing of the mixture is continued until all of the solids in the carboy are dissolved.

Next, the LB-100 is added to the carboy and mixed for a minimum of ten minutes or until all of the LB-100 is dissolved. The pH of the resulting mixture is adjusted with the sodium hydroxide and/or hydrochloric acid to a pH within the range 10.4-10.6. The target pH for this pH adjustment step is 10.5. Mixing of the mixture is continued until all of the solids in the carboy are dissolved.

Next, Sterile Water for Injection is added to the carboy to bring the total weight of the mixture to 42.5 kg. The mixture is stirred for a minimum of five minutes to give a solution of 1 mg/mL LB-100 in 0.1M monosodium glutamate, pH 10.5.

Next, the solution is sterile filtered using the solution filter to provide a sterile solution of 1 mg/mL LB-100 in 0.1M monosodium glutamate, pH 10.5.

Finally, the vials are each filled with approximately 10 mL of the sterile solution (10.63 g±0.21 g) and stoppered.

3.3 Discussion

The manufacturing process described in Example 3 allows for the production of 42 L of 1 mg/mL LB-100 in 0.1M monosodium glutamate, pH 10.5. Larger and smaller batches can be readily obtained by adjusting the amounts of components as necessary to obtain the desired batch size. It should be appreciated that variations in the above-described steps may be necessary when adjusting the batch size, e.g. necessary mixing times may be longer or shorter depending upon batch size and equipment used to prepare the batch.

The pharmaceutical composition comprising 1 mg/mL LB-100 in 0.1M monosodium glutamate, pH 10.5, made by the process of Example 3 is stable for months at −20° C. and for at least 8 hours at refrigerated temperatures. The stability of this pharmaceutical composition allows for it to be commercially manufactured, shipped, and stored for a prolonged amount of time without a significant amount of degradation. In the clinical setting, it may be desirable to add the amount of the pharmaceutical solution which is to be administered to a subject to a pharmaceutically acceptable carrier prior to administration to a subject. For example, the pharmaceutical composition can be diluted in normal saline in order to reduce the pH of the pharmaceutical composition immediately before administration.

The therapeutic benefit of treating cancer with the pharmaceutical composition comprising LB-100 may be further enhanced by combining treatment with the pharmaceutical composition with other anti-cancer treatments including ionizing radiation and agents used for the treatment of cancer that induce abnormalities in DNA and/or that interfere with one or more constituents of the mitotic process. In particular, the anti-cancer activity of X-ray, DNA alkylating agents, DNA intercalating agents, and microtubule stabilizing and disrupting agents may be enhanced by treatment with the pharmaceutical composition comprising LB-100. The addition of spindle poisons and/or x-ray during or following exposure of cancers to the pharmaceutical composition comprising LB-100 may enhance the extent of cancer cell killing without increasing toxicity to normal cells. Specifically, combinations of the pharmaceutical composition comprising LB-100 with ionizing radiation (X-ray therapy), spindle poisons including taxol, vincristine (VCR), vinblastine (VBL), and/or DNA damaging agents including anthracyclines, bleomycin, cis-platin, etoposide, temozolomide, and nitrosoureas may be more effective anti-cancer regimens than standard regimens of single anti-cancer agents or combinations of agents in the absence of treatment with the pharmaceutical composition comprising LB-100. This list of anti-cancer drugs is not meant to be inclusive of all drugs that may be combined to advantage with the pharmaceutical composition comprising LB-100. Because the mechanism of action of LB-100 on TCTP and other regulatory molecules is distinct from all other approved anti-cancer regimens, the pharmaceutical composition comprising LB-100 may be used to advantage in combination with any of all FDA approved cancer regimens (for list of FDA-approved anti-cancer drugs see: www.accessdata.fda-.gov.gov.scripts/cder/onctools/druglist.cfm).

It should also be appreciated that pharmaceutical compositions comprising PP2A inhibitors other than LB-100 can be produced using the process described in Example 3 by substituting the amount of LB-100 for an appropriate amount of another PP2A inhibitor.

REFERENCES

Lu, J. et al., "The effect of a PP2A inhibitor on the nuclear receptor corepressor pathway in glioma," J. Neurosurg. Vol. 113(2):225-33 (2010);

Martiniova, L. et al., "Pharmacologic modulation of serine/threonine phosphorylation highly sensitizes PHEO in a MPC cell and mouse model to conventional chemotherapy," PLoS One vol. 6(2):e14678 (2011);

PCT International Application Publication No. WO 2008/097561 (Kovach & Johnson), published Aug. 14, 2008;

PCT International Application Publication No. WO 2009/020565 (Kovach & Zhuang), published Feb. 12, 2009;

PCT International Application Publication No. WO 2010/014141 (Kovach et al.), published Feb. 4, 2010;

PCT International Application Publication No. WO 2010/014220 (Kovach), published Feb. 4, 2010;

PCT International Application Publication No. WO 2010/014254 (Kovach & Johnson), published Feb. 4, 2010;

PCT International Application Publication No. WO 2010/147612 (Kovach), published Dec. 23, 2010;

PCT International Application Publication No. WO 2012/162535 (Kovach et al.), published Nov. 29, 2012;

U.S. Provisional Application No. 61/782,894 (Kovach), filed Mar. 14, 2013

Zhang, C. et al., "A synthetic cantharidin analog for the enhancement of doxorubicin suppression of stem cell-derived aggressive sarcoma," Biomaterials, vol. 31(36) 9535-43 (2010).

What is claimed is:

1. A method of treating a subject afflicted with a condition or disease amenable to treatment with a protein phosphatase 2A (PP2A) inhibitor, comprising administering to the subject (1) a pharmaceutical composition comprising (a) an effective amount of the PP2A inhibitor and (b) monosodium glutamate, wherein the PP2A inhibitor is a compound having the structure:

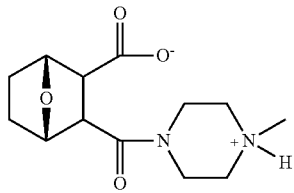

or a salt thereof, and wherein the pharmaceutical composition has a pH of 10-11; and (2) a chemotherapeutic agent in an amount such that the amount of the pharmaceutical composition and the amount of the chemotherapeutic agent together are effective to treat the subject, wherein the condition or disease is cancer, the cancer is soft tissue sarcoma and the chemotherapeutic agent is doxorubicin.

2. The method of claim 1, wherein the amount of the PP2A inhibitor administered to the subject is 1 mg to 12 mg per dose.

3. The method of claim 1, wherein the PP2A inhibitor is present in the pharmaceutical composition at a concentration of 1.0 mg/mL or the monosodium glutamate is present in the pharmaceutical composition at a concentration of 0.1 M.

4. The method of claim 3, wherein the PP2A inhibitor is present in the pharmaceutical composition at a concentration of 1.0 mg/mL and the monosodium glutamate is present in the pharmaceutical composition at a concentration of 0.1 M.

5. The method of claim 1, wherein the pH of the pharmaceutical composition is 10.5.

* * * * *